(12) United States Patent
Sun et al.

US011884566B2

(10) Patent No.: US 11,884,566 B2
(45) Date of Patent: Jan. 30, 2024

(54) ENGINEERED YEAST AS A METHOD FOR BIOREMEDIATION

(71) Applicant: Massachusetts Institute of Technology, Cambridge, MA (US)

(72) Inventors: George Le-Le Sun, Culver City, CA (US); Angela M. Belcher, Lexington, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 143 days.

(21) Appl. No.: 17/011,981

(22) Filed: Sep. 3, 2020

(65) Prior Publication Data

US 2021/0221719 A1    Jul. 22, 2021

Related U.S. Application Data

(62) Division of application No. 15/887,305, filed on Feb. 2, 2018, now Pat. No. 10,766,798.

(60) Provisional application No. 62/453,609, filed on Feb. 2, 2017.

(51) Int. Cl.
| | | |
|---|---|---|
| *C02F 3/34* | (2023.01) | |
| *C02F 3/32* | (2023.01) | |
| *E21C 41/22* | (2006.01) | |
| *C07K 14/825* | (2006.01) | |
| *C12N 1/06* | (2006.01) | |
| *C12N 1/16* | (2006.01) | |
| *C12N 9/02* | (2006.01) | |
| *C12N 9/10* | (2006.01) | |
| *C12N 9/88* | (2006.01) | |
| *E21C 41/32* | (2006.01) | |
| *C22B 3/18* | (2006.01) | |
| *C02F 101/20* | (2006.01) | |
| *C02F 103/10* | (2006.01) | |

(52) U.S. Cl.
CPC .............. *C02F 3/342* (2013.01); *C02F 3/322* (2013.01); *C02F 3/347* (2013.01); *C07K 14/825* (2013.01); *C12N 1/063* (2013.01); *C12N 1/16* (2013.01); *C12N 9/0008* (2013.01); *C12N 9/1029* (2013.01); *C12N 9/1085* (2013.01); *C12N 9/88* (2013.01); *E21C 41/22* (2013.01); *E21C 41/32* (2013.01); *C02F 2101/20* (2013.01); *C02F 2101/203* (2013.01); *C02F 2103/10* (2013.01); *C07K 2319/03* (2013.01); *C12Y 102/01011* (2013.01); *C12Y 203/01031* (2013.01); *C12Y 205/01047* (2013.01); *C12Y 404/01008* (2013.01); *C22B 3/18* (2013.01); *Y02P 10/20* (2015.11)

(58) Field of Classification Search
None
See application file for complete search history.

(56) References Cited

PUBLICATIONS

Pilon-Smits and Pilon, "Phytoremediation of Metals Using Transgenic Plants", Critical Reviews in Plant Sciences 21(5); 439-456 (Year: 2002).*
Lee and Kim, "Establishment of Tolerance to Both Cadmium and Copper Stress by Expressing *Arabidopsis* Phytochelatin Synthase in Cu Tolerant Yeast Mutant", J. Korean Soc. Appl. Biol. Chem. 53(1): 94-96 (Year: 2010).*
Behera, K.K. (2014). Phytoremediation, Transgenic Plants and Microbes. pp. 65 -85 In: Lichtfouse, E. (eds) Sustainable Agriculture Reviews. Sustainable Agriculture Reviews, vol. 13. Springer, Cham. (Year: 2013).*

* cited by examiner

*Primary Examiner* — Anand U Desai
(74) *Attorney, Agent, or Firm* — Honigman LLP

(57) ABSTRACT

Metal bioremediation and metal mining strategies can include compositions and methods.

21 Claims, 51 Drawing Sheets

Specification includes a Sequence Listing.

$SO_4^{2-} \equiv CrO_4^{2-}$
$PO_4^{3-} \equiv AsO_4^{3-}$

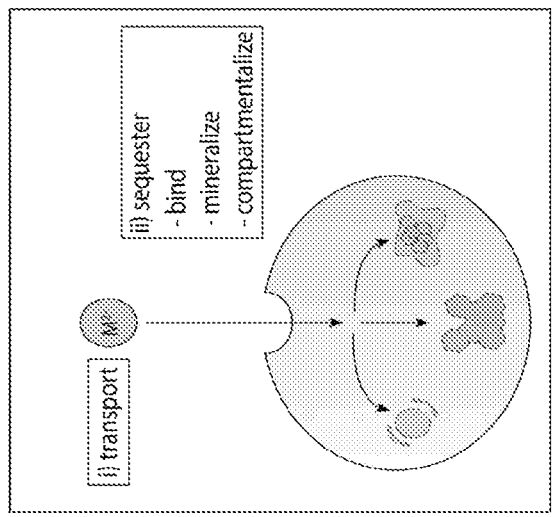
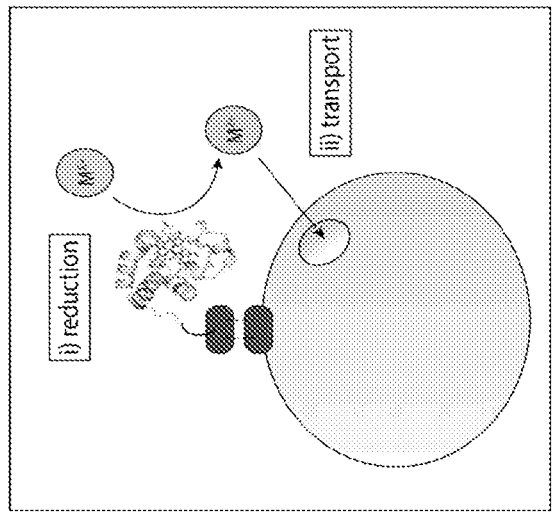
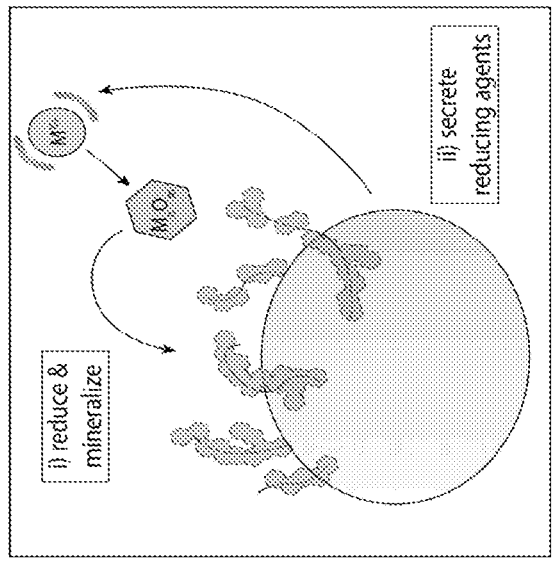
FIG. 20C
FIG. 20B
FIG. 20A

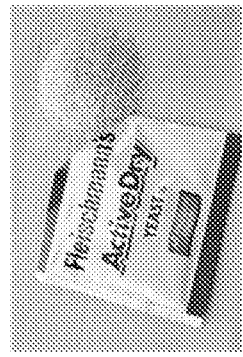
FIG. 34A
Active Dry Yeast
Compressed Yeast
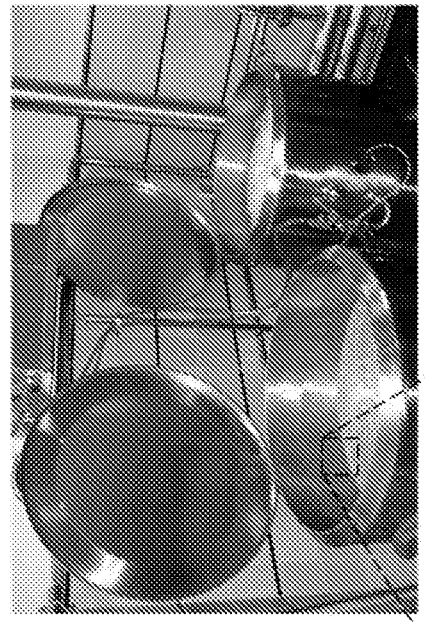
FIG. 34B
Brewing Yeast
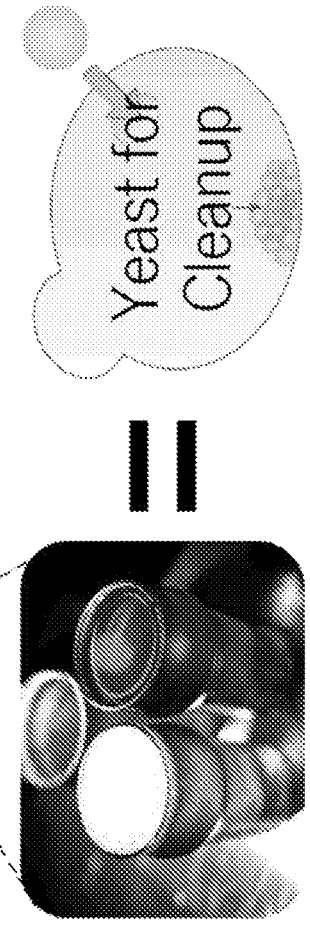
Yeast for Cleanup

ENGINEERED YEAST AS A METHOD FOR BIOREMEDIATION

CLAIM OF PRIORITY

This application is a divisional of U.S. patent application Ser. No. 15/887,305, filed Feb. 2, 2018, now U.S. Pat. No. 10,766,798, which claims the benefit of prior U.S. Provisional Application No. 62/453,609 filed on Feb. 2, 2017, each of which is incorporated by reference in its entirety.

SEQUENCE LISTING

The instant application contains a Sequence Listing which was submitted electronically in ASCII format in parent application Ser. No. 15/887,305, and is hereby incorporated by reference in its entirety. Said ASCII copy, created on Apr. 12, 2018, is named 14952_0550_SL.txt and is bytes in size.

TECHNICAL FIELD

This invention relates to metal bioremediation and metal mining.

BACKGROUND

Many heavy metals and organic compounds persistently contaminate public waters due to manufacturing processes, agricultural waste, and/or from corroding pipes and infrastructure. Examples such as lead, chromium, and copper leakage can cause long term physiological damage, and eventual deterioration of the respiratory organs and skeletal system. See www.epa.gov/airtoxics/hlthaf/chromium.html, which is incorporated by reference in its entirety. Chronic exposure, in most cases due to lack of water sanitation and monitoring, can cause long term health problems such as cancer and birth-related defects. See www.epa.gov/airtoxics/hlthef/hapglossaryrev.htm, which is incorporated by reference in its entirety.

Similarly, there are a variety of human-made and artificially derived organic wastes that pervade the public's water system that both harm the public and damage the environment. By-products and runoff from industrial sites such as trichloroethylene (TCE) and other compounds have been shown to affect the central nervous system, promote heart failure, and even cause cancer. See Kjellstrand, P., el al., "Irreversible effects of trichloroethylene exposure on the central nervous system." Scandinavian journal of work, environment & health (1980): 40-47, Watson, Rebecca E., et al. "Trichloroethylene-contaminated drinking water and congenital heart defects: a critical analysis of the literature." Reproductive Toxicology 21.2 (2006): 117-147, and Wartenberg, Daniel, Daniel Reyner, and Cheryl Siegel Scott. "Trichloroethylene and cancer: epidemiologic evidence." Environmental health perspectives108.Suppl 2 (2000): 161, each of which is incorporated by reference in its entirety.

Similarly, there are human-made reservoirs of waste caused by mining and drilling. For example, the oil sands, mainly centered in regions of Canada around the Athabasca watershed, have made a huge environmental impact due to the massive drilling & mining in the area. Most of the industrial work in the area has released toxic pollutants such as arsenic, chromium, lead, mixtures of reactive hydrocarbons, and irremediable tar. See Kelly, Erin N., et al., "Oil sands development contributes elements toxic at low concentrations to the Athabasca River and its tributaries." Proceedings of the National Academy of Sciences 107.37 (2010): 16178-16183, which is incorporated by reference in its entirety.

SUMMARY

In one aspect, a composition for remediating a metal to treat water can include a cell and a first oligomer of a metal binding protein expressed on a surface of the cell via a linker, where the linker can be tethered to the first oligomer of the metal binding protein and to a surface of the cell, the metal binding protein has specificity for a metal, and the first oligomer of the metal binding protein expressed on the surface of the cell is capable of aggregating with a second oligomer of the metal binding protein in the water upon binding a metal.

In certain embodiments, the cell can be yeast.

In certain embodiments, the linker can be a monomer of the metal binding protein.

In certain embodiments, the second oligomer of the metal binding protein can be secreted from the cell.

In certain embodiments, the metal can be a divalent metal.

In certain embodiments, the metal can be a transition metal.

In certain embodiments, the metal can be nickel, iron, copper, cobalt, lead, cadmium or mercury.

In certain embodiments, the metal binding protein can be glutamine synthetase.

In certain embodiments, the metal binding protein can be fused with a high affinity protein including a metal binding domain, wherein the metal binding domain has specificity for the metal.

In certain embodiments, the high affinity protein can be a plant metallothionein.

In certain embodiments, the metal binding protein can be expressed in a yeast host strain.

In another aspect, a method of remediating a metal to treat water can include preparing a composition comprising a cell and a first oligomer of a metal binding protein expressed on a surface of the cell via a linker, where the linker can be tethered to the first oligomer of the metal binding protein and to a surface of the cell, the metal binding protein has specificity for a metal, and the first oligomer of the metal binding protein expressed on the surface of the cell is capable of aggregating with a second oligomer of the metal binding protein in the water upon binding a metal, and contacting water with the composition.

In certain embodiments, the method can further include adding the second oligomer of the metal binding protein in the water.

In certain embodiments, the cell can be yeast.

In certain embodiments, the linker can be a monomer of the metal binding protein.

In certain embodiments, the second oligomer of the metal binding protein can be secreted from the cell.

In certain embodiments, the metal can be a divalent metal

In certain embodiments, the metal can be nickel, iron, copper, cobalt, lead, cadmium or mercury.

In certain embodiments, the metal binding protein can be glutamine synthetase.

In certain embodiments, the metal binding protein can be fused with a high affinity protein including a metal binding domain, wherein the metal binding domain has specificity for the metal.

In certain embodiments, the high affinity protein can be a plant metallothionein.

In certain embodiments, the second oligomer of the metal binding protein can be secreted from the cell via a signal peptide.

In certain embodiments, the signal peptide can be *S. cerevisiae*'s α-mating-factor.

In certain embodiments, the signal peptide can be AGA1/2 or EXG1.

In certain embodiments, the method can be performed at 20° C. or lower temperature.

In certain embodiments, the metal binding protein can be expressed in a yeast host strain.

In certain embodiments, the yeast host strain can be *Pichia pastoris*.

In another aspect, a method of making a composition for remediating a metal to treat water can include selecting a cell, and expressing a metal binding protein on a surface of the cell, and tethering a first oligomer of a metal binding protein expressed on a surface of the cell via a linker, where the linker is tethered to the first oligomer of the metal binding protein and to a surface of the cell, the metal binding protein has specificity for a metal, and the first oligomer of the metal binding protein expressed on the surface of the cell is capable of aggregating with a second oligomer of the metal binding protein in the water upon binding a metal.

In certain embodiments, the cell can be yeast.

In certain embodiments, the linker can be a monomer of the metal binding protein.

In certain embodiments, the second oligomer of the metal binding protein can be secreted from the cell.

In certain embodiments, the metal can be a divalent metal.

In certain embodiments, the metal can be a transition metal.

In certain embodiments, the metal can be nickel, iron, copper, cobalt, lead, cadmium or mercury.

In certain embodiments, the metal binding protein can be glutamine synthetase.

In certain embodiments, the method can further include appending a high affinity protein including to the metal binding protein, where the high affinity protein including a metal binding domain, wherein the metal binding domain has specificity for the metal.

In certain embodiments, the high affinity protein can be a plant metallothionein.

In certain embodiments, the method can further include expressing the metal binding protein in a yeast host strain.

In another aspect, a method of mining a metal can include preparing a composition including a cell and a first oligomer of a metal binding protein expressed on a surface of the cell via a linker, where the linker can be tethered to the first oligomer of the metal binding protein and to a surface of the cell, the metal binding protein has specificity for a metal and the first oligomer of the metal binding protein expressed on the surface of the cell is capable of aggregating with a second oligomer of the metal binding protein in the water upon binding a metal, contacting water with the composition and lysing the cell to obtain the metal.

In certain embodiments, the cell can be yeast.

In certain embodiments, the linker can be a monomer of the metal binding protein.

In certain embodiments, the second oligomer of the metal binding protein can be secreted from the cell.

In certain embodiments, the metal can be a divalent metal.

In certain embodiments, the metal can be a transition metal.

In certain embodiments, the transition metal can be nickel, iron, copper, cobalt, lead, cadmium or mercury.

In certain embodiments, the metal can be a noble metal.

In certain embodiments, the noble metal can be gold, silver or platinum.

In certain embodiments, the metal can be a rare-earth metal.

In certain embodiments, the rare-earth metal can be cerium (Ce), dysprosium (Dy), erbium (Er), europium (Eu), gadolinium (Gd), holmium (Ho), lanthanum (La), lutetium (Lu), neodymium (Nd), praseodymium (Pr), promethium (Pm), samarium (Sm), scandium (Sc), terbium (Tb), thulium (Tm), ytterbium (Yb) or yttrium (Y).

In certain embodiments, the metal binding protein can be glutamine synthetase.

In certain embodiments, the metal binding protein can be fused with a high affinity protein including a metal binding domain, wherein the metal binding domain has specificity for the metal.

In certain embodiments, the high affinity protein can be a plant metallothionein.

In certain embodiments, the metal binding protein can be expressed in a yeast host strain.

In another aspect, a composition for remediating a metal to treat water can include a cell expressing a membrane metal transporter, wherein the membrane metal transporter has specificity for a metal, a vacuole transporter and a metal sequestration protein.

In certain embodiments, the cell can be yeast.

In certain embodiments, an ubiquitination ligase can be deleted in the yeast.

In certain embodiments, the ubiquitination ligase can be BSD2.

In certain embodiments, the membrane transporter can be SMF1.

In certain embodiments, the vacuole transporter can be CCC1.

In certain embodiments, the metal sequestration protein can be a phytochelatin synthase.

In certain embodiments, the metal can be a divalent metal.

In certain embodiments, the metal can be a transition metal.

In certain embodiments, the metal can be cadmium.

In certain embodiments, SMF1 can be mutated to be sensitive to the metal.

In certain embodiments, the metal can be strontium, lead or mercury.

In certain embodiments, SMF1 can be mutated to destroy primary ubiquitination sites.

In certain embodiments, the membrane transporter can be Sul1 or Sul2.

In certain embodiments, the metal can be chromate.

In certain embodiments, the membrane transporter can be CTRL.

In certain embodiments, the metal can be copper.

In certain embodiments, the membrane transporter can be ZRT1.

In certain embodiments, the metal can be zinc.

In certain embodiments, the membrane transporter can be FRE1.

In certain embodiments, the metal can be iron.

In another aspect, a method of remediating a metal to treat water can include preparing a composition include a cell expressing a membrane metal transporter, where the membrane metal transporter has specificity for a metal, a vacuole transporter, and a metal sequestration protein, and contacting water with the composition.

In certain embodiments, the cell can be yeast.

In certain embodiments, an ubiquitination ligase can be deleted in the yeast.

In certain embodiments, the ubiquitination ligase can be BSD2.

In certain embodiments, the membrane transporter can be SMF1.

In certain embodiments, the vacuole transporter can be CCC1.

In certain embodiments, the metal sequestration protein can be a phytochelatin synthase. In certain embodiments, the metal can be a divalent metal.

In certain embodiments, the metal can be a transition metal.

In certain embodiments, the metal can be cadmium.

In certain embodiments, SMF1 can be mutated to be sensitive to the metal.

In certain embodiments, the metal can be strontium, lead or mercury.

In certain embodiments, SMF1 can be mutated to destroy primary ubiquitination sites.

In certain embodiments, the membrane transporter can be Sul1 or Sul2.

In certain embodiments, the metal can be chromate.

In certain embodiments, the membrane transporter can be CTRL.

In certain embodiments, the metal can be copper.

In certain embodiments, the membrane transporter can be ZRT1.

In certain embodiments, the metal can be zinc.

In certain embodiments, the membrane transporter can be FRE1.

In certain embodiments, the metal can be iron.

In another aspect, a method of mining a metal can include preparing a composition including a cell expressing a membrane metal transporter, where the membrane metal transporter has specificity for a metal, a vacuole transporter, and a metal sequestration protein, contacting water with the composition, and lysing the cell to obtain the metal.

In certain embodiments, the cell can be yeast.

In certain embodiments, an ubiquitination ligase can be deleted in the yeast.

In certain embodiments, the ubiquitination ligase can be BSD2.

In certain embodiments, the membrane transporter is SMF1.

In certain embodiments, the vacuole transporter can be CCC1.

In certain embodiments, the metal sequestration protein can be a phytochelatin synthase.

In certain embodiments, the metal can be a divalent metal.

In certain embodiments, the metal can be a transition metal.

In certain embodiments, the transition metal can be nickel, iron, copper, cobalt, lead, cadmium or mercury.

In certain embodiments, the metal can be lithium.

In certain embodiments, the metal can be a noble metal.

In certain embodiments, the noble metal can be gold, silver or platinum.

In certain embodiments, the metal can be a rare-earth metal.

In certain embodiments, the rare-earth metal can be cerium (Ce), dysprosium (Dy), erbium (Er), europium (Eu), gadolinium (Gd), holmium (Ho), lanthanum (La), lutetium (Lu), neodymium (Nd), praseodymium (Pr), promethium (Pm), samarium (Sm), scandium (Sc), terbium (Tb), thulium (Tm), ytterbium (Yb) or yttrium (Y).

In another aspect, a composition for remediating a metal to treat water can include a cell including a knocked-out enzyme required in sulfate-assimilation pathway, where the cell has specificity for reactions against a metal.

In certain embodiments, the enzyme can be HOM2, MET2, MET17 or CYS4.

In certain embodiments, in the metal can be a divalent metal.

In certain embodiments, the metal can be a transition metal.

In certain embodiments, the metal can be mercury, zinc, copper, cadmium or lead.

In certain embodiments, a surface of the cell can be modified to display a biomineralization peptide.

In certain embodiments, a surface of the cell can be modified to display a degenerate sequence that is biased towards cysteine, histidine, glutamic and aspartic acid residues.

In another aspect, a method of making a composition for remediating a metal can include deleting an enzyme required in sulfate-assimilation pathway in a cell, wherein the cell has specificity for reactions against a metal and culturing the cell in a medium supplemented with cysteine and/or methionine.

In certain embodiments, the enzyme can be HOM2, MET2, MET17 or CYS4.

In certain embodiments, the metal can be a divalent metal.

In certain embodiments, the metal can be a transition metal.

In certain embodiments, the metal can be mercury, zinc, copper, cadmium or lead.

In certain embodiments, the method can further include modifying a surface of the cell to display a biomineralization peptide.

In certain embodiments, the method can further include modifying a surface of the cell to display a degenerate sequence that are biased towards cysteine, histidine, glutamic or aspartic acid residues.

In certain embodiments, the method can further include culturing the cell in the medium supplemented with sodium sulfide.

In certain embodiments, the method can further include culturing the cell in the medium buffered to maintain a pH of the media above 4.

In another aspect, a method of forming a metal nanoparticle can include preparing a composition comprising a cell including a knocked-out enzyme required in sulfate-assimilation pathway, wherein the cell has specificity for reactions against a metal, contacting the composition with water, and purifying the metal nanoparticle from the cell.

In certain embodiments, the purifying the metal nanoparticle from the cell can include enzymatically digesting the cell wall, pelleting the cellular debris, and collecting the supernatant.

In certain embodiments, the metal nanoparticle can be HgS, CdS, ZnS or PbS.

In certain embodiments, the cell can be yeast.

In certain embodiments, the method can further include culturing the yeast in a growth medium with cysteine and/or methionine.

In certain embodiments, the method can further include tuning a size of the metal nanoparticle by changing a content of cysteine and/or methionine.

In certain embodiments, the method can further include tuning a production rate of the metal nanoparticle by changing a content of cysteine and/or methionine.

In another aspect, a method of remediating a metal to treat water can include preparing a cell including a knocked-out enzyme required in sulfate-assimilation pathway, where the cell has specificity reactions against for a metal and contacting water with the composition.

In certain embodiments, the enzyme can be HOM2, MET2, MET17 or CYS4.

In certain embodiments, the metal can be copper, cadmium or lead

In certain embodiments, a surface of the cell can be modified to display a biomineralization peptide.

In certain embodiments, a surface of the cell can be modified to display a degenerate sequence that is biased towards cysteine, histidine, glutamic or aspartic acid residues.

In another aspect, a method of mining a metal can include preparing a cell including a knocked-out enzyme required in sulfate-assimilation pathway, where the cell has specificity reactions against for a metal and contacting water with the composition.

In certain embodiments, the enzyme can be HOM2, MET2, MET17 or CYS4.

In certain embodiments, the metal can be a divalent metal.

In certain embodiments, the metal can be a transition metal.

In certain embodiments, the transition metal can be mercury, zinc, copper, cobalt, cadmium or lead.

In certain embodiments, the metal can be a noble metal.

In certain embodiments, the noble metal can be gold, silver or platinum.

In certain embodiments, the metal can be a rare-earth metal.

In certain embodiments, the rare-earth metal can be cerium (Ce), dysprosium (Dy), erbium (Er), europium (Eu), gadolinium (Gd), holmium (Ho), lanthanum (La), lutetium (Lu), neodymium (Nd), praseodymium (Pr), promethium (Pm), samarium (Sm), scandium (Sc), terbium (Tb), thulium (Tm), ytterbium (Yb) or yttrium (Y).

In certain embodiments, a surface of the cell can be modified to display a biomineralization peptide.

In certain embodiments, a surface of the cell can be modified to display a degenerate sequence that is biased towards cysteine, histidine, glutamic or aspartic acid residues.

Other aspects, embodiments, and features will be apparent from the following description, the drawings, and the claims.

BRIEF DESCRIPTION OF THE DRAWINGS

FIG. 3A shows crystal structure and TEM images of GS. FIG. 3B shows controlled protein aggregation of multiplier proteins (GS monomers). FIG. 3C shows controlled protein aggregation of multiplier proteins (GS oligomers).

FIG. 12A shows basic electron density mapping of sulfate and chromate show a high degree of structural resemblance. FIG. 12B shows overexpressing sulfate permeases Sul1 and 2 lead to increase chromate uptake.

FIG. 15A shows the absence or presence of cysteine or methionine either increases (ΔCYS4) or decreases sulfide production (ΔHOM2, MET2, MET17). FIG. 15B shows the absence of cysteine both reduces the onset of sulfide production and increases sulfide production yield for ΔMET17. FIG. shows effects on nutrient conditions on sulfide production.

FIG. 16A shows cultures grown overnight with Cu, Cd, Zn, Pb, Hg produce metal sulfides which give observable color changes indicative of CuS, CdS, ZnS, PbS and HgS precipitation. FIG. 16B shows analysis under TEM shows that metal sulfides such as CdS precipitate on the cell wall. FIG. 16C shows photos of Cds and PbS nanoparticle synthesis with/without yeast.

FIGS. 20A-20C shows examples of combining strategies 1-3. FIG. 20A shows biomineralization can be initiated with released sulfur compounds that subsequently nucleate on displayed biomineralization peptides. FIG. 20B shows high valent metals are reduced to divalent forms which are recognized by divalent metal transporters such as ZIPs, CTRs, FTRs, etc. FIG. 20C shows transported metals compartmentalized by a variety of mechanisms such as phytochelation, mineralization, or vacuole compartmentalization.

FIG. 21 discloses SEQ ID NO: 9.

FIG. 27A shows four families of plant MT proteins were taken from *Arabidopsis Thaliana* and expressed in the AGA I and AGA2 yeast display system. All families of MTs showed increased uptake of copper (FIG. 27B) and increased survivability in copper solutions (FIG. 27C).

FIG. 28A shows representative image of the mutant strain cell band that is higher in density (lower in the gradient) than compared to wild-type. FIG. 28B shows elemental analysis on collected cells from FIG. 28A showing a relative increase in metal uptake.

FIG. 29A shows schematic of heavy metal uptake pathways in yeast. FIG. 29B shows micrographs demonstrating that metal transporter SMF1 can be engineered to improve cadmium uptake. FIG. 29C shows cadmium uptake of WT yeast and engineered yeast strains in μM (top) and mg Cd 2±/g dry weight (DW, bottom). FIG. 29D shows SMF1 mutagenesis results.

FIG. 31A shows lead acetate strips giving a binary measurement on whether strains are capable of overproducing sulfur. FIG. 31B shows hydrogen sulfide columns marked with scales can determine hydrogen sulfide produced in cultures. FIGS. 31C and 31D show 1 ppm resolution columns undergo a purple change in the presence of hydrogen sulfide, whereas 5 ppm resolution columns undergo a brown change.

FIG. 32A cadmium removal using yeast sulfur production eliminates 90±5% of cadmium in solution. FIG. 32B Precipitated CdS particles excite at 350 nm and emit at 415 nm which is characteristic of CdS quantum dot behavior.

FIG. 33A shows images showing speckles of cadmium sulfide on the yeast cell wall. FIG. 33B shows particles are approximately 10-20 nm in diameter, with some encased in a biological shell which might be a consequence of cell wall encasing or during cell wall extraction.

FIGS. 34A-34B show established infrastructure to produce water-remediating yeast cultures for global applications. FIG. 34A shows the engineered yeast can be stored as freeze-dried or compressed packages, as they normally are in for consumer purposes, for long-term storage and portability. FIG. 34B shows the beer and wine industry have already developed a cheap and scalable source of yeast to scale the production of engineered strains for water remediation.

DETAILED DESCRIPTION

Figure 1:
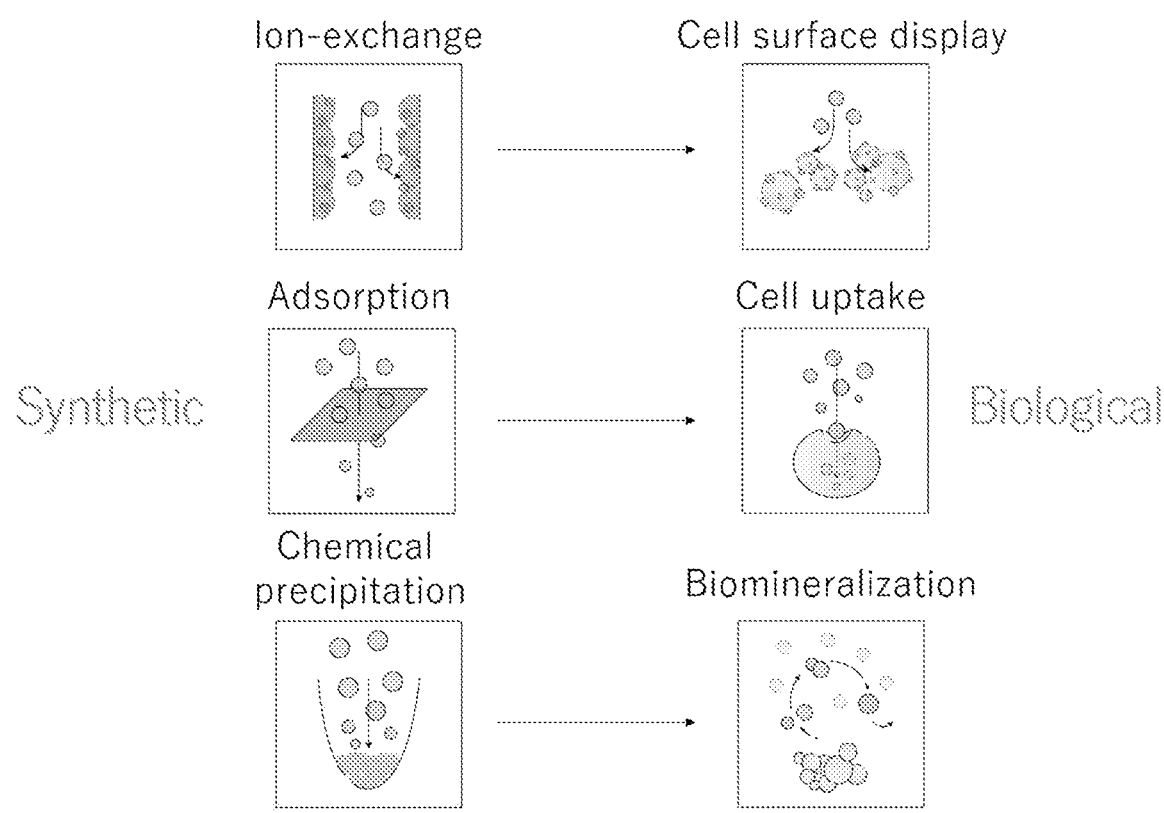
FIG. 1 shows analogies between physicochemical and engineered biological processes.

Many of the current industrial methods used for water treatment lack metal specificity and produce significant amounts of secondary waste which has made waste treatment an unsustainable process. See Gökhan Ekrem Ustün, Seval Kutlu Akal Solmaz, and Akin Birgül. Regeneration of industrial district wastewater using a combination of Fenton process and ion exchange—A case study. Resources, Conservation and Recycling, 52(2):425-440, 2007, and MA Barakat. New trends in removing heavy metals from industrial wastewater. Arabian Journal of Chemistry, 4(4):361-377, 2011, each of which is incorporated by reference in its entirety. The commonly used methods, ion-exchange, absorption, and chemical precipitation, also known as physicochemical methods, also have a high cost barrier preventing easy adoption in developing areas which are more likely to require intensive heavy metal treatment. See R K Rattan, SP Datta, P K Chhonkar, K Suribabu, and AK Singh. Long-term impact of irrigation with sewage effluents on heavy metal content in soils, crops and groundwater case study. Agriculture, Ecosystems & Environment, 109(3):310-322, 2005, which is incorporated by reference in its entirety.

Therefore, there needs to be more sustainable technologies for water treatment that require methods beyond just physical and chemical techniques. With current bioengineering techniques this balance between consumption and waste of metals can be exploited to favor metal accumulation and conversion without causing toxic effects. See Robert Wysocki and Markus J Minas. How *Saccharomyces cerevisiae* copes with toxic metals and metalloids. FEMS microbiology reviews, 34(6):925-951, 2010, which is incorporated by reference in its entirety. Simple organisms such as yeast can be genetically modified to act as living agents that sequester and remove waste from the environment. The added benefit is that yeast can be easily modified and self-propagate with minimal user intervention, making them a desirable engineerable platform which is cheap, scalable, and easily handled.

Current approaches to clean contaminated waters and landmasses are to synthesize chelating or reactive molecules to sequester heavy metals and toxic compounds. See Deshpande, Kiranmayi, et al., "Efficient sequestration and reduction of of hexavalent chromium with organosilica sol-gels," Journal of Materials Chemistry 15.29 (2005): 2997-3004, and Tang, Hao, et al., "Reductive dechlorination of activated carbon-adsorbed trichloroethylene by zero-valent iron: carbon as electron shuttle," Journal of environmental quality 40.6 (2011): 1878-1885, each of which is incorporated by reference in its entirety. However, these methods are costly and complex in design and are themselves prone to forming waste by-products. An alternative method can avoid these problems by using biological peptide chemistry and protein engineering a facile, modular, and scalable platform that uses protein binding domains as waste-containment agents. An advantage over chemically synthesizing polymers or fabricating devices is the simplicity of designing novel proteins using current gene editing technology, modularity (whereas chemicals and devices have to redo the cycle of theorization, construction and validation), and cost-efficient scalability when considering the large volumes of contaminated waters to treat. See Needels, Michael C., et al., "Generation and screening of an oligonucleotide-encoded synthetic peptide library," Proceedings of the National Academy of Sciences 90.22 (1993): 10700-10704, and Houghten, Richard A., et al., "Generation and use of synthetic peptide combinatorial libraries for basic research and drug discovery," (1991): 84-86, each of which is incorporated by reference in its entirety.

On the other end of the spectrum, current research is pursuing bioremediation techniques that focus on using natural organisms to remove or consume waste, thereby providing an environmentally friendlier and natural alternative for managing waste, Historically, bioremediation was first invented by George Robinson in the 1960s by first demonstrating the use of bacteria to degrade petroleum and other hydrocarbon based pollutants. See Golding, Lynnea, "Bioremediation of Pesticides," which is incorporated by reference in its entirety. However, the process in which organisms break down hazardous substances into less toxic or usable forms has been a universal concept in all living organisms. Especially so, the management of metal concentration and localization in cells plays an incredibly important role in cellular homeostasis. Of all the species that have adapted to handle highly polluted environments, the most highly studied are plants, fungi, and bacteria. See Juwarkar, Asha A., Sanjeev K. Singh, and Ackmez Mudhoo, "A comprehensive overview of elements in bioremediation," Reviews in Environmental Science and Bio/Technology 9.3 (2010): 215-288, and Ron, Eliora Z. and Eugene Rosenberg, "Biosurfactants and oil bioremediation," Current opinion in biotechnology 13.3 (2002): 249-252, each of which is incorporated by reference in its entirety. However, given the diversity of plants and bacteria and their respective genes and proteins that play a role in heavy metal uptake bring into question whether using native organisms with specific environmental and growth conditions is a foreseeable platform for a creating a scalable and accessible bioremedation technology. Therefore, the next step should be in favor of using an engineerable host which can be manipulated to function analogously to plants and/or bacteria by expressing the relevant proteins using current technologies in molecular and genetic engineering.

Therefore, protein engineering can be applied on yeast to create the next biological platform for bioremediation. Yeast have been a model organism for genetic studies since the age of Louis Pasteur, and since then yeast are becoming increasingly relevant in gene expression and protein studies as genetic engineering technology continues to develop. The field of yeast biology has already optimized genetic manipulation techniques such as transformations, genomic recombination, heterologous protein expression, and design and function of genetic circuits. In addition, many of the studies that have identified phytochelatins, metallothioneins, metal transporters, and cytochromes were either discovered in yeast: or functionally identified using functional complementation of yeast mutants proving that yeast already contain the basic machinery for metal transport, uptake, and sequestration. Expressing the relevant proteins and enzymes can enable uptake and sequester metals beyond the normal limitations of wild-type yeast and vastly beyond the hazardous standards set by the EPA.

Disclosed herein is a method for remediating a metal to treat water or for mining a metal to take the principles from ion-exchange, adsorption, and chemical precipitation and create analogous strategies in yeast. The act of binding metals (ion-exchange), internalization (adsorption), and conversion (chemical precipitation) are naturally found in biological processes for cellular homeostasis. See Julian C Rutherford and Amanda J Bird. Metal-responsive transcription factors that regulate iron, zinc, and copper homeostasis in eukaryotic cells. Eukaryotic cell, 3(1):1-13, 2004, which is incorporated by reference in its entirety. In certain embodiments, genetically engineered yeast can be used as a means to bioremediate waste waters. In certain embodiments, a combination of yeast display to bind metals onto the surface of yeast, over-expression of metal transporters to uptake metals intracellularly, and biochemical pathways that enables to recycle captured metals using metabolic enzymes can be used. In parallel, yeast enzymes can be developed to consume and/or degrade harmful organic compounds such as TCE generated from mining and other environmentally unfriendly practices. Given current bioengineering techniques, these mechanisms can be perturbed to favor metal accumulation by exposing more metal binding proteins, increasing activity of metal transporters, or promoting specific metal reaction pathways, for example. This leads to the creation of three unique strategies: cell surface display, cell uptake, and biomineralization (FIG. 1): 1) cell surface display of metal binding proteins mimics the mechanism of action of surface functionalized ion-exchange resins; 2) physical uptake of metals can be achieved by engineering hyperactive metal transporters; and 3) yeast can supply reactive by-products to mineralize metals from solution, instead of relying on external chemicals for chemical precipitation. Despite differing approaches, all three can be optimized based on metal capture capacity, metal specificity and selectivity, and yeast metal tolerance and survivability. In certain embodiments, the metal can be a divalent metal. In certain other embodiments, the metal can be a transition metal.

These strategies closely mimic the mechanism of action of the physicochemical methods mentioned above, yet address the limitations of cost, development time, and scalability. It is possible to optimize these strategies such that organisms, like yeast, can be used to treat and manage waste for the environment and the public.

Yeast Display Capture Capacity

Yeast display as a method for material capture is limited by cell density and the expression number of peptide/proteins per cell surface. Nominal capture capacity is in the micromolar range assuming culture densities from ten to one hundred thousand cells per milliliter, expression levels ranging from ten to one hundred thousand (experimentally determined), and effective binding sites per peptide/protein between 1 and 10. Uptake can then be defined as:

$$\text{uptake } [M] = N_c \times N_e \times n \div N_A$$

Where
$N_c$=density of cells
$N_e$=expression number per cell
n=binding sites per expression
$N_A$=Avogadro's number (6.022e23)

Density Changes Due to Metal Uptake

Assuming transporter metal uptake of 100 μM (denoted as M; empirically determined), and nominal values for yeast volume and density, then density changes due to metal uptake can be determined with:

$$\Delta \rho = \rho + \frac{m_{metals}}{V}$$

Assuming volume does not increase dramatically with metal internalization. The added mass contributed by the metals can be calculated with $$m_{metals} = M \times V \times MW \div N_A$$

Where
ρ=yeast density (1.129 g/mL)
V=yeast volume ($35 \times 10^{-15}$ mL)
$m_{metals}$=added mass due to metal
MW=metal molecular weight
$N_A$=Avogadro's number (6.022e23)

Using a lower end molecular weight (MW) of 54.9 (manganese) and a higher end molecular weight of 207.2 (lead) density changes can range from 2-25%.

Strategy 1—Cell Surface Capture—Increasing Capture Capacity of Yeast Display Using "Multiplier" Proteins.

Strategy 1 is focused on overcoming the low metal capture capacity of yeast display when compared to physicochemical techniques such as ion-exchange.

A composition and a method for remediating a metal to treat water or for mining a metal can include a cell and a first oligomer of a metal binding protein expressed on a surface of the cell via a linker, where the linker is tethered to the first oligomer of the metal binding protein and to a surface of the cell, the metal binding protein has specificity for a metal; and the first oligomer of the metal binding protein expressed on the surface of the cell is capable of aggregating with a second oligomer of the metal binding protein in the water upon binding a metal. The oligomer can be an oligonucleotide having 1 to 30 nucleotides, for example, 3 to 25 nucleotides.

In certain embodiments, a "multiplier" protein system can be used, where protein monomers tethered to a metal binding protein (MBP) aggregate onto the yeast surface, effectively multiplying the number of MBPs displayed per cell. These yeast aggregates are able to capture 1-10 mM of copper, cobalt, and cadmium at 1 $OD_{600}$ of cells; 2-orders of magnitude greater than any existing techniques on yeast display capture of heavy metals. In certain embodiments, metal specificity can be controlled by engineering the tethered MBPs. In certain embodiments, engineered plant metallothioneins can be used. Engineered plant metallothioneins are small proteins with metal specificity towards mercury, cadmium, lead, and a range of other divalent metals. In certain embodiments, the multiplier protein can be engineered to aggregate in response to various stimuli, or to be reversible, such that this strategy can both capture, and then release the collected metal contaminates.

In certain embodiments, the metal can be a divalent metal. In certain other embodiments, the metal can be a transition metal.

Strategy 2-Metal Uptake—Creating Yeast Hyper Accumulators Using Membrane and Vacuole Transporters.

Strategy 2 exploits the yeast metal transport system to hyper accumulate metals present in the environment.

A composition and a method for remediating a metal to treat water or for mining a metal can include a cell expressing a membrane metal transporter, where the membrane metal transporter has specificity for a metal, a vacuole transporter, and a metal sequestration protein. The composition can be a component of a water treatment kit.

In certain embodiments, the membrane transporter is expressed on the mitochondrial membrane. In certain embodiments, the membrane transporter is SMF1. In certain embodiments, the vacuole transporter is CCC1. In certain embodiments, both membrane transporter, SMF1, and vacuole transporter CCC1, can be used in combination to uptake heavy metals such as cadmium. Compared to wild-type, cadmium uptake increased by 10-fold. In certain embodiments, SMF I can be engineered to become sensitive to other metals such as strontium, lead, and mercury. In certain embodiments, conserved transmembrane domains can be identified through global multi-alignments and mutagenized these portions to create SMF1 libraries. These libraries can be tested against different metals and assayed based on density changes because of the mass increase due to metal accumulation.

In addition, to counter the toxicity effects of metal uptake, plant phytochelatin synthase, TaPCS1 can be expressed to increase metal tolerance. The combined expression of CCC1 and TaPCS1 allows yeast to survive at 100 μM cadmium, whereas wild-type yeast dies at concentrations beyond 5 μM.

In certain embodiments, the metal can be a divalent metal. In certain other embodiments, the metal can be a transition metal.

Strategy 3—Metal Conversion—Using Yeast's Sulfur by-Products to Precipitate Heavy Metals Strategy 3 uses sulfur released from engineered yeast to react with metals in solution.

A composition and a method for remediating a metal to treat water or for mining a metal can include a cell including a knocked-out enzyme required in sulfate-assimilation pathway, where the cell has specificity for a metal.

In certain embodiments, enzymes required in the sulfate-assimilation pathway can be knocked out to retard the conversion of sulfates to thiol metabolites allowing a build-up of hydrogen sulfide precursors. In addition, nutrient sources such as cysteine and methionine can be varied to affect the production rate and quantity of produced hydrogen sulfide.

Preliminary studies show sulfur accumulating up to 1 mM in culture which readily reacts with copper, cadmium, and lead. Investigation under TEM shows that reacted metal sulfides form consistently sized nanoparticles in the range of 20-50 nm on the yeast cell wall. Particles are easily purified by enzymatically digesting the cell wall, pelleting the cellular debri, and collecting the supernatant. Specifically, purified CdS particles exhibit a unique excitation and emission wavelength at 395 and 430 respectively, characteristic of quantum dots in that size-range. The purity and quality of yeast generated quantum dots can be confirmed using X-ray diffraction and TEM. In parallel, various conditions such as pH, media composition, and strain-type can be tested to understand the effect on metal sulfide formation with respects to size, crystallinity, quantity, and monodispersity.

In certain embodiments, the metal can be a divalent metal. In certain other embodiments, the metal can be a transition metal.

1. Strategy 1—Cell Surface Capture

A paper by Ruta et. al. functionalized the yeast surface with hexapeptides to capture a range of common divalent metals such as nickel, copper, iron, etc. In addition, cells with displaying metal binding proteins tend to be more metal tolerant, as metals captured extracellularly are prevented from entering the cell body. See Robert Wysocki and Markus J Minas. Flow *Saccharomyces cerevisiae* copes with toxic metals and metalloids. FEMS microbiology reviews, 34(6):925-951, 2010, Lavinia Liliana Ruta, Ralph Kissen, Ioana Nicolau, Aurora Daniela Neagoe, Andrei Josa. Petrescu, Atle M Bones, and Ileana Cornelia Farcasanu. Heavy metal accumulation by *Saccharomyces cerevisiae* cells armed with metal binding hexapeptides targeted to the inner face of the plasma membrane. Applied Microbiology and Biotechnology, pages 1-15, 2017, and Oscar N Ruiz, Derry Alvarez, Gloriene Gonzalez-Ruiz, and Cesar Torres. Characterization of mercury bioremediation by transgenic bacteria expressing metallothionein and polyphosphate kinase. BMC biotechnology, 11(1):82, 2011, each of which is incorporated by reference in its entirety. However, current cell surface binding capacities, which are in the 1.1.M range, still cannot compete with ion-exchange due to their extremely low capture capacity and poor capture to cell weight ratio. See MA Barakat. New trends in removing heavy metals from industrial wastewater. Arabian Journal of Chemistry, 4(4):361-377, 2011, and P Stathi, IT Papadas, A Tselepidou, and Y Deligiannakis. Heavy-metal uptake by a high cation-exchange-capacity montmorillonite: The role of permanent charge sites. Global nest, 12(3):248-255,2010, each of which is incorporated by reference in its entirety. Therefore, the number of binding sites per cell is the greatest limiting factor that limits the effectiveness of cell surface display.

1.1. Using Multiplier Proteins to Increase Metal Uptake Capacity

Figure 2:
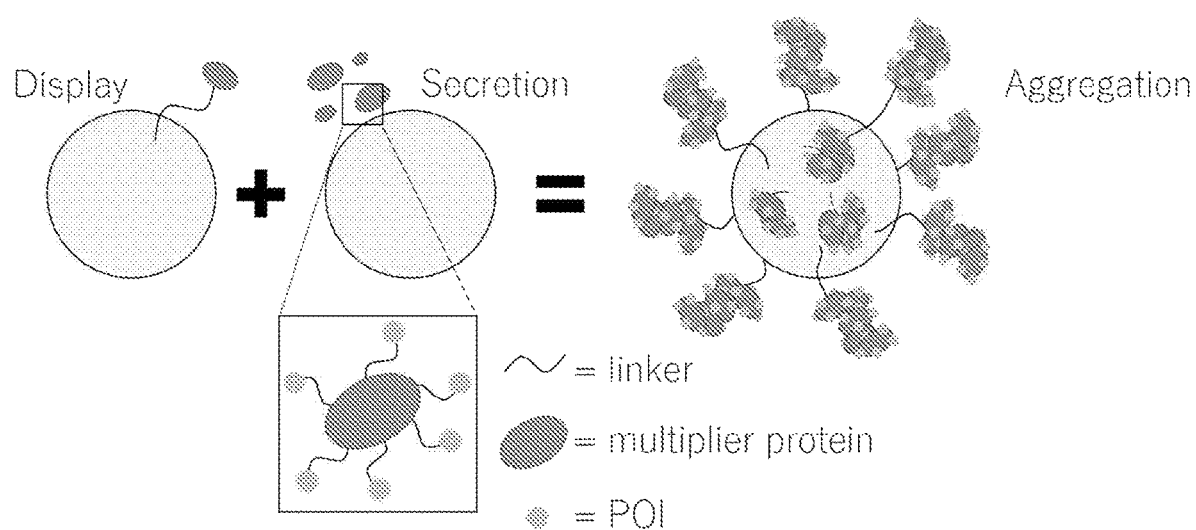
FIG. 2 shows yeast displayed+multiplier protein system.

One method to address the limitation of cell surface display is to display multiple repeats of the same binding protein on a single displayed unit. Going one step further, one can instead aggregate proteins onto the yeast surface to create a metal capture network. This mechanism of aggregating proteins onto the yeast surface can be achieved by a combination of displaying and secreting so called "multiplier" proteins, proteins that oligomerize to themselves. For example, an engineered yeast strain can display a single multiplier protein, and the same, or another yeast strain, can secrete the same protein into the media. In the presence of metal the secreted proteins can oligomerize and inevitably anchor to the protein displayed on the yeast surface, thereby forming an aggregated network. This network anchored on the yeast surface effectively multiplies the expression level of the typically single displayed protein on the yeast surface (FIG. 2). FIG. 2 shows one cell displaying a protein oligomer, and another (or the same cell) can secrete protein monomers that aggregate onto the displayed protein. Linkers fused with other proteins of interest (POI) can be appended to the oligomers to tailor the network's metal binding properties.

Figure 3A:
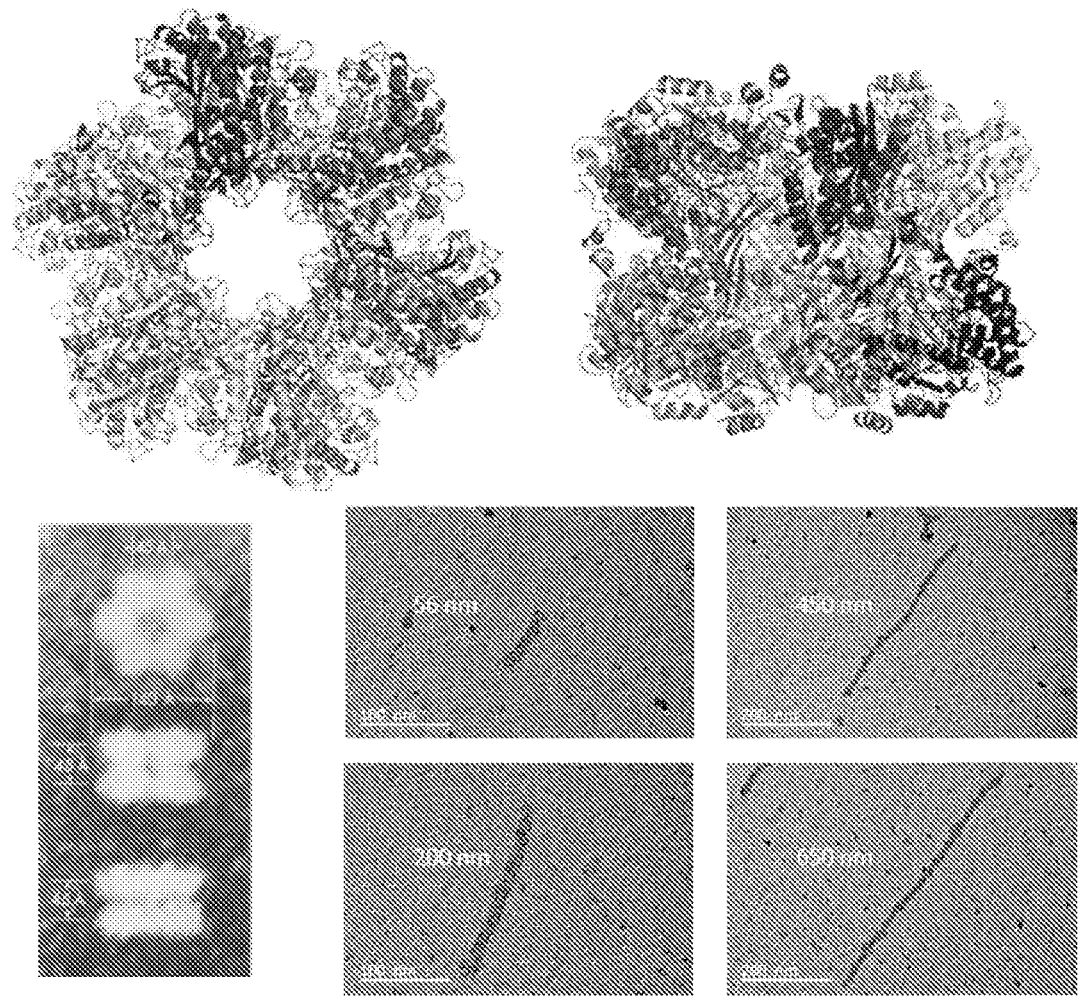
FIGS. 3A-3C show structure of multiplier proteins (GS).
Figure 3B:
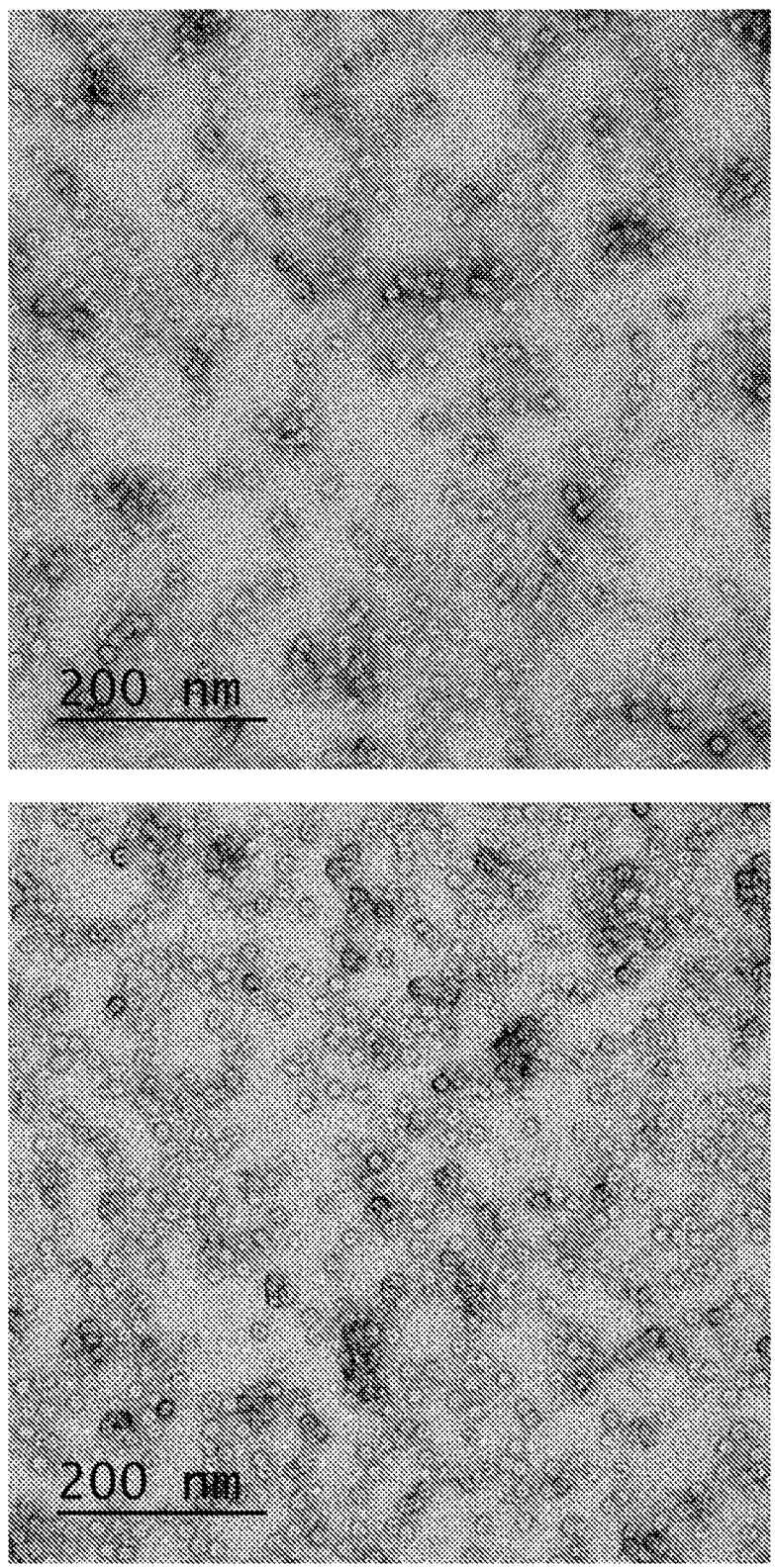
Figure 3C:
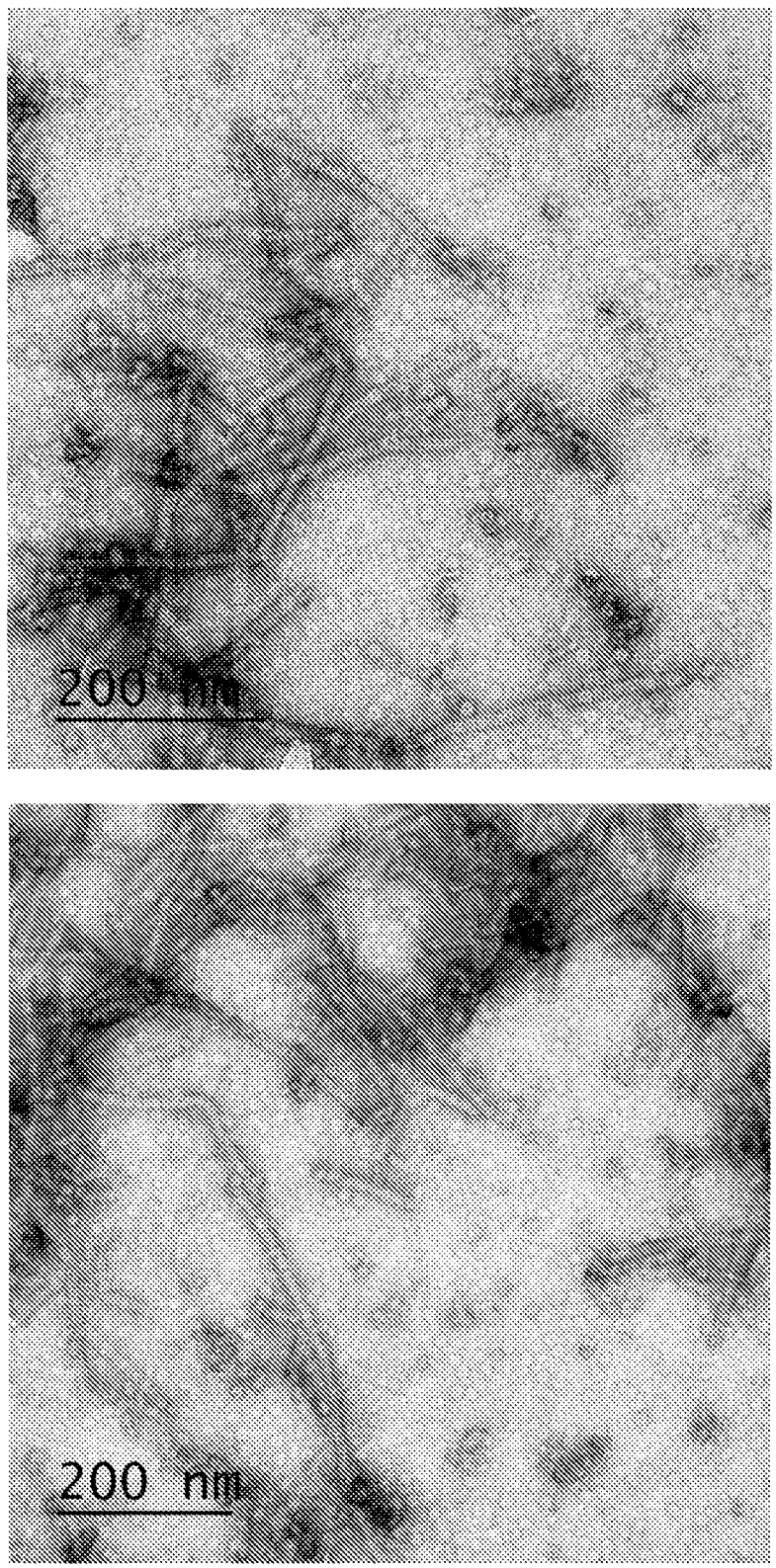

In certain embodiments, the multiplier protein used in this strategy can be glutamine synthetase (GS for short; PDB: 2GLS), a bacterial protein which has been studied for its role in glutamate and glutamine synthesis. One unique property that has been somewhat overlooked is its ability to aggregate in a structurally unique pattern in the presence of divalent metals (FIGS. 3A-3C). In FIGS. 3A-3C, top images are rendered structures of GS from crystallographic data. Bottom are TEM images of GS units as well as aggregates. See Bennett M Shapiro and ER Stadtman. [130] glutamine synthetase (*Escherichia coli*). Methods in enzymology, 17:910-922, 1970, which is incorporated by reference in its entirety. The rate of aggregation and the degree of oligomerization is dependent on exposure time and concentration of metal.

Figure 5:
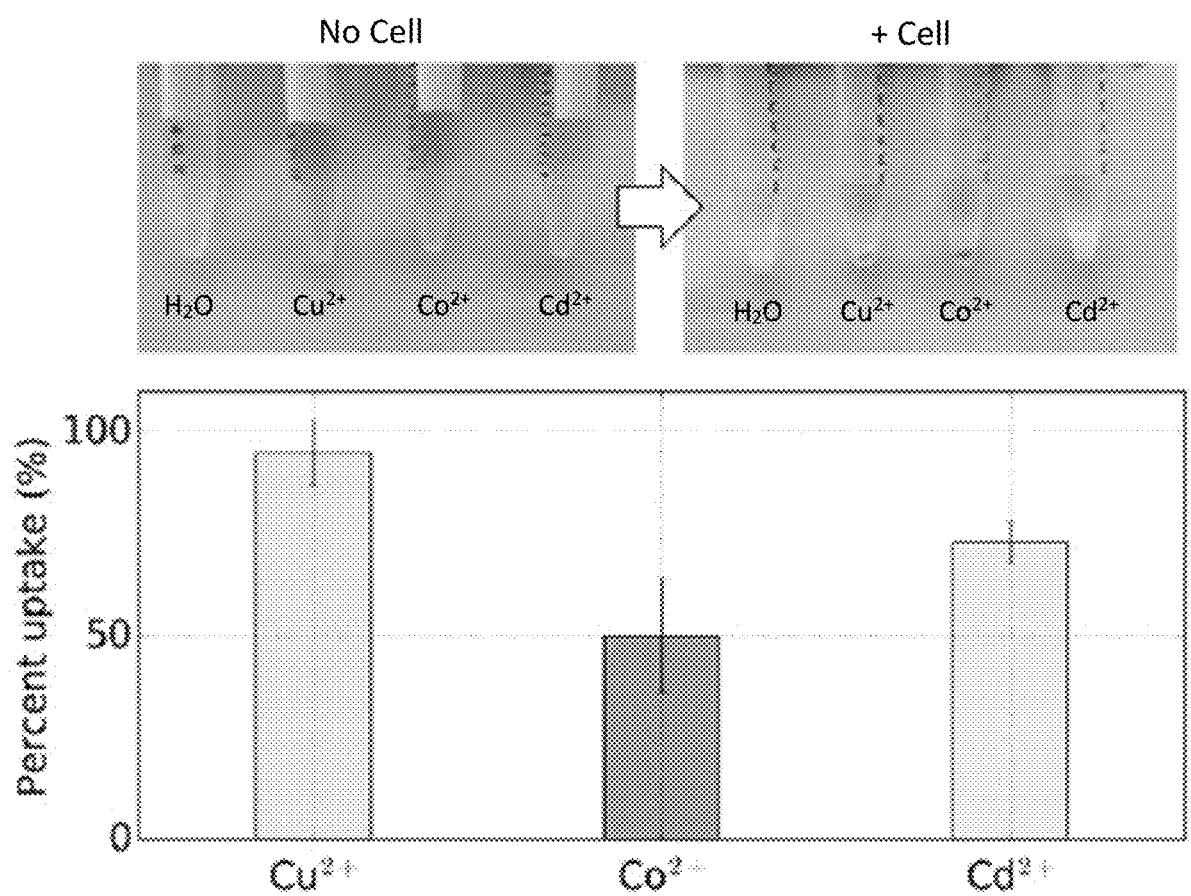
FIG. 5 shows metal uptake with yeast+GS.

As a pilot-study, glutamine synthetase was overexpressed and purified from BL21 bacteria cells and added at 100 µM to the medium containing yeast displaying the same protein. Aggregation was visible by eye as well as examined using scanning electron microscopy. The effect of aggregation on metal uptake was quantitatively measured using inductively coupled plasma (ICP). Species such as nickel, iron, and copper had uptakes of 5-10 mM whereas cobalt, lead, and cadmium ranged from 1-5 mM given 1 $OD_{600}$ of cells in synthetically defined media (CSM). The difference in binding capacity between species like iron and copper to the heavier and larger atoms such as lead and cadmium could be due to different GS binding affinities. In FIG. 5, top image shows (tubes labeled left to right) solution of yeast, and yeast with 10 mM Cu, mM Co, and 10 mM Cd. The right image shows the same conditions but with the addition of 100 µM GS. Bottom figure shows metal uptake percentage quantified using ICP.

Without cells, glutamine synthetase alone is an effective metal binder. But with the addition of yeast, the aggregated network aggregates and sinks, simply due to the yeast's higher density allowing for easy separation from treated waters. Another advantage is that the aggregate can now be packed onto filtration or chromatography columns as membrane filters are typically sub-micron to micron which can easily exclude yeasts. So rather than handling liquids of culture and proteins, one can instead package these aggregated complexes in filtration columns that are easy to handle and use.

1.2. Tethering Metal Binding Proteins/Motifs for Increase Metal Specificity

To further augment the binding capacity of this multiplier system, additional proteins containing metal binding domains can be fused onto GS to increase binding capacity and tailor for metal specificity. In certain embodiments, proteins such as plant metallothioneins can be used because of their low molecular weight and high metal binding affinity as well as their multiple binding domains (between 7-14). See Christopher Cobbett and Peter Goldsbrough. Phytochelatins and metallothioneins: roles in heavy metal detoxification and homeostasis. Annual review of plant biology, 53(1):159-182, 2002, which is incorporated by reference in its entirety. Also, plant metallothioneins have a high affinity for other metals such as mercury and strontium that do not bind to GS. See Gerald Henkel and Bernt Krebs. Metallothioneins: Zinc, cadmium, mercury, and copper thiolates and selenolates mimicking protein active site features-structural aspects and biological implications. Chemical reviews, 104 (2):801-824, 2004, and Ivo Fabrik, Jiri Kukacka, Jiri Baloun, Ivo Sotomik, Vojtech Adam, Richard Prusa, David Vajtr, Petr Babula, and Rene Kizek. Electrochemical investigation of strontium—metallothionein interactions—analysis of serum and urine of patients with osteoporosis. Electroanalysis, 21(3-5):650-656, 2009, each of which is incorporated by reference in its entirety.

In certain embodiments, these plant metallothioneins (MTs) can be appended to the N' terminus of GS, as GS's main aggregating domain is located at the C' terminus (determined by analyzing the crystal structure and using predictive algorithms such as TANGO (see Ana-Maria Fernandez-Escamilla, Frederic Rousseau, Joost Schymkowitz, and Luis Serrano. Prediction of sequence-dependent and mutational effects on the aggregation of peptides and proteins. Nature biotechnology, 22(10):1302, 2004, which is incorporated by reference in its entirety). By tethering plant MTs on the GS multiplier protein system, metal binding capacities can be at least doubled, and more so binding affinities can now favor heavier elements such as cadmium, lead, and mercury.

1.3. Additional Embodiments to Improve Secretion Yields

Figure 6:
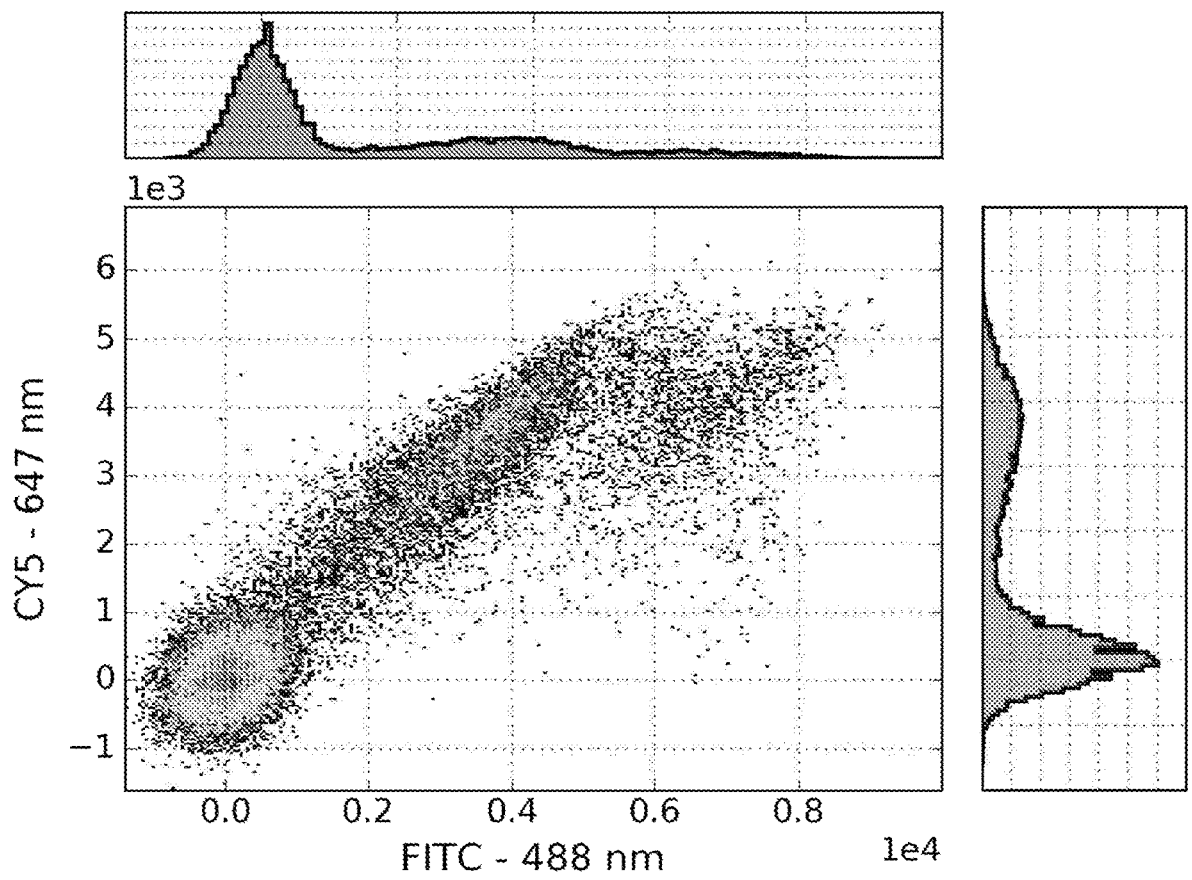
FIG. 6 shows quantifying GS expression level using FACS.

The biggest limitation of the current multiplier protein system is the low expression levels of GS, both with respects to display and secretion. Even with codon optimization, GS is displayed on less than 20% of cells (FIG. 6), and secretion levels are barely detectable via Western Blot (not shown). FIG. 6 shows 2D histogram of FACS data observing fluorescently tagged N'-terminus HA tag (FITC,$\lambda$ex=488 nm) and C'-terminus Myc tag (CY5,$\lambda_{ex}$=647 nm).

Western blots of cell lysate show two bands with equal intensity, one with the correct molecular weight of GS, and the larger being GS+signal peptide. Therefore, there are two inefficiencies for GS export, the first being proper cleavage of the signal pep-tide, and the second is the transport out of the cell after peptide cleavage.

In certain embodiments, *S. cerevisiae*'s α-mating-factor can be used as a signal peptide.

In certain embodiments, other mating factors such as AGA1/2 and EXG1 can be used to improve yield as they are processed through different secretion pathways possibly allowing easier passage and folding. See Lars Ellgaard, Maurizio Molinari, and Ari Helenius. Setting the standards: quality control in the secretory pathway. Science, 286 (5446):1882-1888, 1999, and Gunnar von Heijne. The signal peptide. Journal of Membrane Biology, 115(3):195-201, 1990, each of which is incorporated by reference in its entirety.

In certain embodiments, the expression process can be conducted at 20° C. (or lower) to improve proper GS folding in order to avoid the cell's unfolded protein response which destroys poorly folded proteins in the endoplasmic reticulum, and is often a major problem for secreting heterologous proteins in yeast. See David Ron and Peter Walter. Signal integration in the endoplasmic reticulum unfolded protein response. Nature reviews. Molecular cell biology, 8(7):519, 2007, and Dagang Huang, Patrick R Gore, and Eric V Shusta. Increasing yeast secretion of heterologous proteins by regulating expression rates and post-secretory loss. Biotechnology and bioengineering, 101(6):1264-1275, 2008, each of which is incorporated by reference in its entirety.

In other embodiments, GS can be expressed in *Pichia Pastoris*, a commonly used yeast host strain for heterologous expression of prokaryotic and eukaryotic proteins that has a well defined secretory pathway.

In other embodiments, a different multiplier besides GS can be used. The identity of the protein is not a major concern just as long as it can be sufficiently displayed and secreted.

Another survey can be done through the literature and the protein data bank (www.rcsb.org/pdb/home/home.do, which is incorporated by reference in its entirety). To identify a suitable candidate, a multiplier protein must have well characterized and controllable aggregating properties. These aggregating properties must remain when fused to another protein (e.g. plant MTs) either at the N' or C' terminus and secrete more efficiently than GS.

2. Strategy 2—Metal Uptake

Plants have evolved a unique ability to tolerate heavily contaminated soils, specifically heavy metals such as cadmium, arsenic, chromium, etc. See Nicoletta Rascio and Flavia Navari-Izzo. Heavy metal hyperaccumulating plants: how and why do they do it? and what makes them so interesting? Plant science, 180(2):169-181, 2011, and Majeti Narasimha Vara Prasad and Helena Maria de Oliveira Freitas. Metal hyperaccumulation in plants: biodiversity prospecting for phytoremediation technology. Electronic journal of biotechnology, 6(3):285-321, 2003, each of which is incorporated by reference in its entirety. Researchers have attributed this unique ability to a combination of hyperactive metal transporters and a variety of metal-binding proteins that uptake and guard against metal poisoning. See Stephan Clemens, Michael G Palmgren, and Ute Kramer. A long way ahead: understanding and engineering plant metal accumulation. Trends in plant science, 7(7):309-315, 2002, which is incorporated by reference in its entirety. Strategy 2 utilizes a parallel mechanism to that of plants by endowing yeast strains with hyperactive membrane and vacuole transporters, as well as promiscuous metal binding proteins to create yeast hyperaccumulators that internalize large amounts of metals.

2.1. Expressing Relevant Transporters and Proteins to Achieve Hyperaccumulating Activity Much like plants, the requirements for metal hyperaccumulation in yeast are: 1) membrane metal transporters; 2) vacuole transporters; and 3) metal sequestration proteins to increase metal tolerance.

Out of 16 transporters screened, yeast SMF1 was chosen because of its well-studied mechanism of action in addition to its ability to transport a variety of divalent metals. See P Courville, R Chaloupka, and MFM Cellier. Recent progress in structure—function analyses of nramp proton-dependent metal-ion transporters this paper is one of a selection of papers published in this special issue, entitled csbmcbmembrane proteins in health and disease. Biochemistry and Cell Biology, 84(6):960-978, 2006, which is incorporated by reference in its entirety. most metal transporters are heavily regulated by proteases and ubiquitinases to balance the concentration of intracellular metals. See Elina Nikko, James A Sullivan, and Hugh RB Pelham. Arrestin-like proteins mediate ubiquitination and endocytosis of the yeast metal transporter smf1. EMBO reports, 9(12):1216-1221, 2008, and Steven Lam-Yuk-Tseung, Gregory Govoni, John Forbes, and Philippe Gros. Iron transport by nramp2/dmt1: ph regulation of transport by 2 histidines in transmembrane domain 6. Blood, 101(9):3699-3707, 2003, each of which is incorporated by reference in its entirety. The major SMF1 ubiquitination ligase, BSD2, was deleted (see Xiu Fen Liu and Valeria Cizewski Culotta. Post-translation control of nramp metal transport in yeast role of metal ions and the bsd2 gene. Journal of Biological Chemistry, 274(8):4863-4868, 1999, which is incorporated by reference in its entirety) with no signs of compromising yeast health. In addition, lysine residues K33,34 in SMF1 were mutated to arginines to destroy the primary ubiquitination sites of SMF1 that are recognized by other ubiquitination ligases. See Elina Nikko, James A Sullivan, and Hugh RB Pelham. Arrestin-like proteins mediate ubiquitination and endocytosis of the yeast metal transporter smf1. EMBO reports, 9(12):1216-1221, 2008, which is incorporated by reference in its entirety. The engineered SMF1 is referred to as SMF1* (or SMF1-star).

Figure 7:
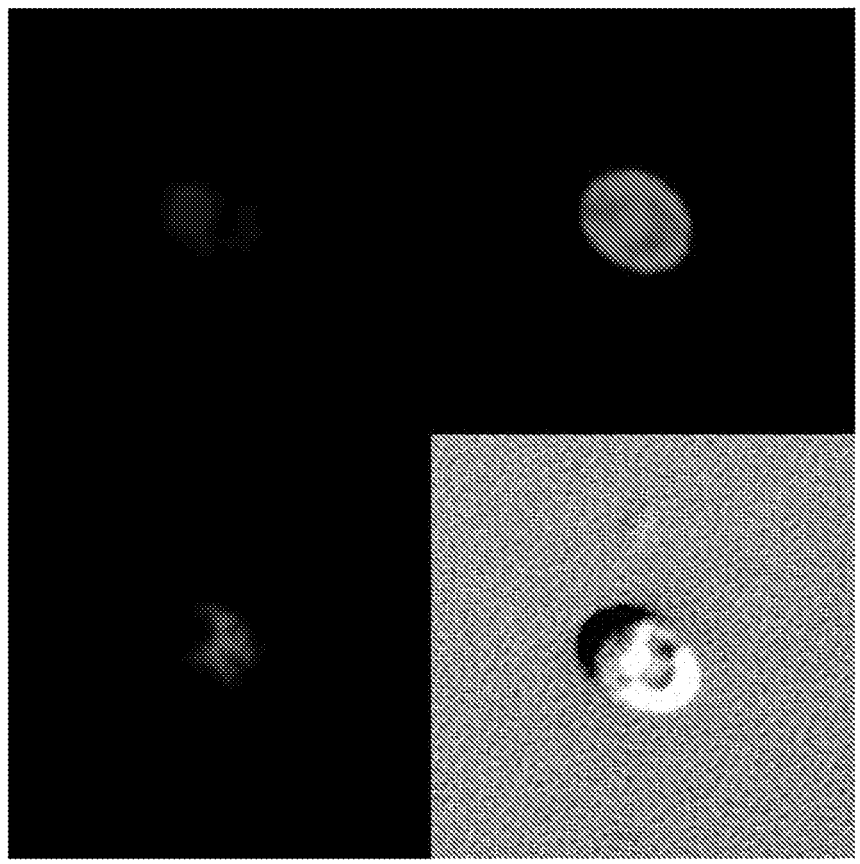
FIG. 7 shows staining of membrane transporter SMF1, and vacuole transporter CCC1.
Figure 8:
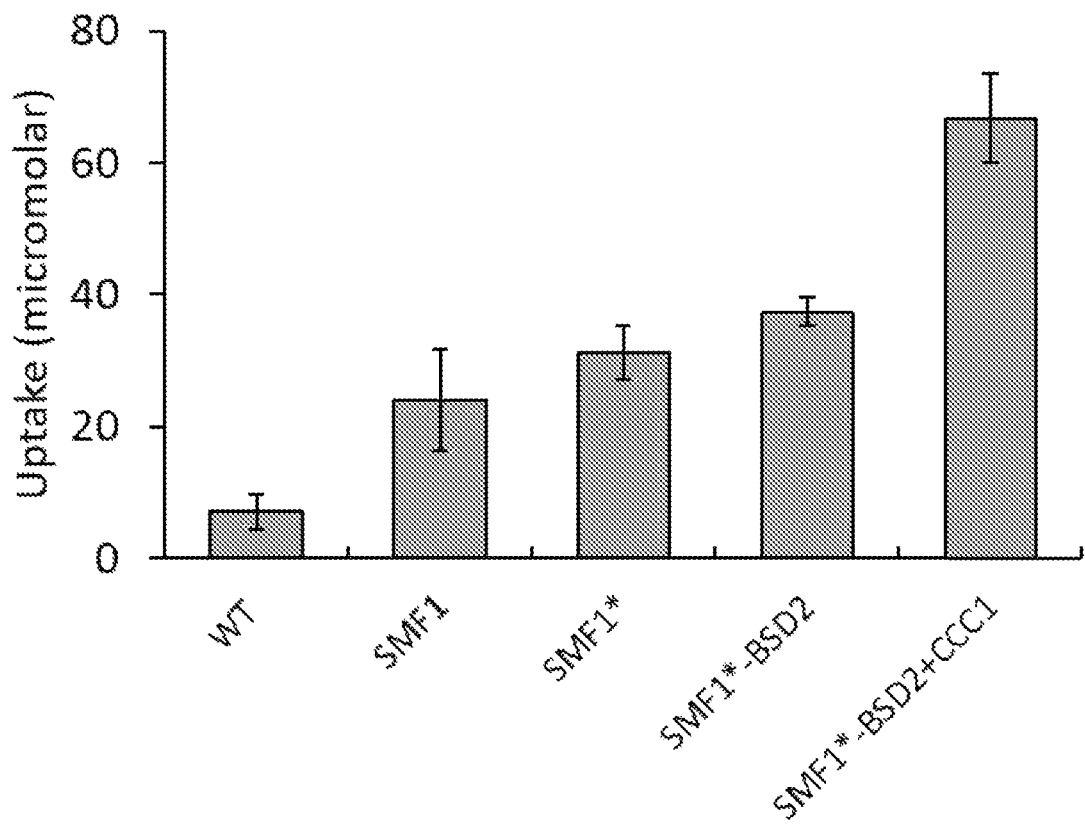
FIG. 8 shows effects on engineering yeast transporters on cadmium uptake.

Finally, a vacuole transporter was chosen by co-expressing selected ones with SMF1* and choosing the vacuole transporter that enhanced the uptake of cadmium. In FIG. 7, blue is DAPI nuclear stain. SMF1 appended with a V5 tag was stained with AlexaFluor 488 (green), and CCC1 appended with a ag tag was stained with AlexFluor 647 (red). The best performing candidate was CCC1, normally a $Fe^{2+}$ and $Mn^{2+}$ transporter, which showed more than 3-fold increase in cadmium uptake (FIG. 8).

2.2. Mutating and Screening of SMF1 for Changes in Metal Specificity and Selectivity One of the biggest limitations to rationally engineering metal transporters is the lack of structural information due to crystallization difficulty and the inability to reconstitute membrane-like environments ex-vivo. See Elisabeth P Carpenter, Konstantinos Beis, Alexander D Cameron, and So Iwata. Overcoming the challenges of membrane protein crystallography. Current opinion in structural biology, 18(5):581-586, 2008, which is incorporated by reference in its entirety. Therefore, most structure-to-function information is obtained via meticulous and often times tedious point mutations in hypothesized residues. Many of these studies have identified significant transmembrane domains, yet most of the results lead to a loss of function. See P Courville, R Chaloupka, and MFM Cellier. Recent progress in structure—function analyses of nramp proton-dependent metal-ion transporters this paper is one of a selection of papers published in this special issue, entitled csbmcbmembrane proteins in health and disease. Biochemistry and Cell Biology, 84(6):960-978, 2006, Steven Lam-Yuk-Tseung, Gregory Govoni, John Forbes, and Philippe Gros. Iron transport by nramp2/dmt1: ph regulation of transport by 2 histidines in transmembrane domain 6. Blood, 101(9):3699-3707, 2003, and J M Argüello. Identification of ion-selectivity determinants in heavy-metal transport p1b-type atpases. The Journal of membrane biology, 195(2):93-108, 2003, each of which is incorporated by reference in its entirety.

Fortunately, SMF1 has significant homology and phylogenetic relationships with a large class of divalent transporters, namely Nramps (natural resistance-associated macrophage proteins) and DMTs (divalent metal transporters). See Ute Kramer, Ina N Talke, and Marc Hanikenne. Transition metal transport. FEBS letters, 581(12):2263-2272, 2007, which is incorporated by reference in its entirety. Because of this, researchers have discovered conserved regions that are necessary for SMF1 function. Through sequence analysis researchers have hypothesized that transmembrane domains 1-4, 5-6, and 9 are responsible for discriminating between and facilitating metal transport.

In order to further narrow the number of significant domains, a global multi-alignment analysis with 81 of the closest ranked members similar to SMF1 was performed. The 81 members were filtered from a potential list of >14,000 sequences queried based on name searches from Uniprot (www.uniprot.org/) by using Clustal Omega (www.ebi.ac.uk/Tools/msa/clustalo/). The 81 members were globally aligned and spans of homology were quantified using Shannon entropy (Equation 1) which is a simple and direct metric for identifying conserved protein regions. See William S J Valdar. Scoring residue conservation. Proteins: structure, function, and bioinformatics, 48(2):227-241, 2002, which is incorporated by reference in its entirety.

$$H(X)_j = \sum_{i=0}^{n} P(x_i) \log_2 P(x_i) \quad (1)$$

Rows of aligned sequences (i) are scored per residue with respects to the queried sequence (j) by calculating the probability (P) of that residue's appearance in the global alignment according to the Shannon entropy function. The lowest entropic score (most conserved) regions were transmembrane domain 1 and 6. Both domains were amplified using error-prone PCR and homologously recombined into SMF1 to generate a library of mutants.

Developing High Throughput Screening of Mutated SMF1 Library

Mutants were screened by subjecting libraries to 100 µM metal ions ($Me^{2+}$) in culture and fractionated based on density changes. Changes in density were used to assess differences in metal uptake, as the uptake of metals imparts additional mass to the cell. See William H Grover, Andrea K Bryan, Monica Diez-Silva, Subra Suresh, John M Higgins, and Scott R Manalis. Measuring single-cell density. Proceedings of the National Academy of Sciences, 108(27):10992-10996, 2011, which is incorporated by reference in its entirety. Cells were separated using density gradient centrifugation; the furthest migrated layers in the density gradient were manually selected, re-plated, sequenced, and quantitatively tested for metal uptake using ICP. These rounds were repeated 3 times for cadmium, and are ongoing for elements such as strontium and lead.

Figure 9:
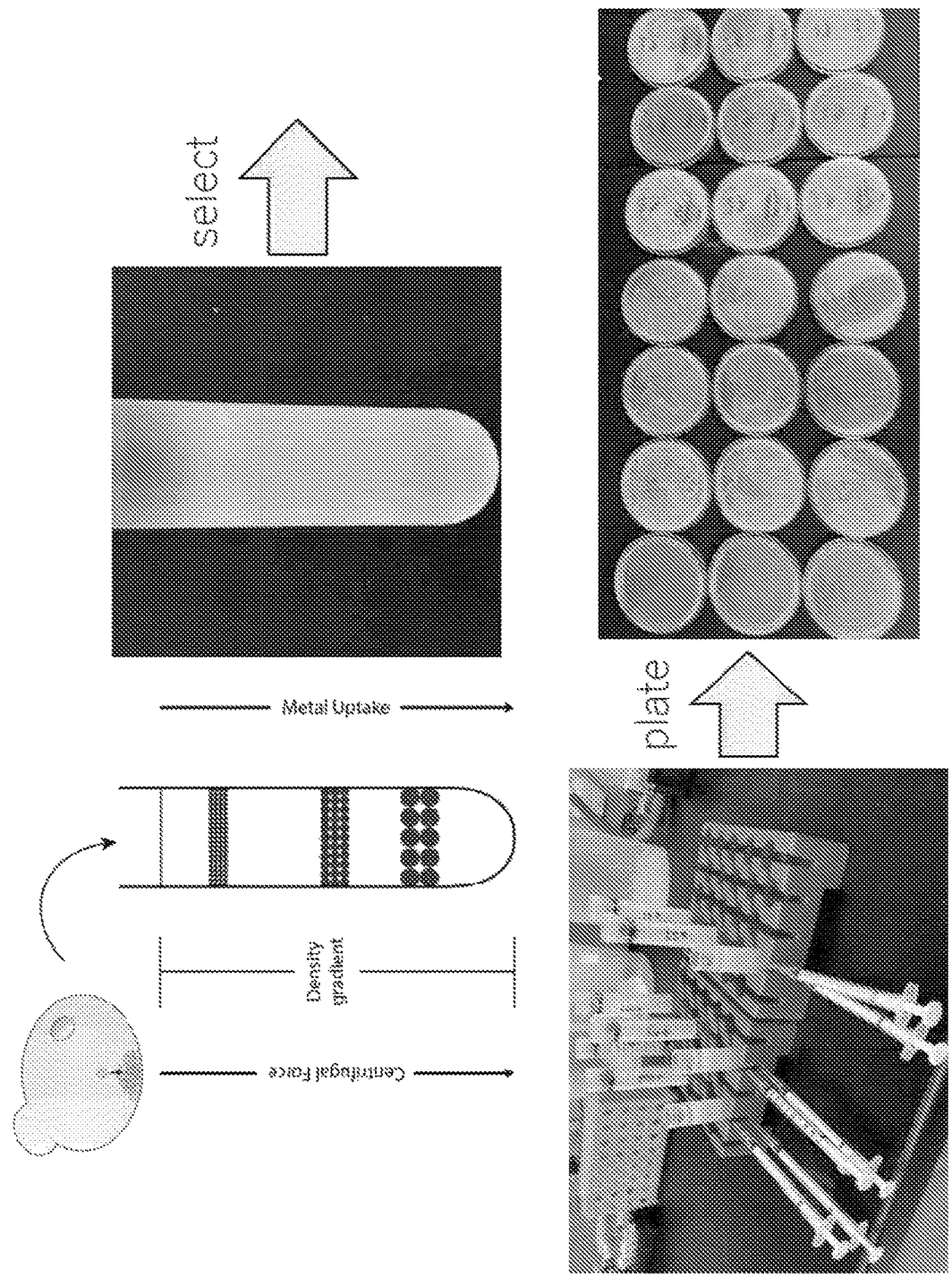
FIG. 9 shows metal transport screening pipeline.

In FIG. 9, SMF1 was mutagenized using error-prone PCR and assayed for metal uptake using density gradient centrifugation. Cells that uptake the most metals migrate furthest to the bottom. Cells were isolated with a syringe, then plated, picked, sequenced, and finally confirmed for metal uptake using ICP.

2.3. Increasing Metal Tolerance & Survival

Figure 10A:
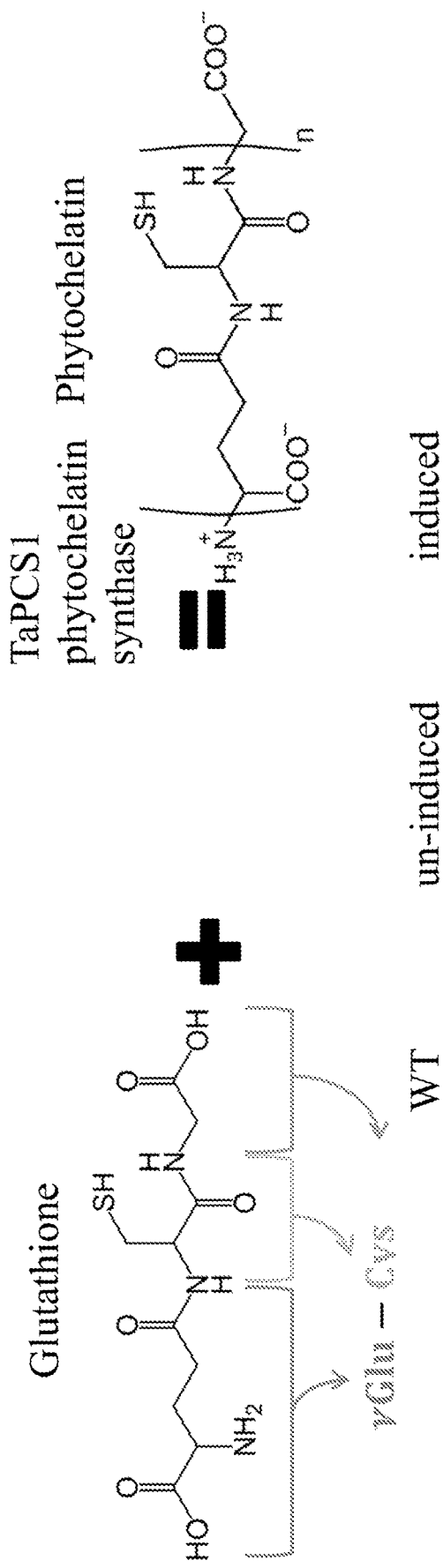
FIG. 10A shows a diagram illustrating plant phytochelatin TaPCS1 to enhance metal tolerance in yeast.
Figure 10A:
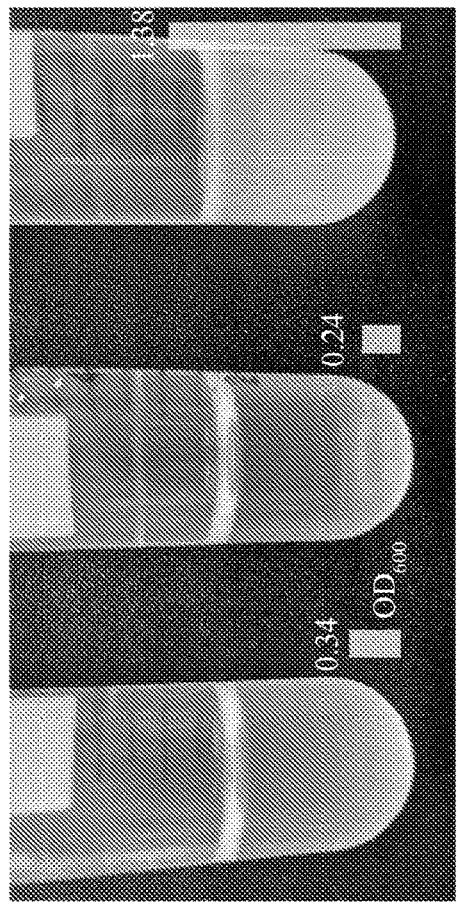
Figure 10B:
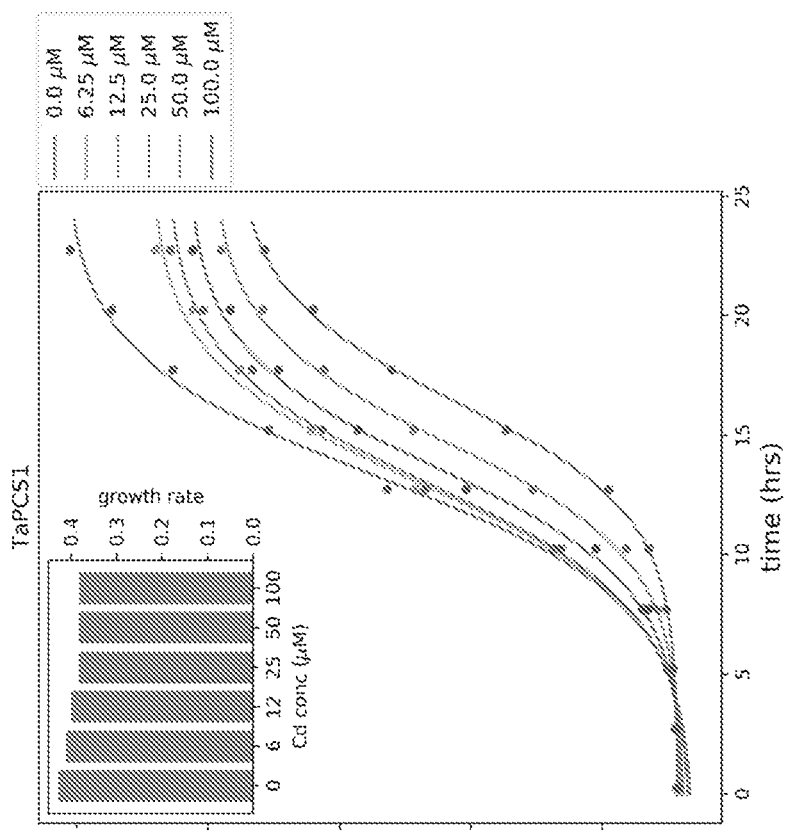
FIG. 10B shows TaPCS1 enhances heavy metal tolerance.
Figure 10B:
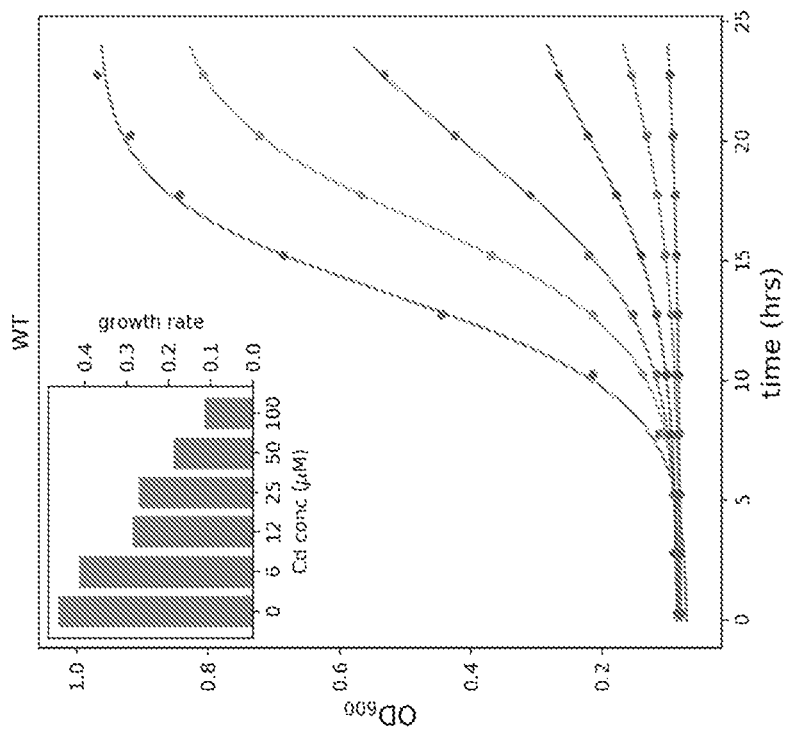
Figure 11:
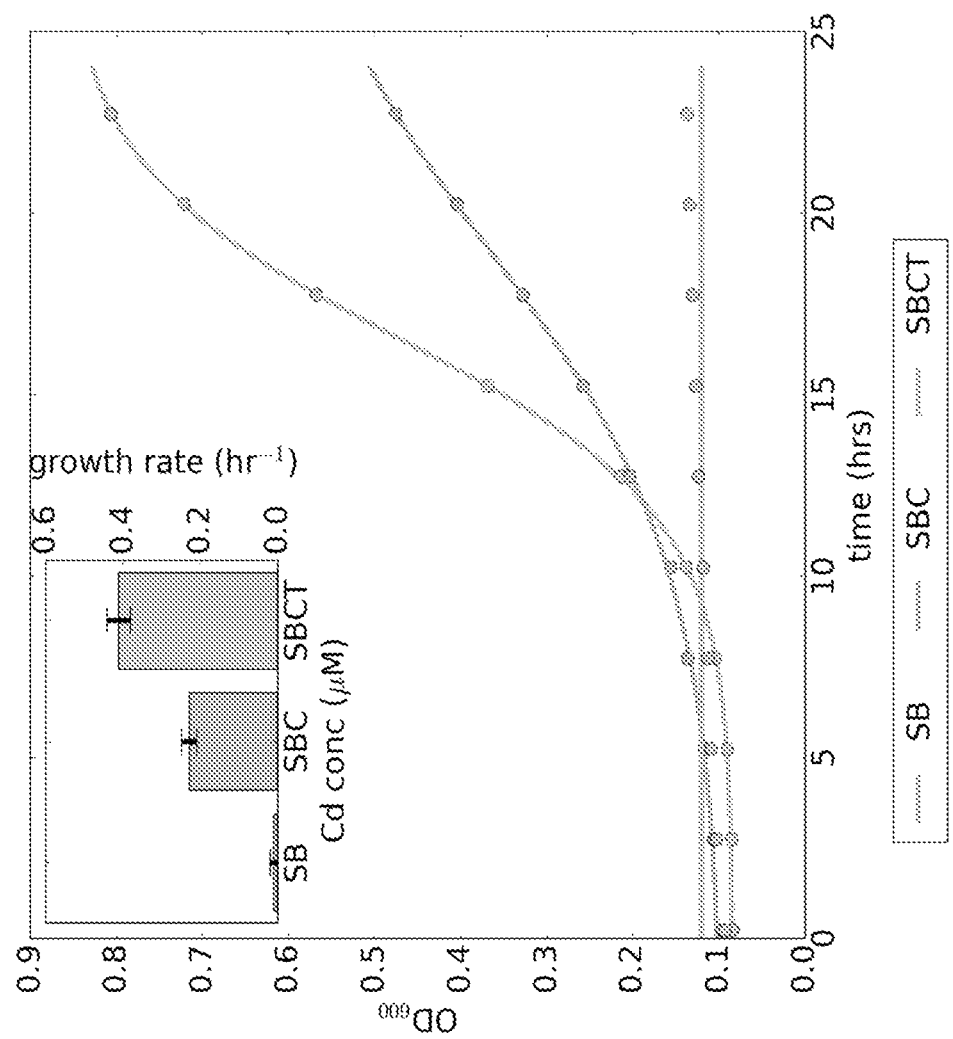
FIG. 11 shows growth curve of engineered strains in 100 µM cadmium.

Along with hyperactive metal transporters, plants can tolerate unusually high metal concentrations by arming themselves with a variety of metal binding proteins, namely glutathiones and metallothioneins. See Christopher Cobbett and Peter Goldsbrough. Phytochelatins and metallothioneins: roles in heavy metal detoxification and homeostasis. Annual review of plant biology, 53(1):159-182, 2002, which is incorporated by reference in its entirety. Plants augment this layer of defense by oligomerizing glutathiones into phytochelatins which act as a network to internalize metals into compartmentalized areas. Id. Clemens et. al. found that a common wheat phytochelatin synthase, TaPCS1, dramatically enhanced metal tolerance when expressed in yeast. See Stephan Clemens, Eugene J Kim, Dieter Neumann, and Julian I Schroeder. Tolerance to toxic metals by a gene family of phytochelatin synthases from plants and yeast. The EMBO journal, 18(12):3325-3333, 1999, which is incorporated by reference in its entirety. Performing a similar experiment, a constitutive overexpression of TaPCS1 directly cloned from wheat to wild-type yeast improved cadmium tolerance by almost (FIGS. 10A-10B). FIG. 10A shows a diagram illustrating plant phytochelatin TaPCS1 to enhance metal tolerance I yeast. See Clemens, S., Kim, E. J., Neumann, D. & Schroeder, J. I. Tolerance to toxic metals by a gene family of phytochelatin synthases from plants and yeast. The EMBO Journal 18,3325-3333 (1999), which is incorporated by reference in its entirety. In FIG. cultures were grown in increasing amounts of cadmium levels (0-100 µM) and measured periodically at OD600. Growth rate k were extracted from curves using the logistic growth function. The left figure are wild-type yeast, the right figure are wild-type yeast constitutively expressing wheat phytochelatin synthase TaPCS1.

2.4. Additional Embodiments

In certain embodiments, SMF1 transporters can be created to be selective not only to cadmium, but also for additional metals such as strontium, lead, mercury, etc. by focusing on filtering out libraries of SMF1 mutants based on increase metal uptake, metal selectivity (KD) and specificity between metals. For example, interference experiments can determine whether mutants can uptake cadmium in the presence of excess manganese (the preferred metal). Likewise, an experiment for metal selectivity can be executed to characterize titration curves in order to determine the KD response of a given metal using colorimetric assays or ICP.

Uptake of Negatively Charged Metal Compounds

Not all heavy metals are positively charged, there exist polyatomic metal compounds in the negative state such as chromate ($CrO_4^{2-}$) and arsenate ($AsO_4^{2-}$) which are acutely toxic, however unrecognized by SMF1. See AD Dayan and AJ Paine. Mechanisms of chromium toxicity, carcinogenicity and allergenicity: review of the literature from 1985 to 2000. Human & experimental toxicology, 20(9):439-451, 2001, and Michael F Hughes. Arsenic toxicity and potential mechanisms of action. Toxicology letters, 133(1):1-16, 2002, each of which is incorporated by reference in its entirety. Yet, there exist permeases, much like metal transporters, that facilitate the flux of basic nutrients such as sulfates ($SO_4^{3-}$) and phosphates ($PO_4^{2-}$) into the cell. See Bruno André. An overview of membrane transport proteins in *Saccharomyces cerevisiae*. Yeast, 11(16):1575-1611, 1995, which is incorporated by reference in its entirety.

Figure 12A:
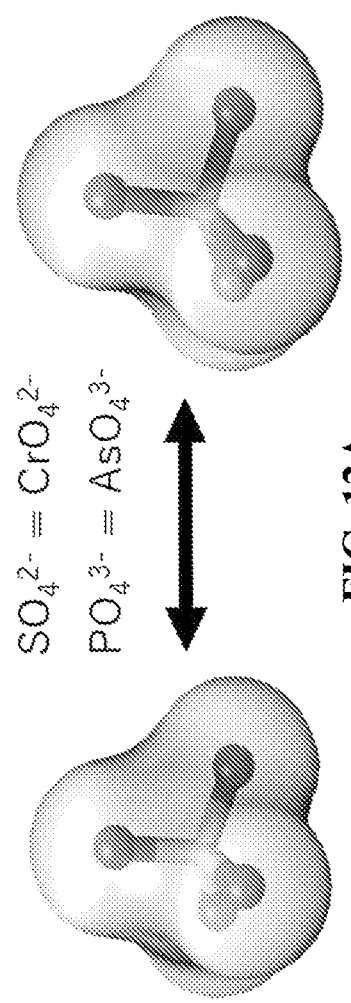
FIGS. 12A-12B show using sulfate permeases to uptake structurally similar chromate ions.
Figure 12B:
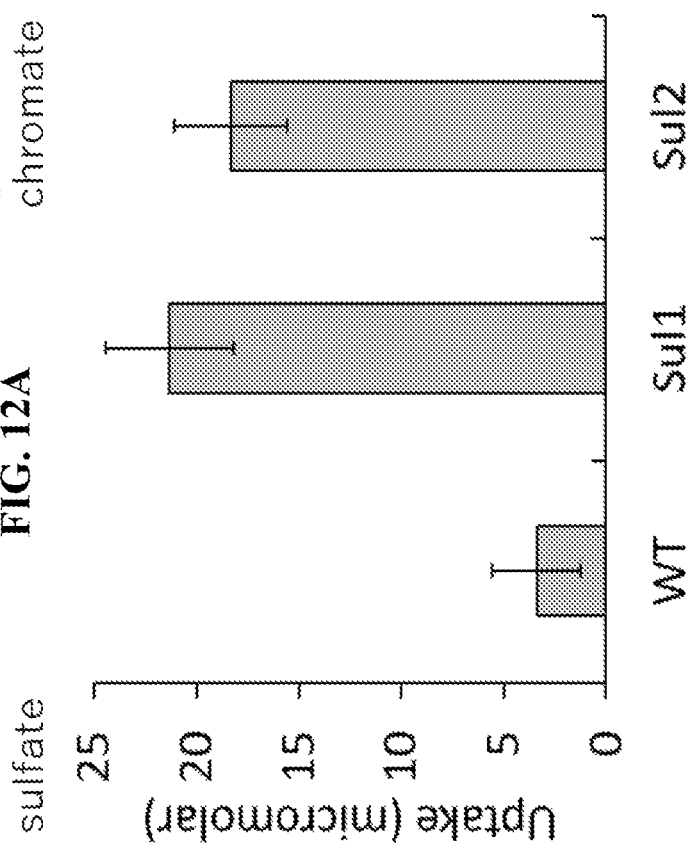
Figure 13A:
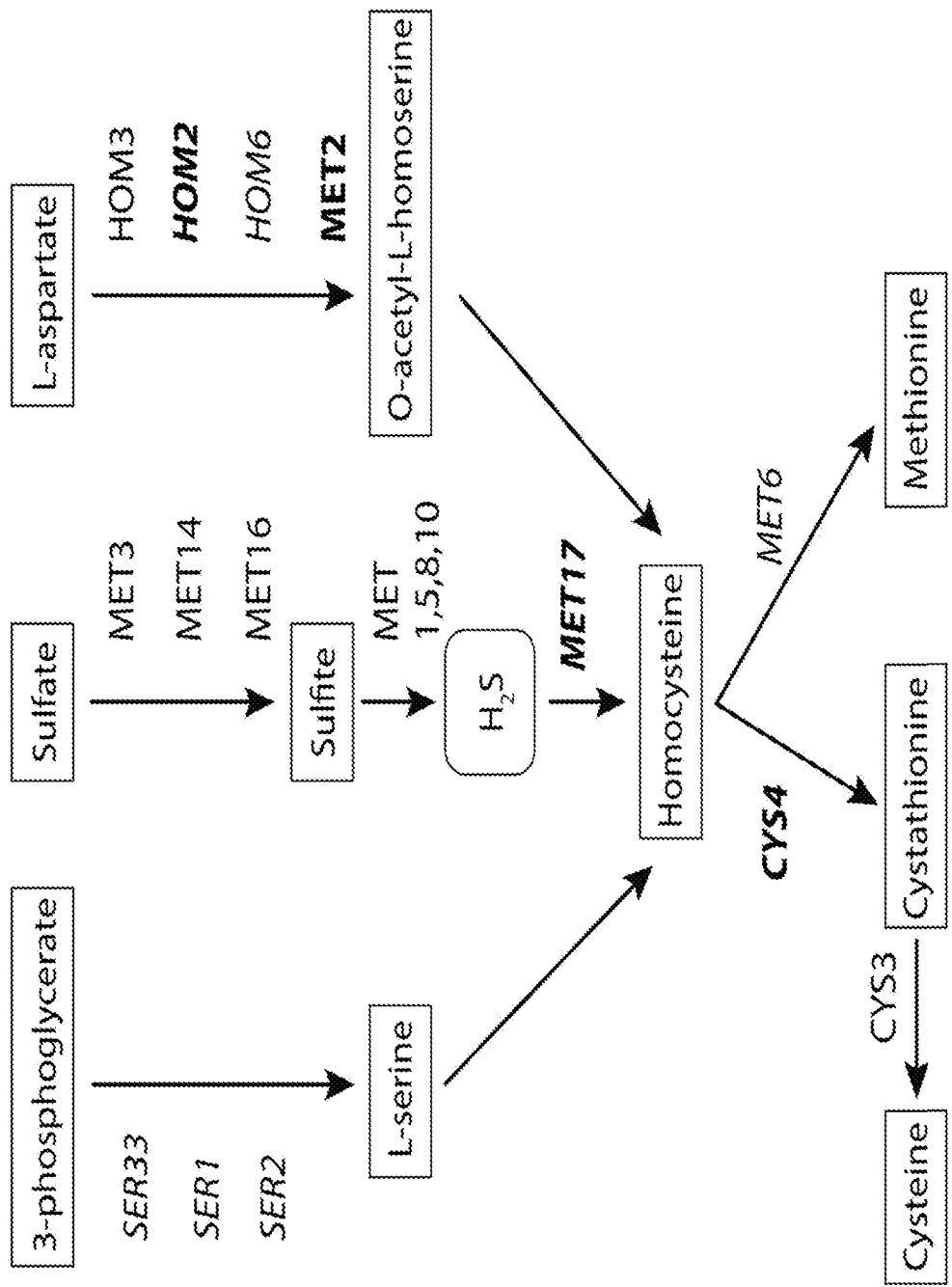
FIG. 13A shows simplified diagram of yeast's sulfur pathway.
Figure 13B:
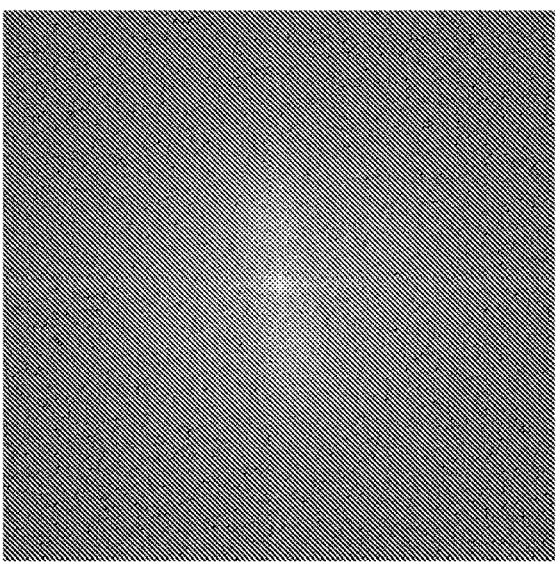
FIG. 13B shows crystalline metal sulfide particles (e.g. PbS) using ΔCYS4 strain.
Figure 13B:
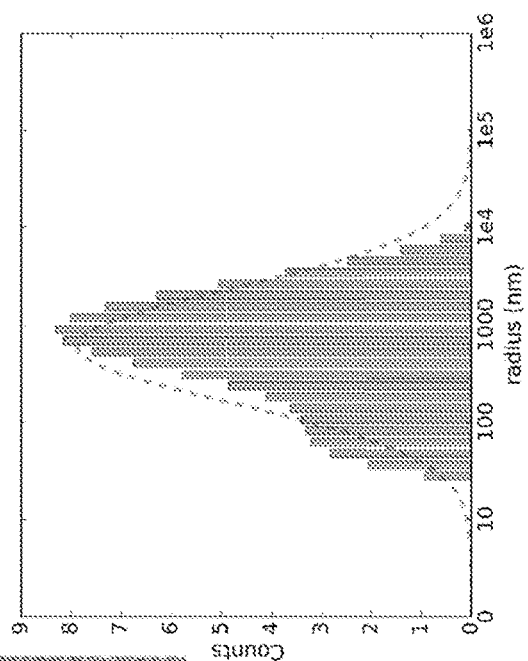
Figure 13B:
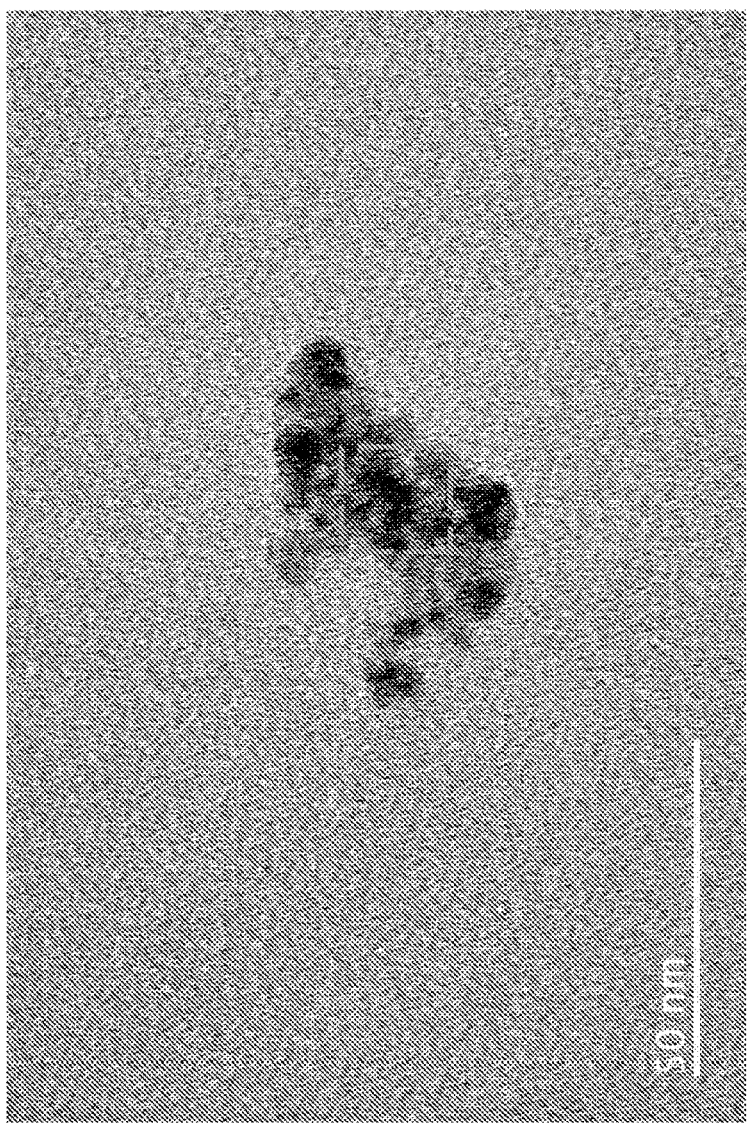
Figure 13C:
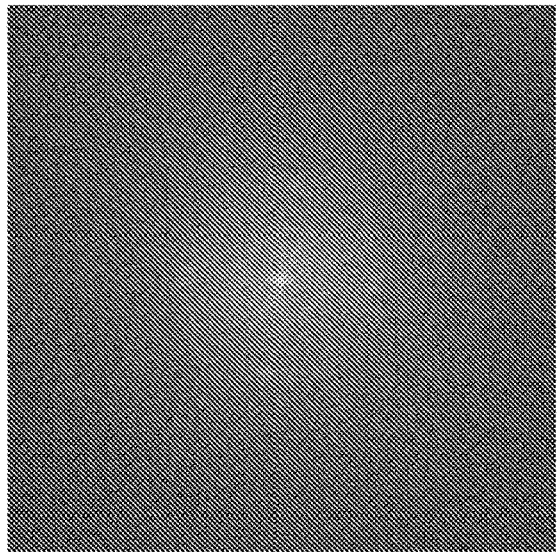
FIG. 13C shows crystalline metal sulfide particles (e.g. PbS) using ΔHOM2.
Figure 13C:
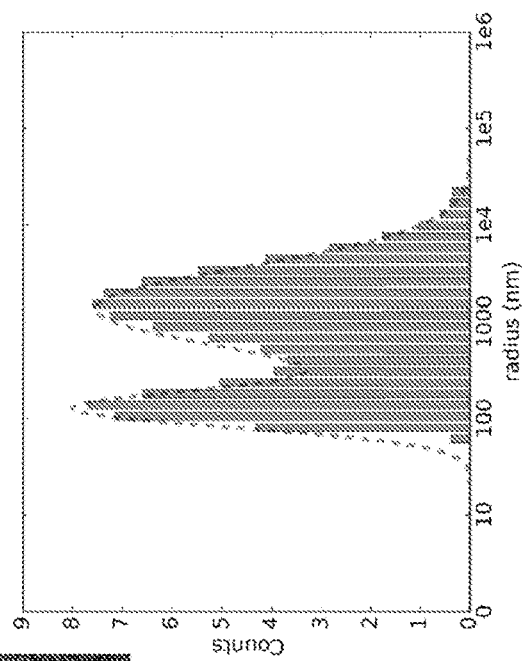
Figure 13C:
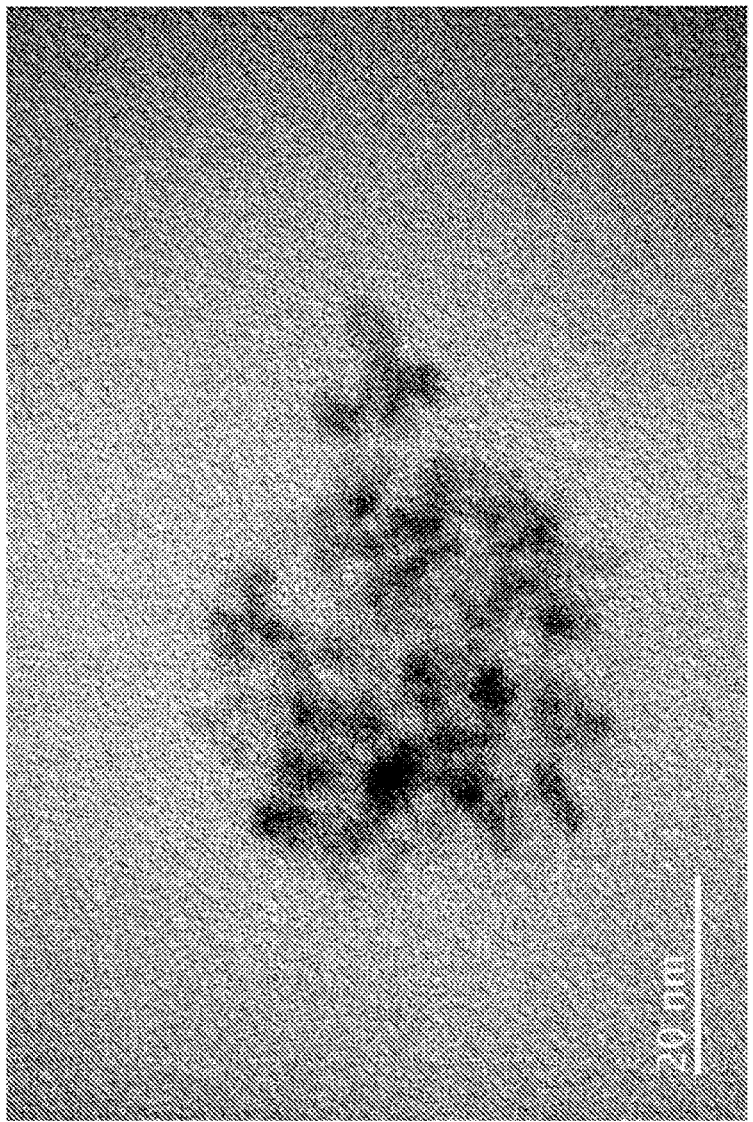
Figure 13D:
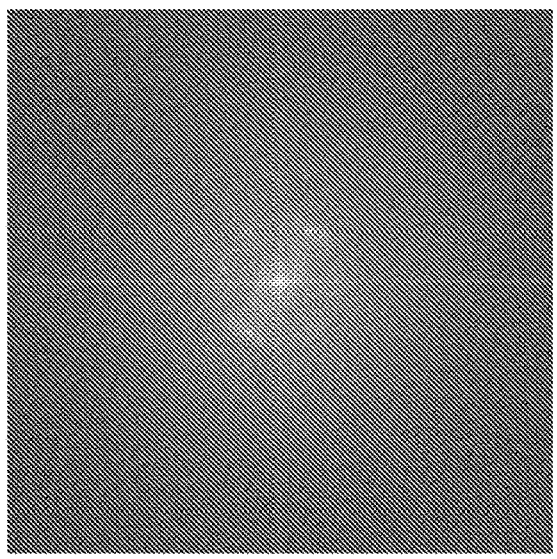
FIG. 13D shows crystalline metal sulfide particles (e.g. PbS) using ΔMET17.
Figure 13D:
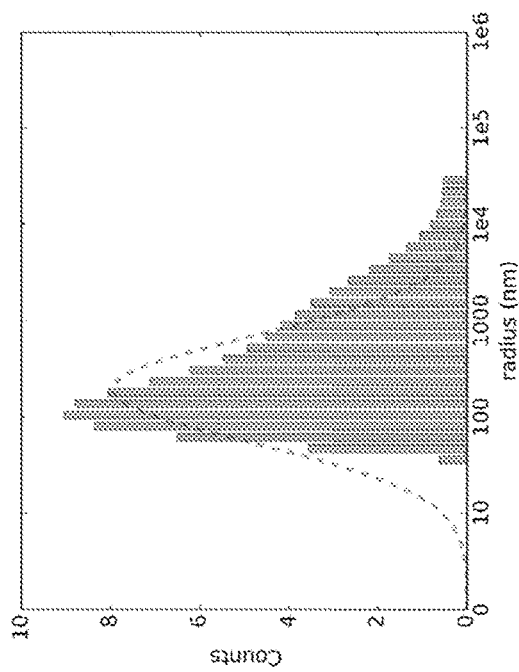
Figure 13D:
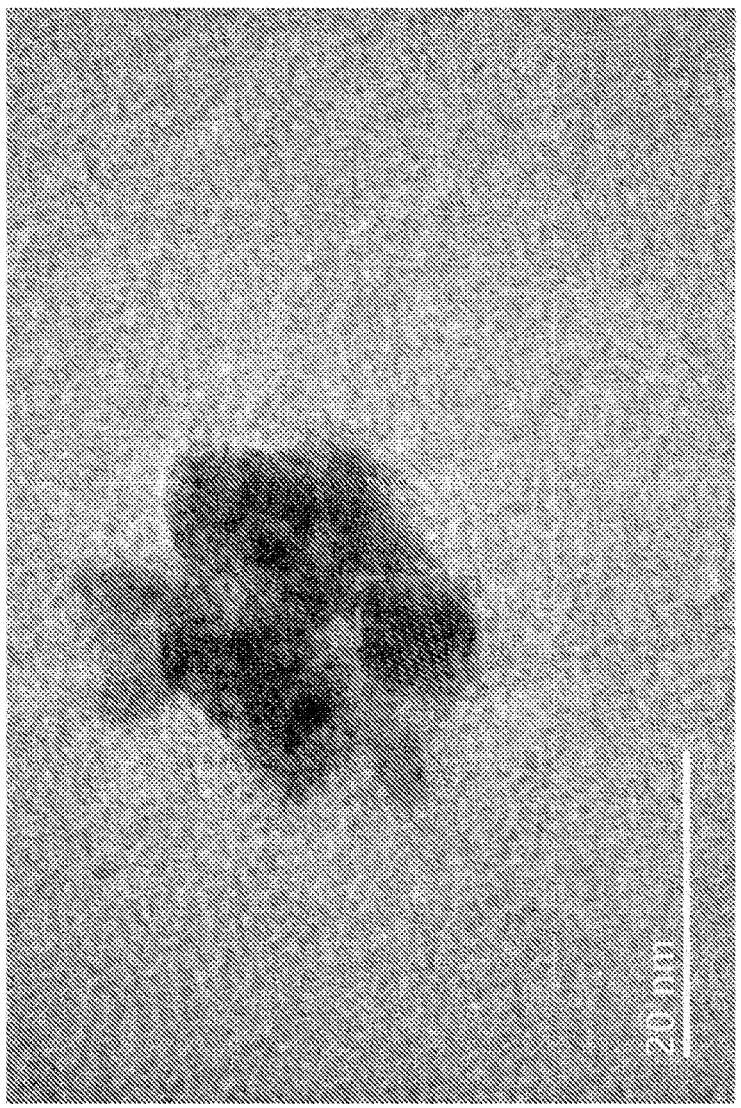
Figure 13E:
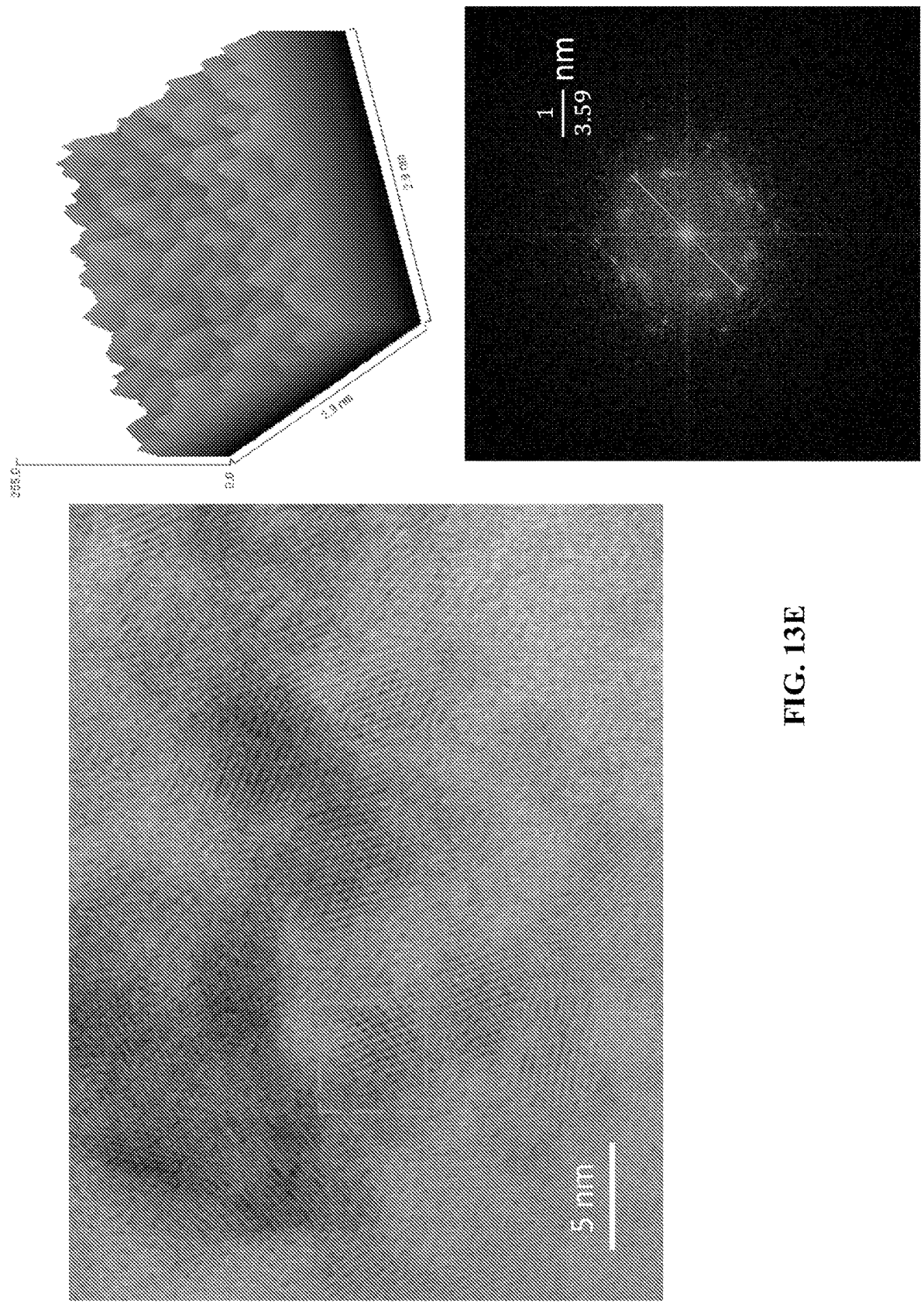
FIG. 13E shows a deeper look of the particles.
Figure 13F:
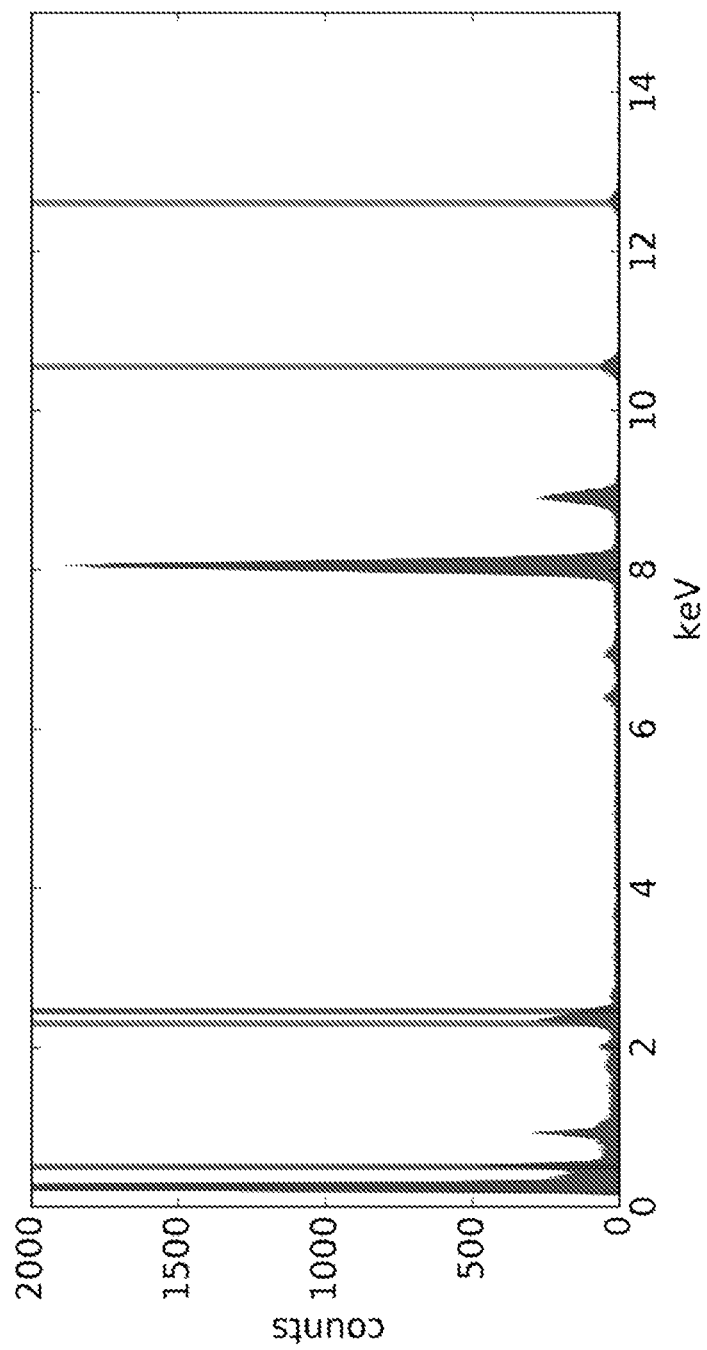
FIG. 13F shows EDX—ratiometric analysis of the metal sulfide particles.
Figure 13G:
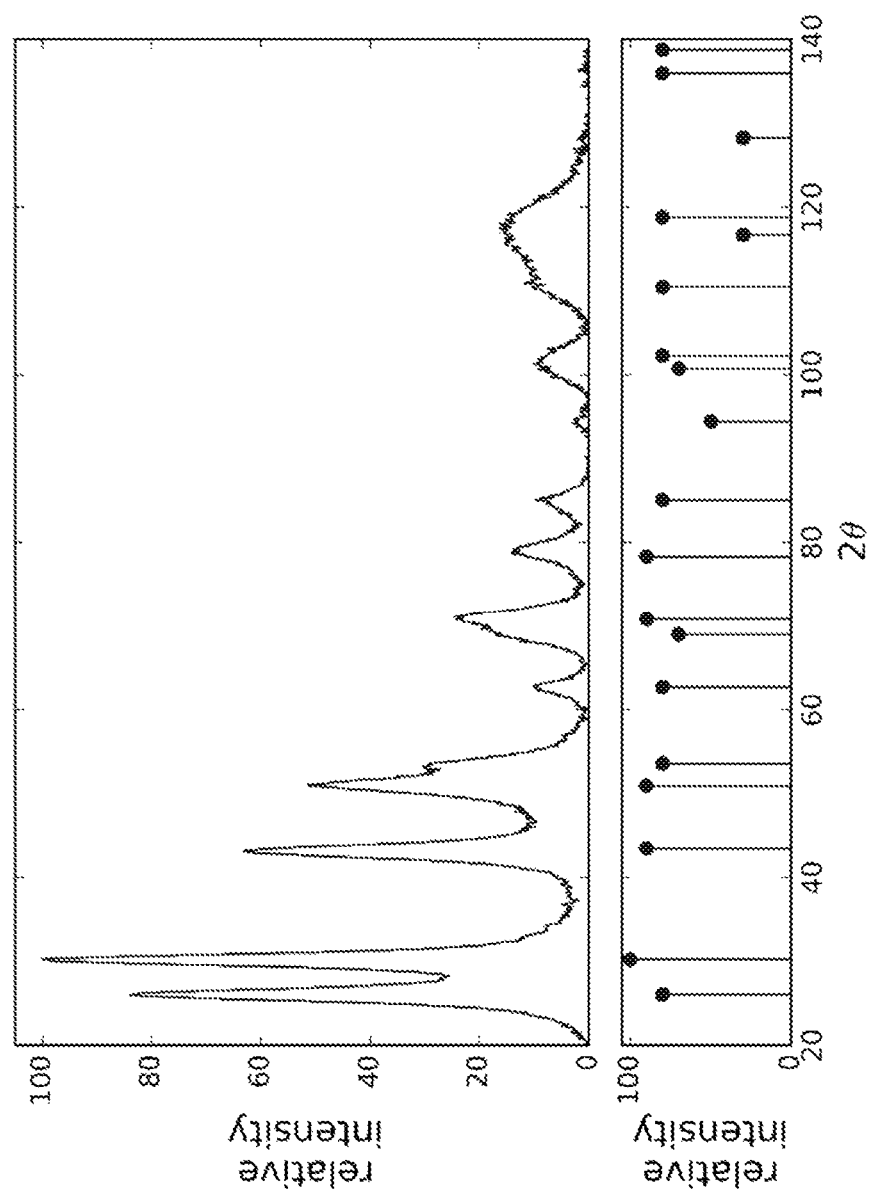
FIG. 13G shows XRD—material crystallinity of the metal sulfide particles.

Given the structural similarity between chromates and sulfates, and between arsenates and phosphates (FIGS. 12A-12B), it may be possible to "hijack" these permeases for chromate and arsenate uptake. As a preliminary experiment, both sulfate permeases Sul1, and Sul2 were tested for chromate uptake. As hypothesized, chromate uptake was elevated in yeast expressing Sul1, Sul2, but not to the degree at which overexpressing wild-type SMF1 uptakes divalent metals. One explanation is that chromate is much more acutely toxic than cadmium; at concentrations above 20 µM yeast die and no longer transport metals. Another explanation is that permeases are selective enough to discern between sulfates and chromates. Or perhaps the sulfate concentration in yeast media overwhelms the transport of chromate.

Applications in Mining

Admittedly, cellular uptake of heavy metals has the least per cell uptake capacity ratio than Strategy 1. However, a main advantage of metal transporters is that they are more sensitive to low amounts of metals, and are more metal specific. Besides SMF1, there exist other selective metal transporters such as CTR1 (copper), ZRT1 (zinc), and FRE1 (iron). These transporters are able to recognize and uptake µM to nM amounts of metals despite the presence of other more concentrated ions such as sodium and calcium naturally found in growth media. See Stephan Clemens, Michael G Palmgren, and Ute Kramer. A long way ahead: understanding and engineering plant metal accumulation. Trends in plant science, 7(7):309-315, 2002, which is incorporated by reference in its entirety. This metal specific uptake can be capitalized to mine useful metals from waste water in addition to providing a mechanism for metal removal. With the growing demand of electronically relevant metals such as lithium, noble metals (gold, silver, platinum), and rare-earth metals, mining operations are becoming exceedingly more dangerous and harmful to the environment. See Gavin Hilson. Pollution prevention and cleaner production in the mining industry: an analysis of current issues. Journal of Cleaner Production, 8(2):119-126, 2000, which is incorporated by reference in its entirety. Likewise, metal extraction typically takes several rounds of heating and smelting to purify a single element, which is labor intensive and costly. See Jirang Cui and Lifeng Zhang. Metallurgical recovery of metals from electronic waste: A review. Journal of hazardous materials, 158(2):228-256, 2008, and AM Alfantazi and RR Moskalyk. Processing of indium: a review. Minerals Engineering, 16(8):687-694, 2003, each of which is incorporated by reference in its entirety. Given these limitations it may be possible to engineer yeast with specialized metal transporters to act as mining agents that harvest and concentrate scarce amounts of metals from environmental sources under ambient conditions.

One example would be mining for lithium, noble metals (such as gold, silver, platinum) and rare-earth metals (such as cerium (Ce), dysprosium (Dy), erbium (Er), europium (Eu), gadolinium (Gd), holmium (Ho), lanthanum (La), lutetium (Lu), neodymium (Nd), praseodymium (Pr), promethium (Pm), samarium (Sm), scandium (Sc), terbium (Tb), thulium (Tm), ytterbium (Yb) or yttrium (Y)). A report by MIT projects that lithium shortages will occur by 2050, yet some researchers acknowledge that this can be avoided if the ocean were mined instead. See Richard Martin, As Demand for Lithium Grows, the Race to Extract It Intensifies, 2015, which is incorporated by reference in its entirety. Despite an overall massive quantity, approximately 1.5 trillion tons, lithium concentrations are low, ranging from 0.1-1 ppm (sub micromolar), and differentiating between the more abundant salt content makes lithium mining almost impossible. See Ernest E Angino and Gale K Billings. Lithium content of sea water by atomic absorption spectrometry. Geochimica et Cosmochimica Acta, 30(2):153-158, 1966, which is incorporated by reference in its entirety. A similar situation poses a challenge for rare-earth mining. Ironically, some rare-earths are more abundant than more known elements such as cobalt and manganese, yet they are typically difficult to extract because of the overwhelming presence of iron, copper, and nickel compounds in mining ores. See Xiaoyue Du and Thomas E Graedel. Global in-use stocks of the rare earth elements: a first estimate. Environmental science & technology, 45(9):4096-4101, 2011, which is incorporated by reference in its entirety. Again, highly specific yeast transporters could help differentiate rare-earths from other elements and aid in the mining process. Yeast can effectively act as concentrators, specializing and storing desired metals of interest. Yeast can then be harvested and lysed to obtain the stored metal. Afterwards, simpler and more straightforward physicochemical techniques can be used to isolate and purify these metals rather than having to smelt and reheat ores common of traditional methods.

3. Strategy 3—Metal Conversion

The type of metal as well as its electronic state are equally important in determining the metals' toxicity. For example, Cr(VI) is highly mutagenic and acutely toxic, whereas Cr(III) readily forms stable oxides and precipitates out of solution. See Olga Muter, Aloizijs Patmalnieks, and Alexander Rapoport. Interrelations of the yeast *Candida utilis* and cr (vi): metal reduction and its distribution in the cell and medium. Process Biochemistry, 36(10):963-970, 2001, which is incorporated by reference in its entirety. Therefore, it is just as important to convert metals to more benign electronic states as it is to capture and remove them from waste waters. However, what has limited bio-facilitated conversion and reactions of heavy metals is the burden of supplying electron-rich molecules (e.g. pyruvates and NADP(H)s), which are themselves rarely free in the cell other than for highly regulated biological processes. Even if these biomolecules are present, the electrons must overcome a large activation barrier for converting normally stable metal ions to a more benign state.

3.1. Encouraging Sulfur Production in Yeast

Normally, cells are unable to process large amounts of metals from the environment; however, there exist a unique class of archaebacteria that can convert a select set of metals and organic compounds to other electronic states (e.g. $Fe^{2+} \leftrightarrow Fe^{3+}$) for metabolic purposes. See Derek R Lovley. Dissimilatory metal reduction. Annual Reviews in Microbiology, 47(1):263-290, 1993, and Karrie A Weber, Laurie A Achenbach, and John D Coates. Microorganisms pumping iron: anaerobic microbial iron oxidation and reduction. Nature Reviews Microbiology, 4(10):752-764, 2006, each of which is incorporated by reference in its entirety. For example, a class of bacteria, known as sulfate-reducins, obtains energy by reducing sulfate ($SO_4^{2-}$) to hydrogen sulfide ($H_2S$), and in the process gain energetic electrons for other cellular functions. Because of the production of hydrogen sulfide, these sulfate-reducins are able to erode iron and copper comprised rocks, and have unfortunately become a hazard to old concrete and metal infrastructures due to accelerated sulfur corrosion. See Washington A Hamilton. Sulphate-reducing bacteria and anaerobic corrosion. Annual Reviews in Microbiology, 39(1):195-217, 1985, which is incorporated by reference in its entirety. However researchers have deliberately used this phenomenon to remove rusted metals from old mines and drains for cleaning purposes. See C Garcia, DA Moreno, A Ballester, ML Blazquez, and F Gonzalez. Bioremediation of an industrial acid mine water by metal-tolerant sulphate-reducing bacteria. Minerals Engineering, 14(9):997-1008, 2001, which is incorporated by reference in its entirety. Given what is known about the scarcity of electron rich species in the cell, sulfur lends itself extremely well as a metal reactant that is biologically generated. If production can be controlled, sulfur could be utilized as a reliable source for heavy metal remediation.

Effects of Knockouts

Rather than using a difficult-to-culture sulfur-reducin, Strategy 3 is focused on creating sulfur-producing yeast. Surprisingly, the wine industry has studied the effects of yeast related-sulfur production with respect to wine quality. For the past century, winemakers have realized that over-fermentation, or failing to supply sufficient nutrient sources, causes yeast to produce a pungent smell during wine-making. See Carla S Thomas, Roger B Boulton, Michael W Silacci, and W Douglas Gubler. The effect of elemental sulfur, yeast strain, and fermentation medium on hydrogen sulfide production during fermentation. American journal of enology and viticulture, 44(2):211-216, 1993, which is incorporated by reference in its entirety. With the aid of recent molecular biology techniques, researchers have discovered that due to extreme culture conditions essential proteins in the sulfate reducing pathway are either inhibited or denatured causing a buildup of sulfide ($H^{2-}$) precursors. See JH Swiegers and IS Pretorius. Modulation of volatile sulfur compounds by wine yeast. Applied Microbiology and Biotechnology, 74(5):954-960, 2007, which is incorporated by reference in its entirety.

Figure 15B:
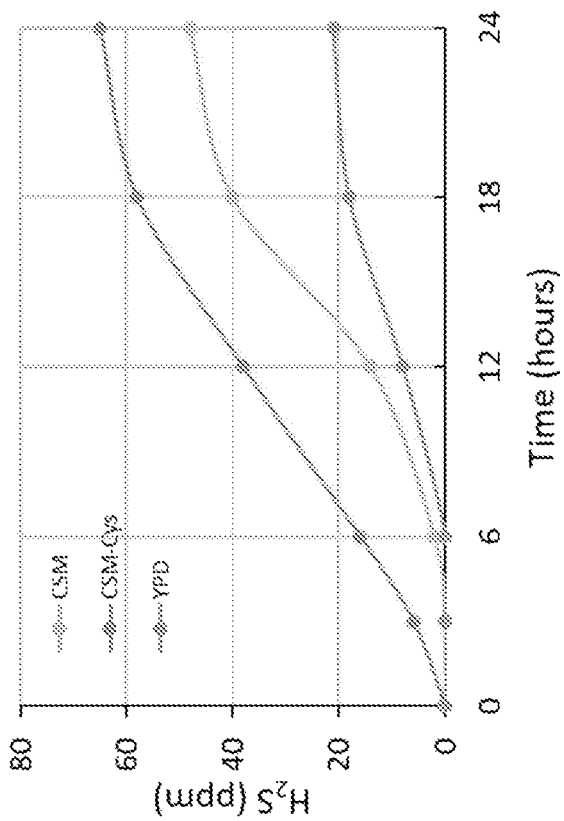
FIGS. 15A-15C show the effects of media condition on sulfide production.
Figure 15A:
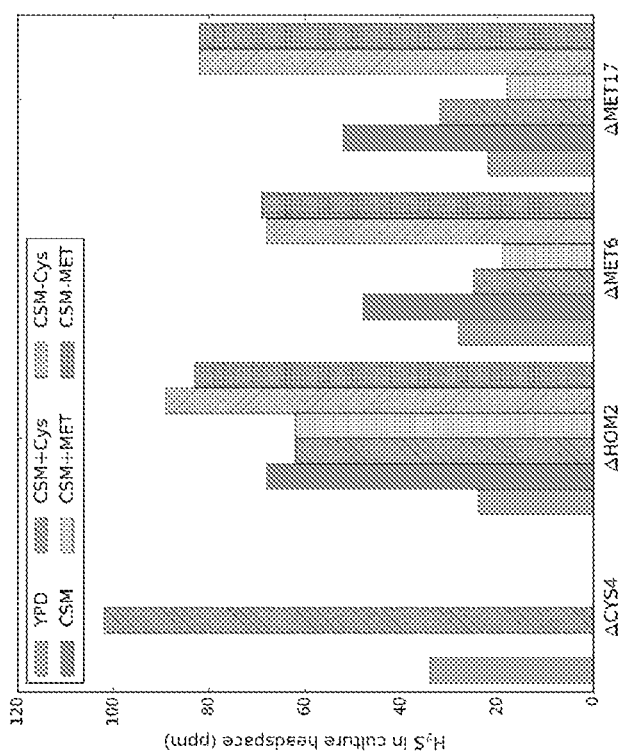

Enzymes in the sulfate assimilation pathway were knocked out to force a buildup of H2S (FIGS. 13A-13G). In FIGS. 13A-13G, italicized enzymes were knocked out and screened for sulfur production. Italicized and bolded enzymes are knockouts that produced a detectable amount of sulfur. All others are necessary enzymes that are required for sulfur metabolism. See Angela L Linderholm, Carrie L Findleton, Gagandeep Kumar, Yeun Hong, and Linda F Bisson. Identification of genes affecting hydrogen sulfide formation in *Saccharomyces cerevisiae*. Applied and environmental microbiology, 74(5):1418-1427, 2008, Chien Huang, Miguel Roncoroni, and Richard C Gardner. Met2 affects production of hydrogen sulfide during wine fermentation. Applied microbiology and biotechnology, 98(16): 7125-7135, 2014, and Chien-Wei Huang, Michelle E Walker, Bruno Fedrizzi, Miguel Roncoroni, Richard C Gardner, and Vladimir Jiranek. The yeast turn1 affects production of hydrogen sulfide from cysteine treatment during fermentation. FEMS yeast research, 16(8), 2016, each of which is incorporated by reference in its entirety. Knockouts such as ΔMET2,17 and ΔHOM2 produced an observable amount of sulfur determined by lead acetate strip and sulfur-displacement columns (FIG. 15A), whereas some deletions such as ΔCYS4 and ΔSER1,2 produced cysteine and methionine auxotrophy. Multi-deletions (2 & 3 knockouts) produced sick strains that barely formed colonies even on YPD (yeast peptone dextrose media), and therefore were not tested.

Effects of Media Composition and Nutrients

Figures 32A, 32B:
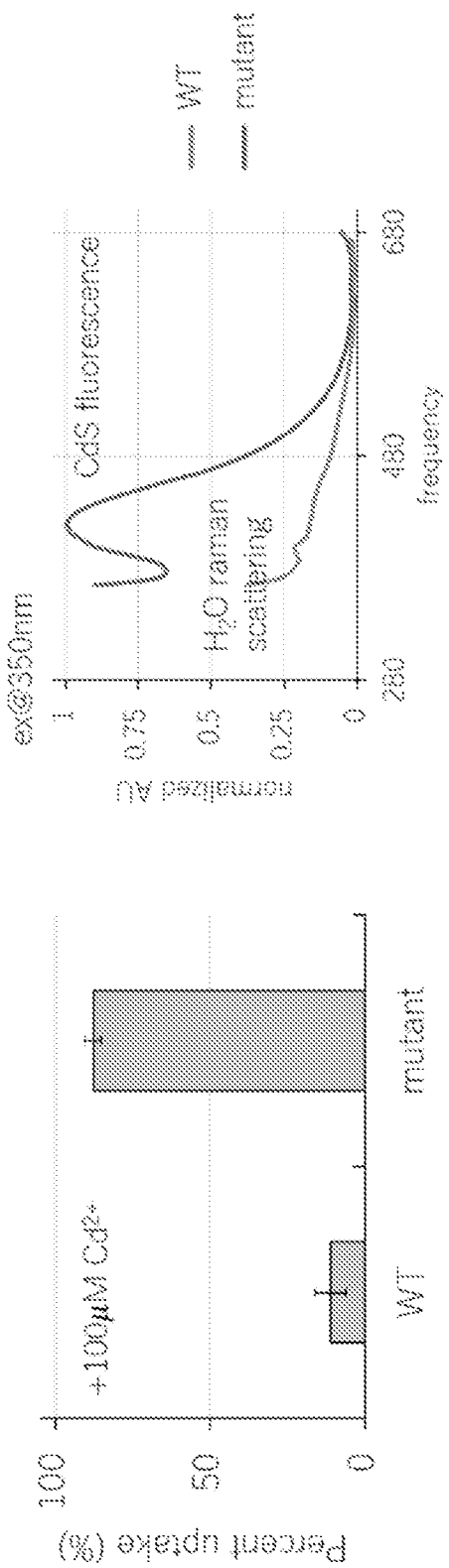
FIGS. 32A-32B show that yeast can generate sulfur to precipitate metals out of solution.

The size and crystal properties of these nanoparticles can be tuned by changing the nutritional content of the yeast culture, primarily cysteine and methionine precursors, thereby changing the production rate and timing of sulfur, which ultimately effects the kinetics of particle growth. More so, if these particles are properly made, they also have fluorescent properties (FIG. 32B), which makes production of these complex particles autonomous, tunable, and cheap.

Figure 14:
FIG. 14 shows lead acetate strips (left) turn black in the presence of gaseous sulfur.
Figure 14:
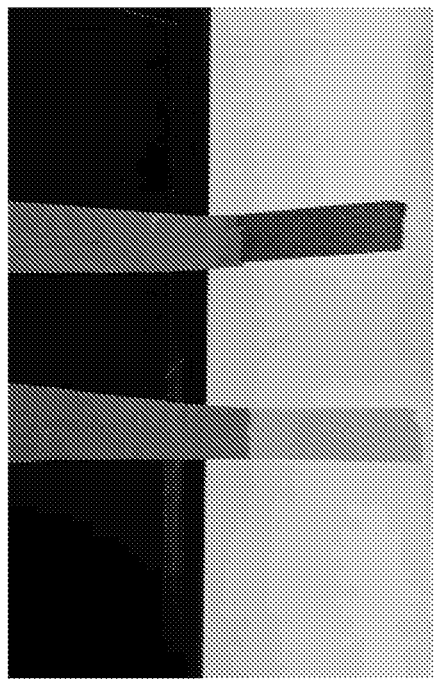

FIG. 14 shows a more quantitative detection method is to use columns that change color at a given height as a function of sulfur production. Rich culture sources such as YPD allowed all knockouts to grow, yet some produced little-to-no sulfide. Compared to CSM media (complete supplement mixture, which lacks cysteine and contains minimal methionine), ΔMET2,17 and ΔHOM2 produced sulfide at levels up to 100 ppm (FIG. 15A); however mutants such as ΔCYS4 and ΔSER1,2 failed to grow due to cysteine or methionine auxotrophy.

Figure 15C:
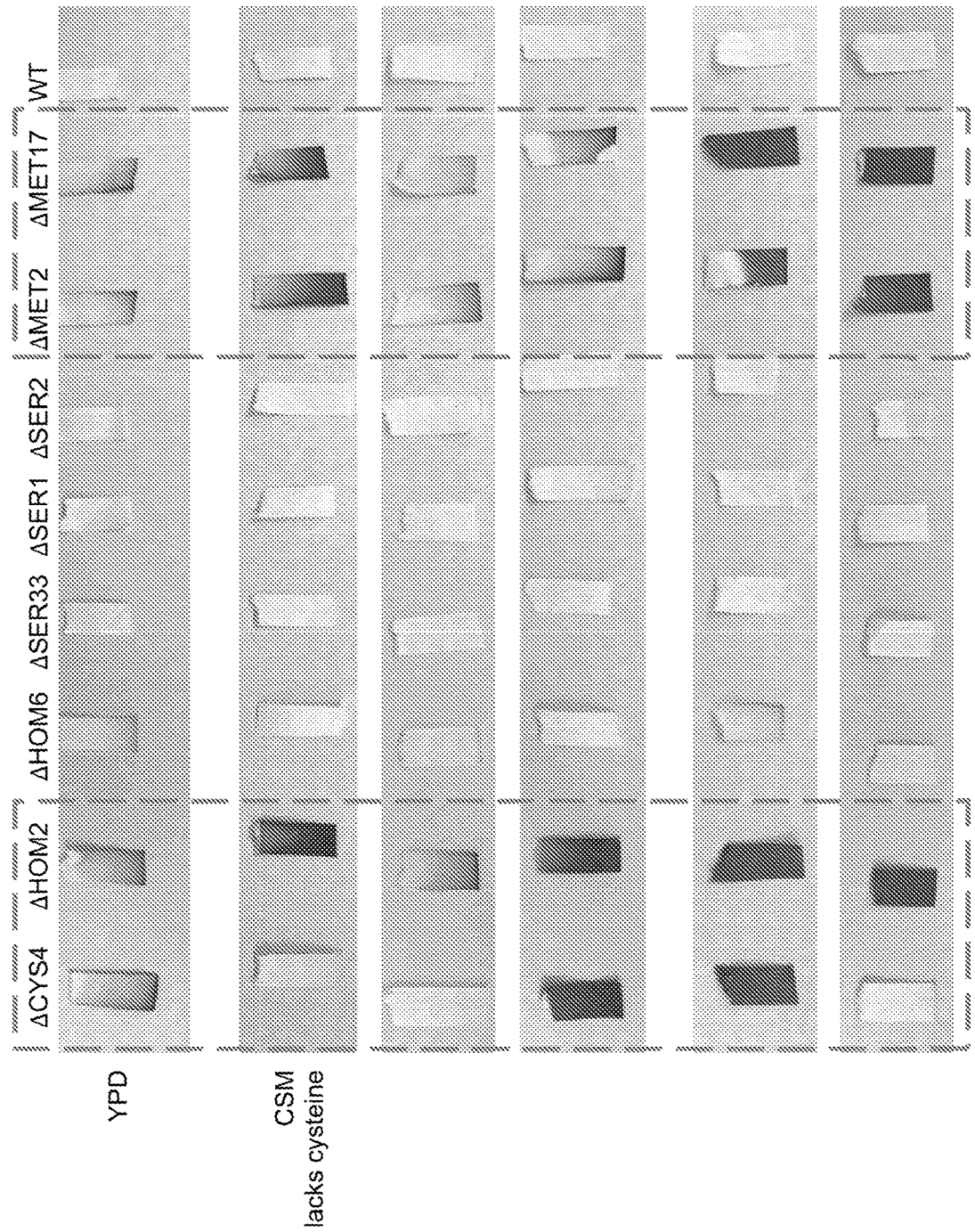
Figure 16A:
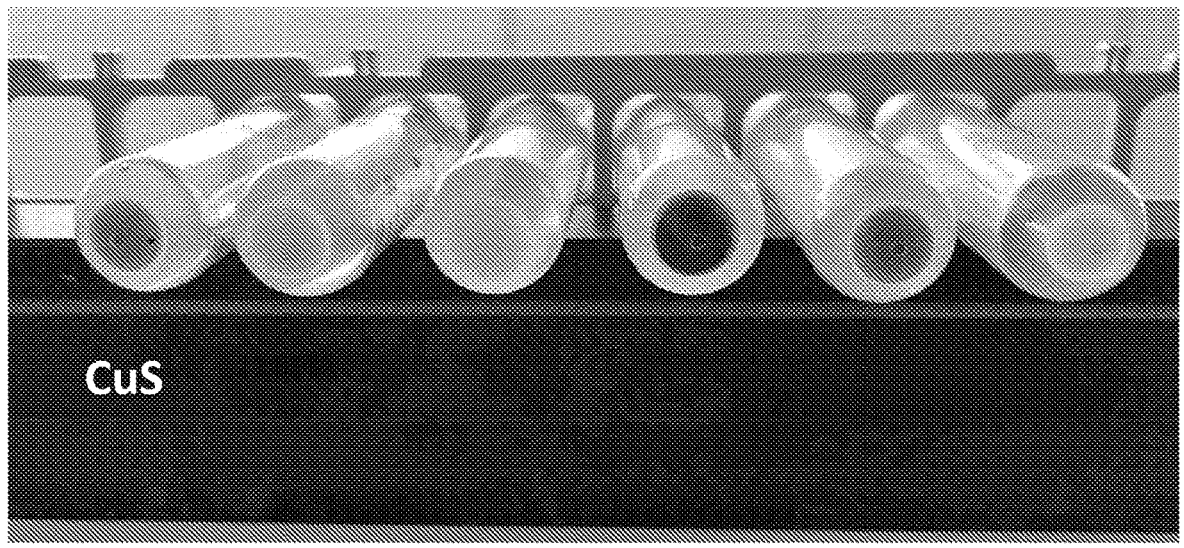
FIGS. 16A-16C show precipitation of metal sulfides using sulfur-producing yeast.
Figure 16B:
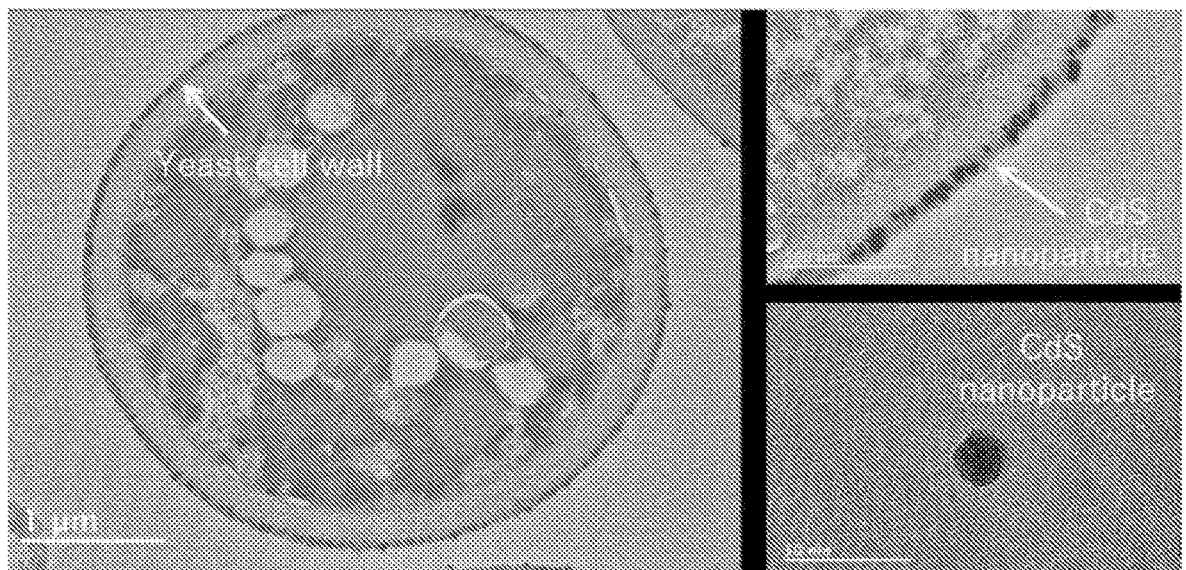
Figure 16C:
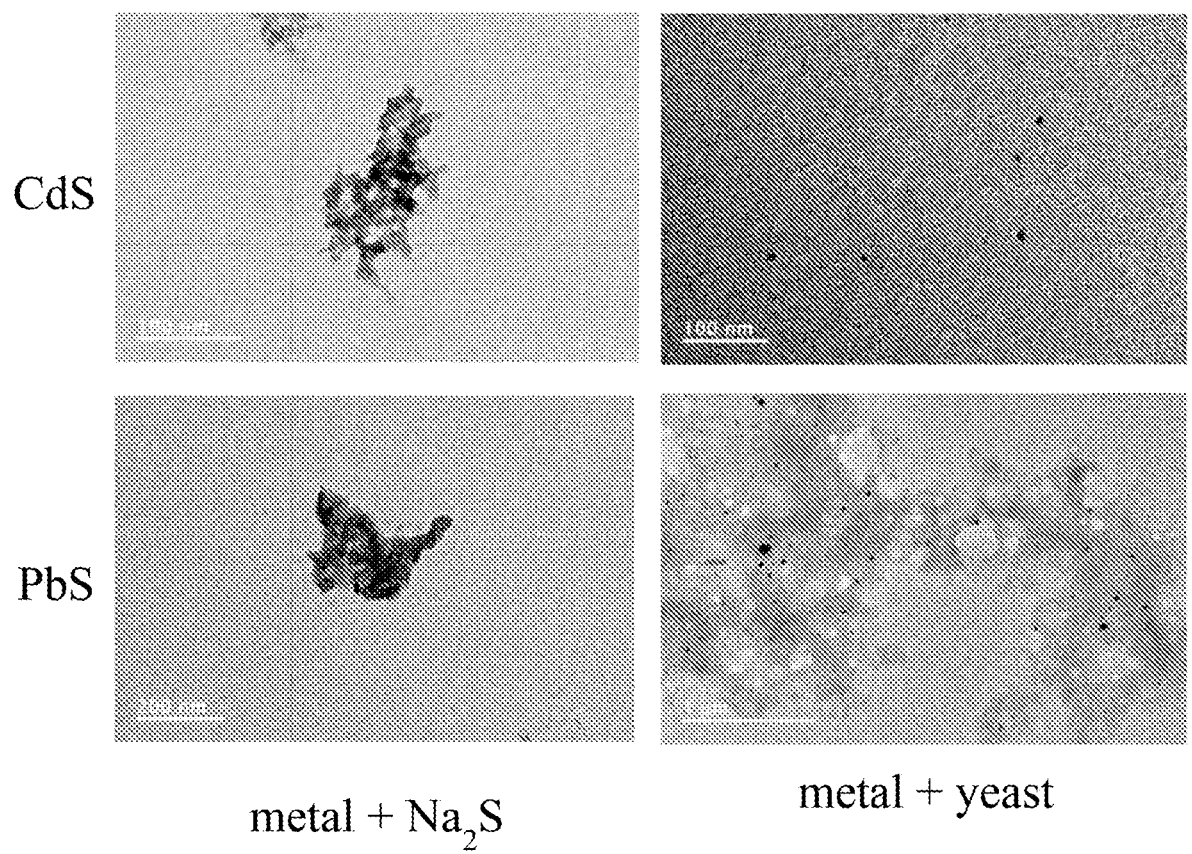
Figure 17:
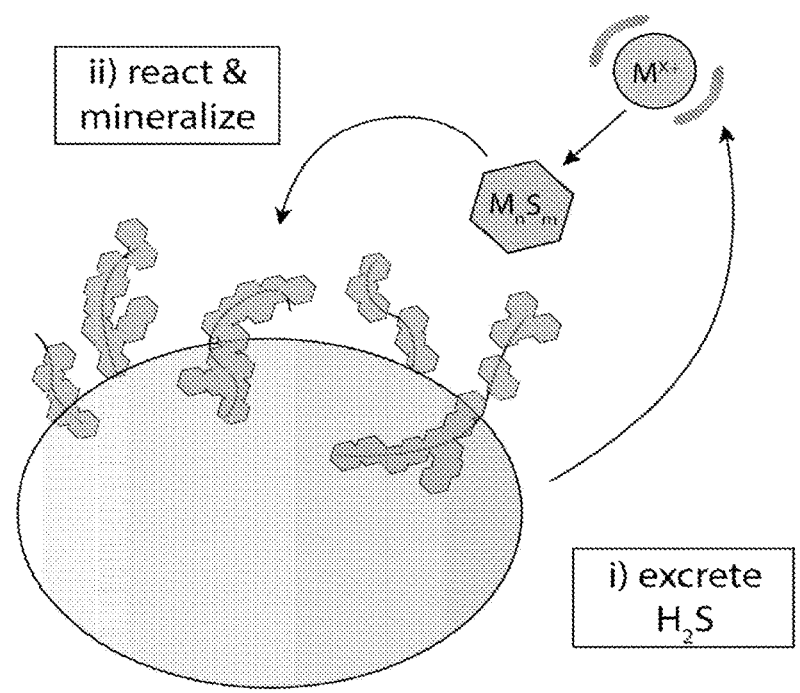
FIG. 17 shows hypothesized schematic of peptide mediated metal sulfide mineralization.

Supplementing cysteine to CSM rescues ΔCYS4 allowing a production of 102 ppm whereas ΔMET2,17 and ΔHOM2 produce almost half. Likewise, adding more methionine to CSM reduces ΔMET2,17 and ΔHOM2 production by half. An explanation for the nutrient effects on sulfide production is that the addition of cysteine or methionine eliminates the stress for thiol biosynthesis which reduces sulfide production (FIG. 15C). Conversely, the addition of cysteine allows ΔCYS4 to grow, and since ΔCYS4 is the biggest roadblock for cysteine synthesis (hence the auxotrophy), the sulfate pathway terminates at hydrogen sulfide gas which is thereby released.

3.2. Yeast Induced Metal Sulfide Precipitation

Metal sulfides have an extremely low solubility constant in solutions pH adjusted between 4-10. See DigitalAnalysisCo. Heavy Metal Reduction from Industrial Wastewater Streams, 2016, which is incorporated by reference in its entirety. Because of this, industrial chemical precipitation sometimes uses sulfur to treat highly contaminated waste water. However, the volatility and storage of sulfur becomes a hazard, so many industrial sites instead opt for sodium hydroxide. See Eddy Metcalf. Wastewater engineering: Treatment, disposal, reuse, metcalf & eddy. Inc., McGraw-Hill, New York, 2003, which is incorporated by reference in its entirety. Sulfide-producing yeast, however, is not burdened by practical issues of sulfur management because the yeast itself can be easily packaged and stored. Storage of sulfur simply requires the storage of yeast that produces it. Furthermore, sulfide production can be easily regulated depending on the demand by controlling nutrient conditions and gene expressions in the sulfate assimilation pathway.

Producing Cd, Cu Particles $\Delta$CYS4, $\Delta$HOM2, and $\Delta$MET2,17 mutants are able to precipitate approximately 1 mM $Cu^{2+}$ and 100 $\mu$M Cd in CSM ($\Delta$CYS4 cultures supplemented with cysteine).

Cross-sectional examination of metal precipitated cells using cryo-sectioning and TEM show that CuS and CdS particles precipitate on the cell wall. Simple lysis of the cell wall releases these particles which consistently range between 20-50 nm in diameter.

3.3. Using Yeast Display to Control Metal Sulfide Formation

Crystalline and structured metal sulfides are valuable for their applications in electronics, material fabrication, and optics. See Jagadese J Vittal and Meng Tack Ng. Chemistry of metal thio- and seleno-carboxylates: precursors for metal sulfide/selenide materials, thin films, and nanocrystals. Accounts of chemical research, 39(11):869-877, 2006, which is incorporated by reference in its entirety. Compounds such as CdS, PbS, ZnS are routinely used for optics and quantum dot synthesis. See A Mews, A Eychmüller, M Giersig, D Schooss, and H Weller. Preparation, characterization, and photophysics of the quantum dot quantum well system cadmium sulfide/mercury sulfide/cadmium sulfide. The Journal of Physical Chemistry, 98(3):934-941, 1994, which is incorporated by reference in its entirety.

Yeast are able to uniformly precipitate CuS, CdS, ZnS, PbS, and HgS; however, the mechanism is currently unknown, yet may be due to interactions with the cell wall. In certain embodiments, particle formation can controlled via changing the surface chemistry of the cell wall by displaying peptides using yeast display. There are already known peptides that can mineralize the formation of CdS and ZnS, which has been done on the M13 bacteriophage coat protein by the Belcher Lab. See Chuanbin Mao, Christine E Flynn, Andrew Hayhurst, Rozamond Sweeney, Jifa Qi, George Georgiou, Brent Iverson, and Angela M Belcher. Viral assembly of oriented quantum dot nanowires. Proceedings of the National Academy of Sciences, 100(12):6946-6951, 2003, which is incorporated by reference in its entirety.

Designing Metal Sulfide Biomineralization Libraries A straightforward approach is to take known metal sulfide mineralization peptides and test for mineralization. However, the current literature is limited to only a few peptides that facilitate mineralization in extreme buffer conditions not amenable to yeast cultures (e.g. high pH, low salt content, and typically hazardous reducing agents). Moreover, these peptides solely focus on CdS, PbS, or CuS which can already be formed with sulfur-producing yeast.

Figure 18:
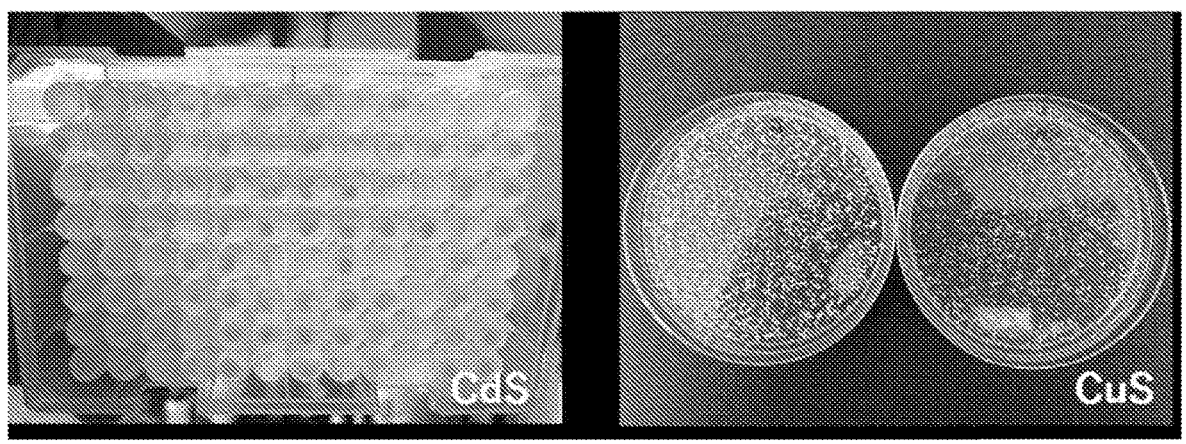
FIG. 18 shows proof of concept screening of cadmium and copper metal sulfide formation using yeast display peptide libraries (left image). The amount of precipitated CdS can be modulated by displaying different peptides on the yeast surface. (right image) Likewise, colonies can be discriminated by colony color density.

Therefore, new metal sulfide biomineralization peptides have been self-generated by creating a yeast display library with degenerate sequence $(NDN-NNK)_{(8,12,16)}$ (SEQ ID NOS 1-3) (subscripts denoting repeats) that are biased towards cysteine, histidines, glutamic and aspartic acid residues. These libraries are inserted into a yeast display expression vector with the canonical yeast display AGA1 and AGA2 cassette (plasmid named pYAGA). Such libraries can be generated and mutants can be visually screened based on metal sulfide color changes either in cultures or on plates supplemented with the metal of interest (FIG. 18). More quantitative screening can be investigated using ICP and TEM.

3.4. Additional Embodiments

In certain embodiments, sulfide biomineralization yeast can be engineered and culture conditions can be optimized to control for metal sulfide particle formation.

In certain embodiments, yeast-synthesized metal sulfides can be used for either materials or electronics.

Investigating pH Effects on Fe, Pb, Zn, Etc. Particle Formation

Figure 19:
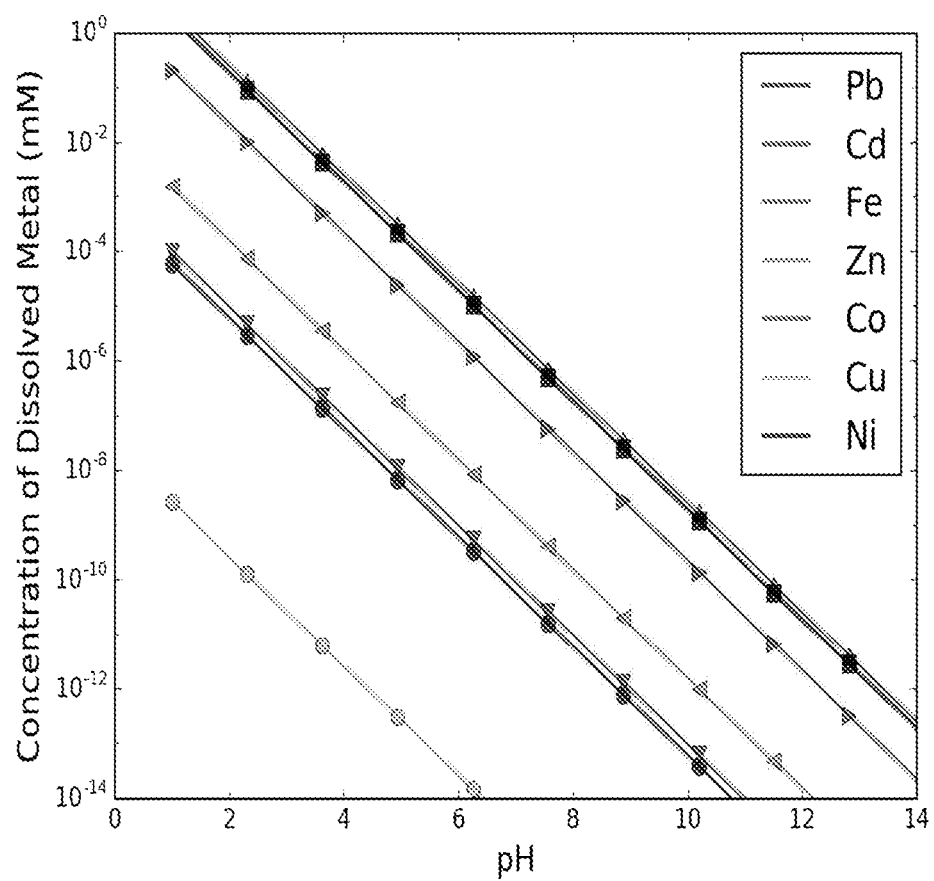
FIG. 19 shows solubility curves of metals at various pH values.

Adding 100 $\mu$M sodium sulfide ($Na_2S$) to yeast media readily precipitates copper, cadmium, as well as iron, lead, mercury and zinc. However, metals other than copper or cadmium are very difficult to precipitate with sulfur-producing yeast despite a similar buildup of produced sulfide. One hypothesis is that the rate of sulfur production is too slow. Meaning, the rate of sulfide escaping from the media as a gas is faster than the rate of reaction between metal and sulfide for the more soluble metals such as iron and zinc. And as a function of time, after 12-16 hours of yeast growth the culture pH can drop to 2, at which the pH is outside the permissible solubility range of most metal sulfide formation (FIG. 19). In FIG. 19, solubility/dissociation products and calculations were taken from online resources. See Renata Bellova, Danica Melicherčíková, and Peter Tomčík. Calculation of conditional equilibrium in serial multiple precipitation of metal sulfides with hydrogen sulfide stream generated from sodium sulfide: A didactic tool for chemistry teaching. Quimica Nova, 39(6):765-769, 2016, which is incorporated by reference in its entirety. Therefore, a slow sulfide production rate can accumulate slower than the drop in pH and prevent metal sulfide formation. A possible solution is to simply buffering yeast media to >pH 7 prior to inoculation to maintain the pH of the media above 4.

In summary, three unique strategies can utilize yeast for heavy metal remediation. The first employs cell surface display in combination with protein cell secretion to aggregate multiple repeats of the same protein on the yeast surface. This strategy improves upon conventional yeast display capture by multiplying the number of protein binding domains thereby increasing metal capture capacity up to 1-10 mM. The second strategy focuses on metal internalization by engineering metal transport systems at the cell membrane and vacuole. Using engineered SMF1 membrane transporter and CCC1 vacuole transporter, uptake of cadmium increases 10-fold when compared to WT. In certain embodiments, SMF1 can be being further modified to become sensitive to other relevant metals such as strontium, lead, and mercury. Finally, the third strategy uses hydrogen sulfide by-products from the yeast sulfate-assimilation pathway to react and precipitate heavy metals from solution. In certain embodiments, the formation of metal sulfide particles can be controlled with yeast displayed biomineralization peptides, or modulating hydrogen sulfide production rate, in order to obtain useful metal sulfide nanoparticles such as quantum dots. Strategies 1-3 can be combined to provide a powerful method for heavy metal remediation. Current ideas to synergistically combine the various strategies of metal binding, transport, and mineralization are shown in FIGS. 20A-20C.

These strategies can be used to build a platform in which industries and the public can accessibly and cheaply purify water. What makes yeast such an attractive platform is the ease to engineer and rapidly test better performing strains, and this can only get simpler with more advanced genetic engineering tools. In addition yeast circumvents many limitations hampering current physicochemical processes, such as renewability, cost, and production of secondary waste. Already the industry to cheaply scale the production of yeast exists because of the beer and pharmaceutical industry. See Argyro Bekatorou, Costas Psarianos, and Athanasios A Koutinas. Production of food grade yeasts. Food Technology and Biotechnology, 44(3):407-415, 2006, which is incorporated by reference in its entirety. Likewise, the food industry has establish protocols to handle, transport, and store yeast for consumer use, so there exist a feasible entry way for this technology to enter the public market. The methods disclosed here can be combined with already established yeast production infrastructures in order to provide yeast at low costs. Current infrastructures from the beer, pharma, and food industries can be utilized to create another avenue in which yeast can remediate toxic materials from industrial processes such as mining, chemical spills, and manufacturing runoff.

Examples

Yeast as a Sequestration Agent

A yeast strain that endogenously displays the AGA1 & AGA2 surface proteins was designed by constructing a DNA construct containing the AGA1 and AGA2 sequence with a strong constitutive promoter (GPO) and a canonical transcription terminator (CYC1). In addition, the AGA2 is followed by a protein of interest (POI) flanked by restriction sites NheI and XhoI (for cloning purposes) and a N'-HA and C-Flag tag (for expression studies). Finally, the construct is appended to a TRP1 autotrophic marker for positive selection of transformed yeast.

The POI are a family of plant metallothioneins (MT1A-4A) and the yeast endogenous metallothionein (CUP1). Metallothioneins are known to have strong affinities for copper, zinc, mercury, and lead. See Robinson, Nigel J., et al. "Plant metallothioneins," Biochemical Journal 295.Pt 1 (1993): 1. Yeast display of the AGAI & AGA2 constructs is used to express multiple copies of these metallothioneins (50,000-100,000 copies; see Boder. Eric T., and K. Dane Wittrup, "Yeast surface display for screening combinatorial polypeptide libraries," Nature biotechnology 15.6 (1997): 553-557, which is incorporated by reference in its entirety) on a single yeast surface to act as a metal binding domains.

TABLE 1

Table listing the 4 families of metallothioneins from Arabidopsis thaliana and the yeast metallothionein (CUP1) used for yeast display

| MT gene | Protein Sequence | SEQ ID NO |
|---|---|---|
| MT1A | MADSNCGCGSSCKCGDSCSCEKNYNKECDNCS CGSNCSCGSNCNC | 4 |
| MT2A | MSCCGGNCGCGSGCKCGNGCGGCKMYPDLGFS GETTTTETFVLGVAPAMKNQYEASGESNNA ENDACKCGSDCKCDPCTCK | 5 |
| MT3 | MSSNCGSCDCADKTQCVKKGTSYTFDIVETQE SYKEAMIMDVGAEENNANCKCKCGSSCSCV NCTCCPN | 6 |
| MT4A | MADTGKGSSVAGCNDSCGCPSPCPGGNSCRCR MREASAGDQGHMVCPCGEHCGCNPCNCPKT QTQTSAKGCTCGEGCTCASCAT | 7 |
| CUP1 | NIFSELINFQNEGHECQCQCGSCKNNEQCQKSC SCPTGCNSDDKCPCGNKSEETKKSCCSGK | 8 |

Data presented in this report are with respects to plant Arabidopsis thaliana metallothionein MT2A for conciseness and because all MTs tested show extremely similar results. Yeast display expression of MT2A increases Cu(II) uptake by 4-5 fold compared to WT which is >100 times higher than the US Environmental Protection Agency (EPA) actionable level of 1.3 ppm for allowable copper concentrations in drinking water. See file:///C:/Users/GeorgeSun/AppData/Roaroing/Zotero/Zotero/Profiles/wc3qz9ge.default/zotero/storage/S. regulated-drinking-water-contaminants.html, which is incorporated by reference in its entirety. In addition, MT2A yeast display strains are able to tolerate and thrive in high copper concentrations of about 16-20 mM, whereas WT die below 5 mM.

The plant metallothionein protein can be further engineered or evolved and screened for greater metal binding efficiency, capacity, and/or selectivity via high-throughput genetic engineering and screening methods such as flow cytometry.

Yeast as a Metal Absorber

Figure 21:
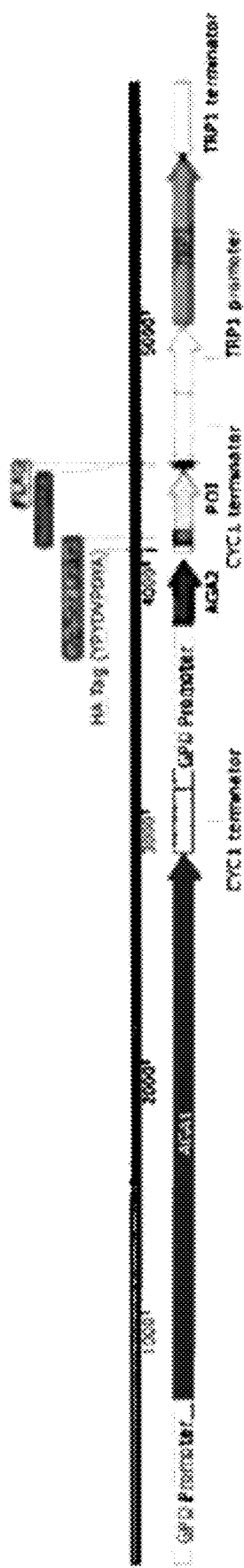
FIG. 21 shows sequence map of DNA cassette containing AGA1, AGA2, protein of interest (POI), and TRP1marker. Annotations specify relevant sequences such as promoters, terminators, tags, etc.
Figures 22A, 22B, 22C:
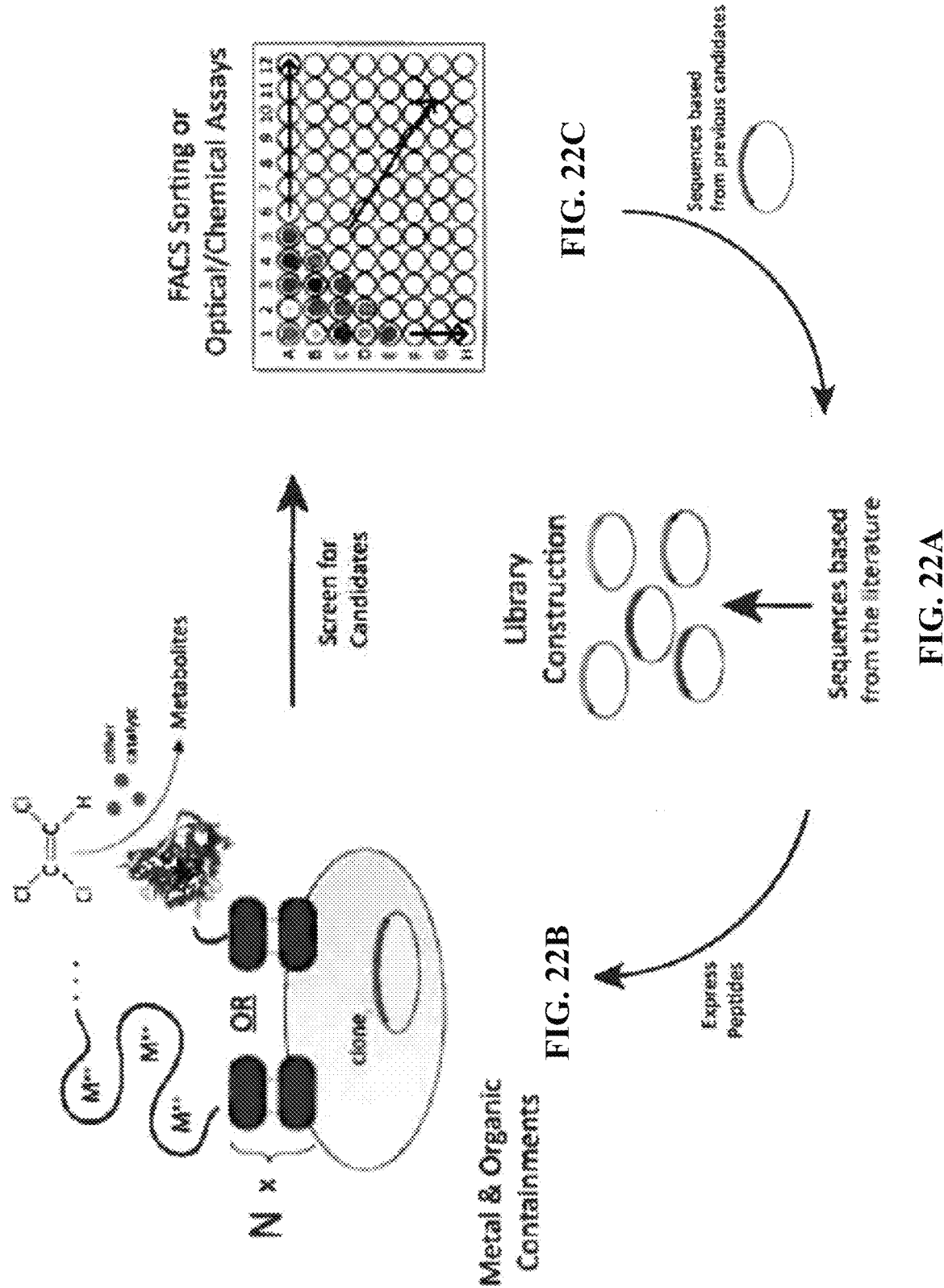
FIG. 22A shows sequences encoding MTs (or other proteins) can be rationally designed or mutated to generate a library of mutants to be tested for improved metal uptake, waste removal, or waste conversion.
FIG. 22B shows libraries screened via yeast display for metal uptake, or alternatively tested against waste removal such as TCE.
FIG. 22C shows selection based on optical, colorimetric, or chemical assays to screen for the most efficacious binders or catalyst via high-throughput platforms such as flow cytometry or automated plate readers.
Figure 23A:
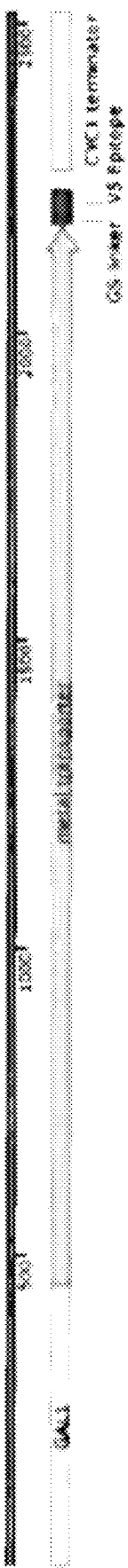
FIG. 23A shows sequence map of GAL1 inducible metal transporters followed by a V5 epitope tang and a CYC1 transcription terminator.
Figure 23B:
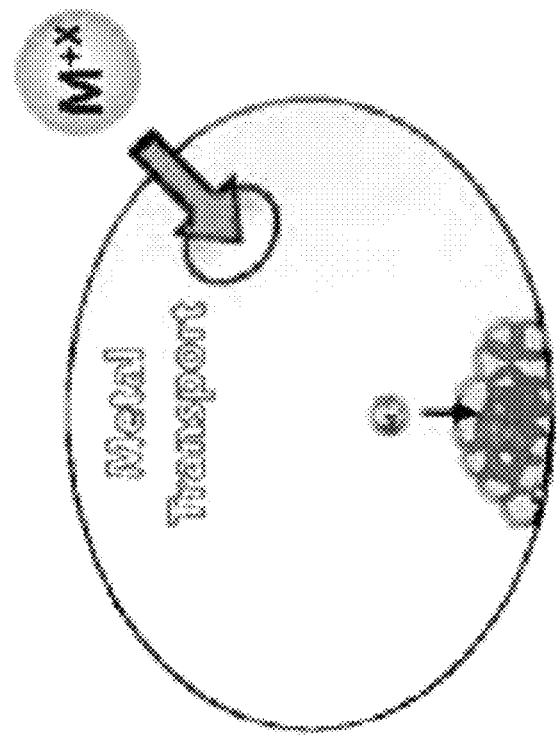
FIG. 23B shows illustration representing metal uptake via yeast metal transporters.
Figure 24A:
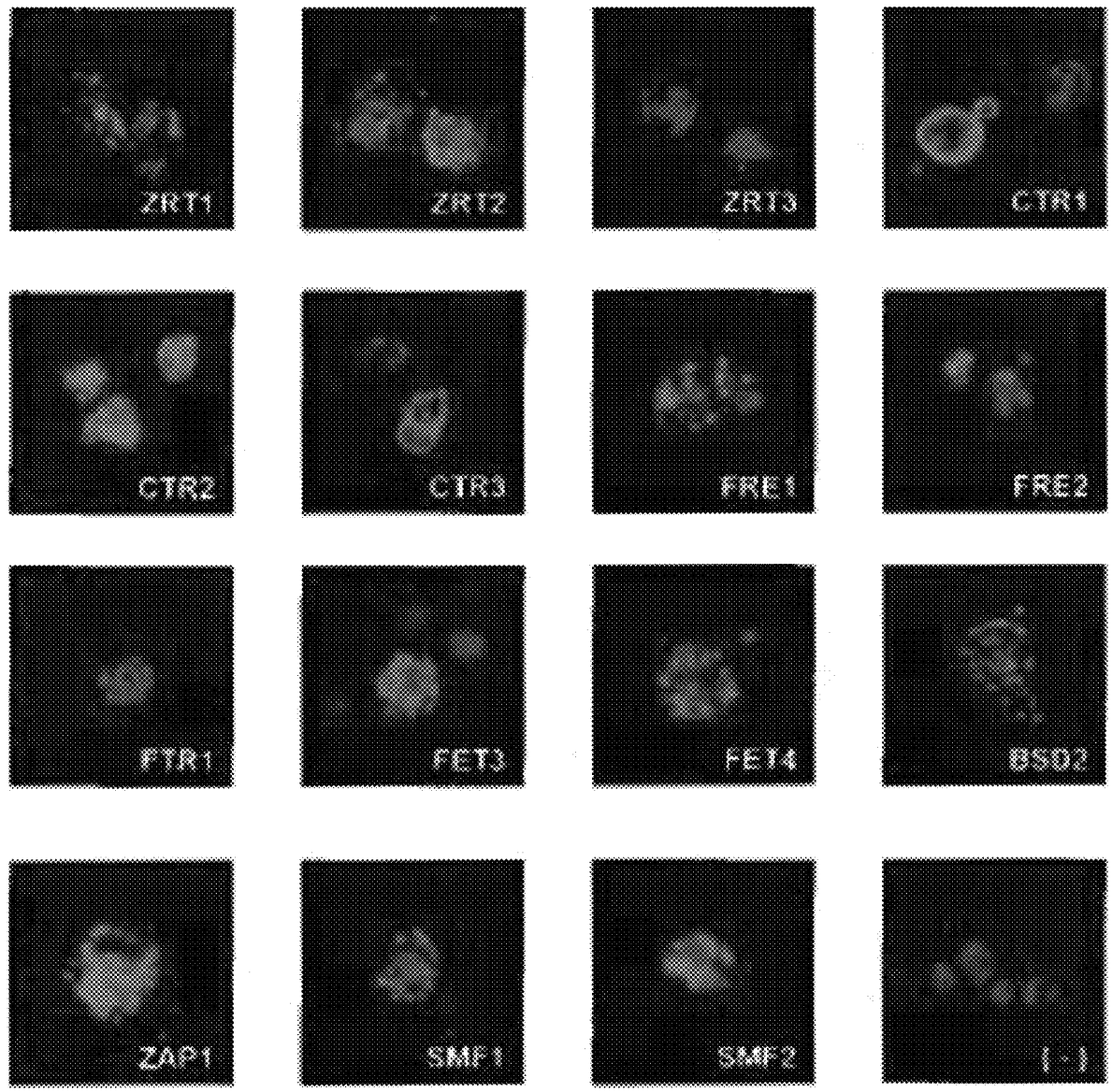
FIG. 24A shows that genes of yeast metal transporters for zinc (ZRTs), copper (CTRs), iron (FRE), etc. were overexpressed and expressions were qualitatively assessed using immunofluorescence by staining the V5 epitope tag.
Figure 24B:
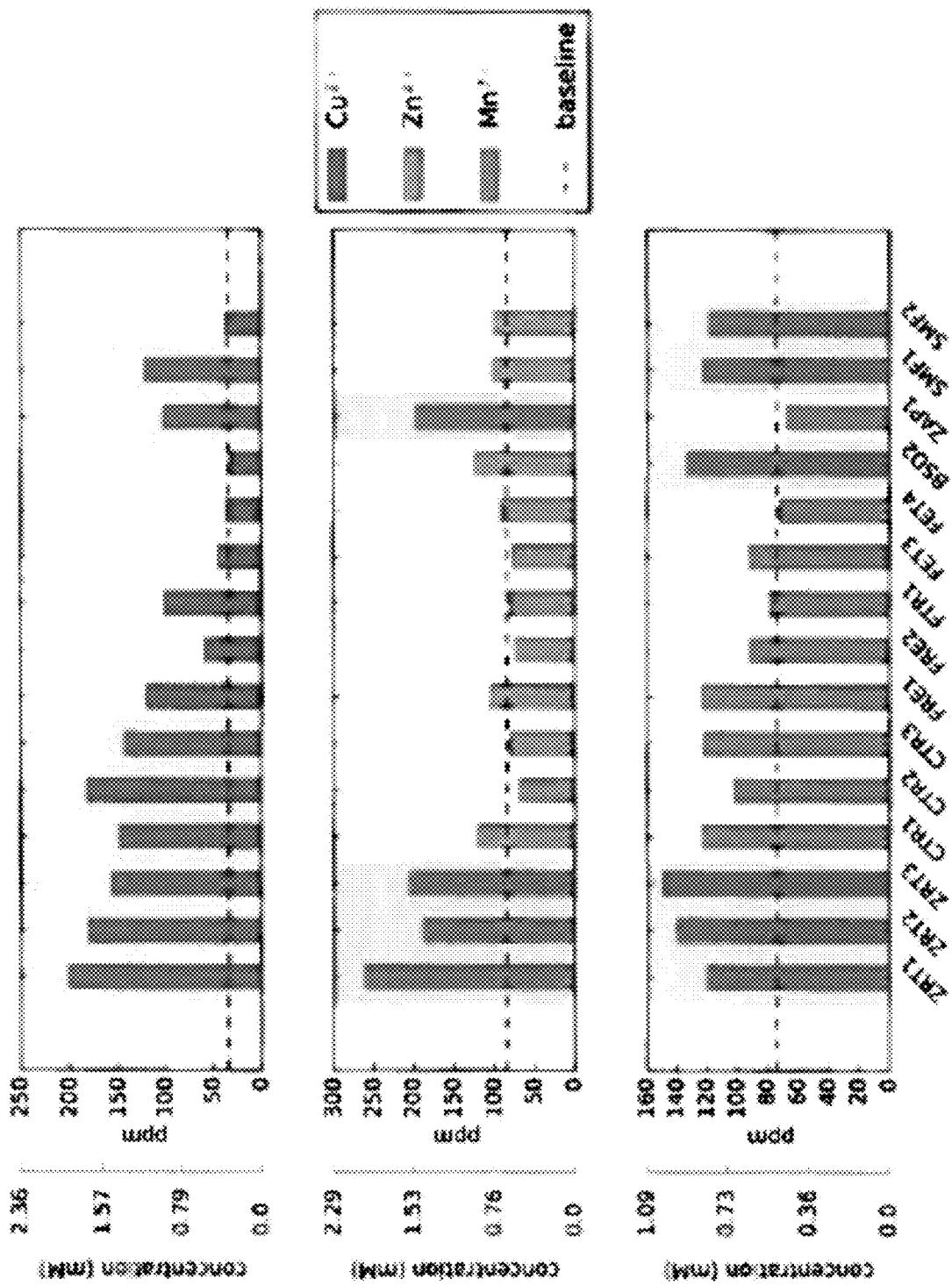
FIG. 24B shows uptake studies of over-expressed metal transporters for Cu(II) (blue), Zn(II) (red) and Mn(II) (purple). Highlighted bars indicate significant increase in uptake compared to WT (dashed line).

At a different perspective, the yeast's entire intracellular volume can be viewed as a sequestration locale. Several yeast strains that over-express a unique metal transporter (Table 2) were created by following similar DNA design strategies as described above (FIG. 21). See, Hall, J. L., and Lorraine E. Williams, "Transition metal transporters in plants," Journal of experimental botany 54.393 (2003): 2601-2613, which is incorporated by reference in its entirety. Each metal transporter gene is controlled by a GAL1 inducible promoter and followed by a V5 epitope tag (for staining purposes) and a CYC1 transcription terminator.

Of the expressed strains, metal uptake for Cu(II), Zn(II), and Mn(II) were tested.

TABLE 2

A list of most prominent metal transporters involved in yeast.

| Name | Description |
|---|---|
| ZRT1 | High-affinity zinc transport protein |
| ZRT2 | Low-affinity zinc transport protein |
| ZRT3 | Transports zinc from storage in the vacuole to the cytoplasm |
| ZAP1 | Involved in zinc ion homeostasis by zinc · responsive transcriptional regulation |

TABLE 2-continued

A list of most prominent metal transporters involved in yeast.

| Name | Description |
| --- | --- |
| CTR1 | Required for high affinity copper (probably reduced CuI) transport into the cell |
| CTR2 | Provides bioavailable copper via mobilization of vacuolar copper stores and export to the cytoplasm |
| CTR3 | Required for high affinity copper (probably reduced CuI) transport into the cell |
| FRE1 | Metalloreductase responsible for Fe3+ and Cu2+ salts |
| FRE2 | Metalloreductase responsible for Fe3+ and Cu2+ salts |
| FTR1 | Permease for high affinity iron uptake |
| FET3 | Iron transport multicopper ferroxidase required for Fe2+ ion high affinity uptake. Required to oxidize Fe2+ and release it from the transporter. Essential component of copper-dependent iron transport |
| FET4 | Required for Fe2+ ion low affinity uptake |
| BSD2 | Required for homeostasis of heavy metal ions such as cadmium, cobalt and copper. Under manganese-replete conditions facilitates trafficking of SMF1 and SMF2 metal transporters to the vacuole where they are degraded |
| SMF1 | High-affinity manganese transporter involved in manganese uptake from the extracellular environment. Contributes also to cellular accumulation of other divalent metal ions such as cadmium, cobalt, copper, iron and nickel |
| SMF2 | High-affinity manganese transporter involved in mobilizing manganese from vesicular stores in conditions of low manganese ion concentrations |

Recycling & Conversion of Toxic Metals Using Yeast Display

A metal's toxicity is based on its oxidation state and the molecular compound in which it is in. For example, Cr(VI), specifically chromates ($CrO_4^{2-}$, $Cr_2O_7^{2-}$) is considered highly mutagenic and acutely toxic, however Cr(III) is insoluble in water and is overall less reactive. Therefore, it is equally important to capture heavy metals as it is to convert and possibly recycle these metals to a more benign and usable form.

Organisms have already discovered methods to convert metals from an unfavorable state to a more favorable one. Specifically, cytochromes found in dissimilatory metal reducing bacteria are known to transfer electrons to heavy metals as terminal electron acceptors in order to generate an electrochemical gradient for the production of chemical energy. See Lovley, Derek R. "Dissimilatory metal reduction." Annual Reviews in Microbiology 47.1 (1993): 263-290, which is incorporated by reference in its entirety. These proteins all contain a porphyrin cofactor in which a chelated metal facilitates the transfer of electrons from a metabolic substrate (i.e. conversion of NAD(P)H, formate, lactate, or pyruvate, etc.) to heavy metals from the environment. A similar mechanism is being pursued in yeast in which yeast cytochromes, CYC1 & 7, are displayed on the surface in hopes of facilitating electron transfer between environmental heavy metal and the cytochrome's heme group. An increase in redox potential of yeast displayed CYC1/7 was observed as evidence for the possibility of facilitated heavy metal reduction.

Biologically catalyzed metal reduction can be further pursued to create microbial fuel cells in which an organism, typically bacterial catalyzes the oxidation or reduction of an organic or inorganic matter to generate current. The same principal to reduce metals using yeast displayed cytochromes can simultaneously be harnessed to generate and store current ill a fuel cell.

Metal-Contaminated Yeast after Water Treatment

Figure 25:
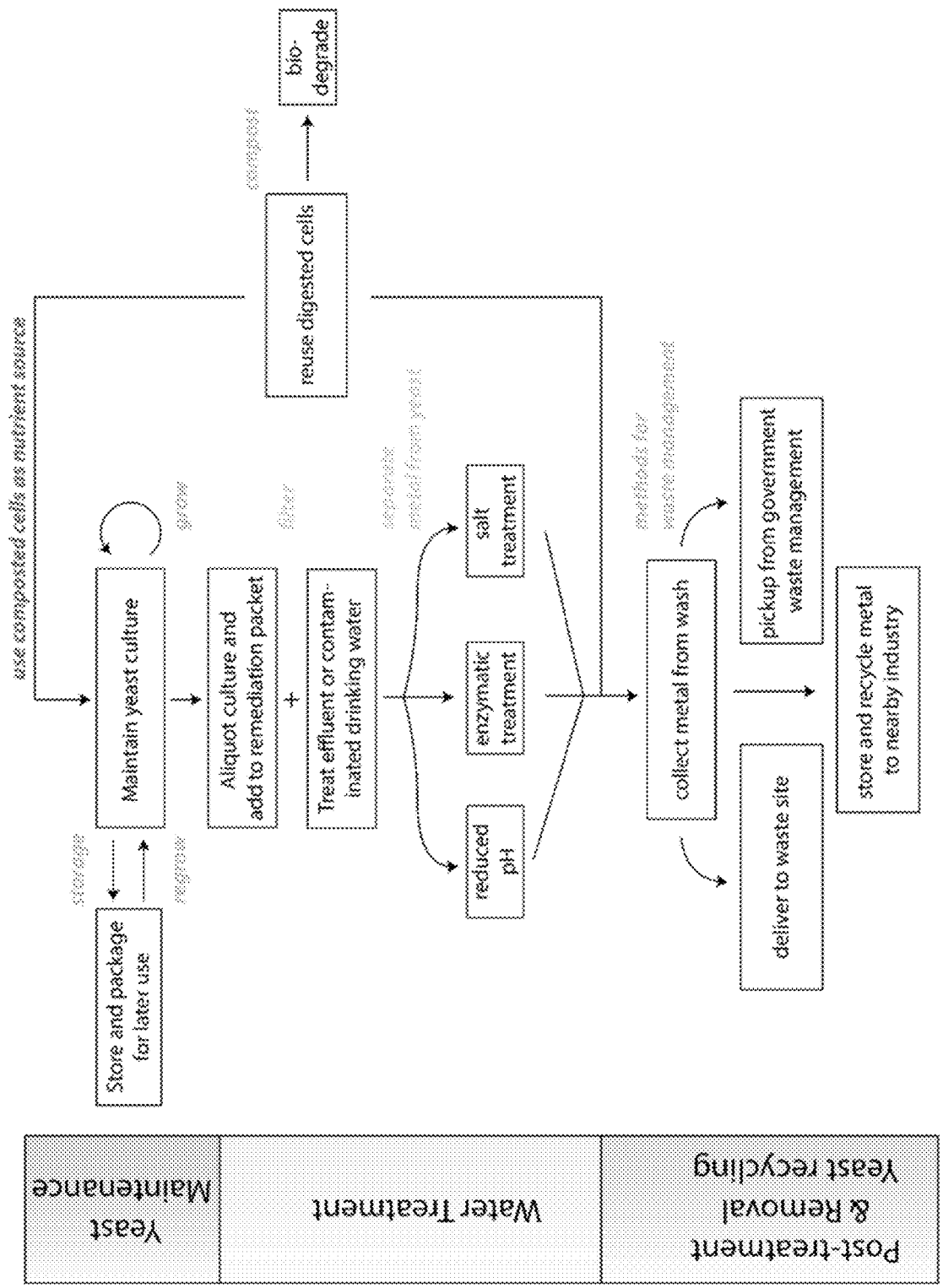
FIG. 25 shows flow diagram of using and recycling DIY yeast remediation packets for heavy metal removal.

Metal-contaminated yeast filter packets can be handled many different ways after water treatment. The first is to reuse or recycle the filter packet by removing the captured heavy metal. The most direct method to release captured metals is to gently wash the yeast filter packet for metal removal at reduced pH (pH 3-4). The second method is to enzymatically treat the yeast with proteases to cleave the protein-metal complexes off the cells. After separation, yeast can be air-dried, stored, and later reconstituted when another batch needs to be cultured (FIG. 25). In FIG. 25, the first stage (green layer) provides an easy method to culture and propagate stocks of yeast. Yeast can be grown indefinitely given enough space and nutrients, or stored and consolidated in packets for later use. When yeast are needed (orange layer), cultures can be aliquoted from the main stock and added into the remediation filter packet. Contaminated waters can be manually pumped or washed over the filter packet to capture any metal contaminants. From here, yeast can be separated from the captured metal by washing at reduced pH, enzymatic, or salt treatment (blue layer). Yeast can be reused, composted, or autolyzed as a nutrient source for subsequent culture growth. Captured metals should be thrown out to dedicated waste sites or delivered to industries or government agencies that can recycle the metals.

A drop in strain integrity was observed after remediation, such as slower growth rates, incomplete separation of contaminants, or strain mutations, yeast can be lysed and then biodegraded. Lysis simply requires salted water, approximately a few hundred millimolar (6-30 grams per liter of water) (see Huh, G.-H. et al. Salt causes ion disequilibrium-induced programmed cell death in yeast and plants. *Plant J.* 29, 649-659 (2002), which is incorporated by reference in its entirety), to create a hypertonic environment in which yeast undergo autolysis. Hypertonic solutions swell and eventual burst the yeast cell releasing enzymes and proteases causing cellular degradation. Autolysis effectively reduces yeast biomass into yeast extract, a rich blend of basic nutrients such as amino acids and nitrogen sources that can feed future cultures of yeast. See Chae, H. J., Joo, H. & In, M.-J. Utilization of brewer's yeast cells for the production of food-grade yeast extract. Part 1: effects of different enzymatic treatments on solid and protein recovery and flavor characteristics. *Bioresour. Technol.* 76, 253-258 (2001), and Tanguler, H. & Erten, H. Utilisation of spent brewer's yeast for yeast extract production by autolysis: The effect of temperature. *Food Bioprod. Process.* 86, 317-321 (2008), each of which is incorporated by reference in its entirety. Yeast extract is not toxic (as yeast extract is commonly used as a food additive for flavoring). There also exist commercial food brands based on yeast extract such as Vegemite and Marmite.

Target Heavy Metals

Two categories of heavy metals can be considered. The first category is divalent elemental metals such as lead ($Pd^{2+}$), mercury ($Hg^{2+}$), cadmium ($Cd^{2+}$), etc. The second category is polyatomic and organic metals such as chromium, which is typically found as chromate ($CrO_4^{2-}$); arsenic, which is typically found as arsenate ($AsO_4^{3-}$); and organomercury, which is found in numerous states with methyl functional groups (e.g., $CH_3$—$Hg^+$).

The first category was successfully demonstrated in terms of enhancing uptake capacity, specificity, and ability to sequester and compartmentalize elemental metal contaminants. However, for polyatomic and organic metal compounds, due to their different chemistries, differing yeast metabolic pathways, and obviously the difference in charge and valency, the strategies to address elemental metal capture need to be adjusted. Yeast permeases, in particular sulfate ($SO_4^{2-}$) and phosphate ($PO_4^{3-}$) permeases, can be used to uptake chromate ($CrO_4^{2-}$) and arsenate ($AsO_4^{3-}$), respectively, since the structural similarity between the two species would allow for direct pumping in of the metal oxide counterpart. Hyperaccumulation of chromate and arsenate using two sulfate permease genes (Sul1 and Sul2) and are in a position to further engineer and optimize the system. The other two strategies, yeast surface capture and mineralization are still being engineered to accommodate this second category of targets. This technology can be used for water treatment in areas such as Flint as well as other neglected areas poisoned by industrial runoff and mining effluent.

Safety for Drinking Water Applications

An easy to follow and robust method for water treatment that is adaptable to geographical location, types of water sources, user level of expertise, in addition to withstanding common user modes of failure can be provided. The mode of operation is to filter water through a yeast packet and funnel the flow through into a water container. Alternatively, the packet can be submerged in the treated water (much like a sponge) where the water can then be collected.

To ensure robustness of yeast filter packet, treated waters can be strained in a size-exclusion filter to remove particulate and yeast. Commonly used and available size-exclusion filters with 0.2-0.5 μm (see Corning sterile filtration guide, available at: www.corning.com/media/worldwide/cls/documents/CLS-FIL-004%20REV4%20DL.pdf (accessed: 30 Mar. 2017), which is incorporated by reference in its entirety) pore sizes are small enough to segregate yeast from entering the water.

Also, the strains are engineered to be autotrophic, that is they lack the capacity to produce essential nutrients for growth, typically amino acids such as tryptophan, histidine, leucine etc. Unless supplied by the user (during culture), yeast cannot survive and will eventually die if outside of filter.

The engineered strains are able to flocculate given an external stimulus. The packet can contain factors that suppress flocculation. In the event that the yeast reside outside the filter, then without access to the flocculation suppressing factors, flocculation would occur, which induces yeast precipitation and automatic removal from the water.

A variety of pH- and metal-tolerant biodegradable hydrogels can encapsulate and secure yeast in a contained filter packet. These packets can then be surrounded in a semi-porous membrane (e.g. similar to dialysis tubing) to allow diffusion of treated water into the packet, yet disallow movement of larger molecules beyond a given molecular size cutoff. See Ma, Y. et al. Effects of nanoplastics and microplastics on toxicity, bioaccumulation, and environmental fate of phenanthrene in fresh water. *Environ. Pollut.* 219, 166-173 (2016), Gimpel, J., Zhang, H., Davison, W. & Edwards, A. C. In Situ Trace Metal Speciation in Lake Surface Waters Using DGT, Dialysis, and Filtration. *Environ. Sci. Technol.* 37, 138-146 (2003), and Nolan, A. L., Mclaughlin, M. J. & Mason, S. D. Chemical Speciation of Zn, Cd, Cu, and Pb in Pore Waters of Agricultural and Contaminated Soils Using Donnan Dialysis. *Environ. Sci. Technol.* 37, 90-98 (2003), each of which is incorporated by reference in its entirety. The hydrogels in the packet are meant to be degraded so that metals can be stripped and segregated from the yeast after use. Yeast can then be harvested for re-inoculation or degradation as described in FIG. 25.

If the packet degrades after successive water treatments, the semi-porous membrane adds another barrier of selection against particles dissolving into the water. The dialysis tubing, most likely made of nitrocellulose or a cellulose monomer, is typically resistant to many chemicals and pH ranges and has long shelf and usage lifetimes. See Snake-Skin Dialysis Tubing, available at: tools.thermofisher.com/content/sfs/manuals/MAN0011339_SnakeSkin_Dialy_Tubing UG.pdf (accessed: 30 Mar. 2017), and Spectra Cellulose Dialysis Membrane, available at: www.spectrumlabs.com/lit/420x10116x000.pdf (accessed: 30 Mar. 2017), each of which is incorporated by reference in its entirety.

Although yeast has been engineered to secrete a variety of proteins for commercial and pharmaceutical purposes, native yeast has a limited secretome. See Choi, J. et al. Fungal Secretome Database: Integrated platform for annotation of fungal secretomes. *BMC Genomics* 11, 105 (2010), which is incorporated by reference in its entirety. Most secreted proteins are typically mating factors or pheromones needed to communicate with other cells during haploid mating events. See Loumaye, E., Thorner, J. & Catt, K. J. Yeast mating pheromone activates mammalian gonadotrophs: evolutionary conservation of a reproductive hormone? *Science* 218, 1323-1325 (1982), which is incorporated by reference in its entirety. If this is any cause for concern, these pathways can be easily knocked out to limit the amount of factors secreted. Secretion may not be a concern given that beer is essentially the collection and reduction of yeast supernatant (these strains will not be fermented, so no production of sugars or alcohols should exist in the filtered water).

To prevent incomplete metal capture, preliminary on-site measurements can be performed to see how this yeast filter packet capture capacity scales with the amount of metal contaminants in the local waters to be treated. Given an approximate estimate of local contaminant concentrations, different sizes or densities of yeast packets can be used to efficiently remove all contaminants in one treatment cycle. Alternatively, multiple yeast packets can be used in-tandem per treatment for increased capture capacity.

Figure 26:
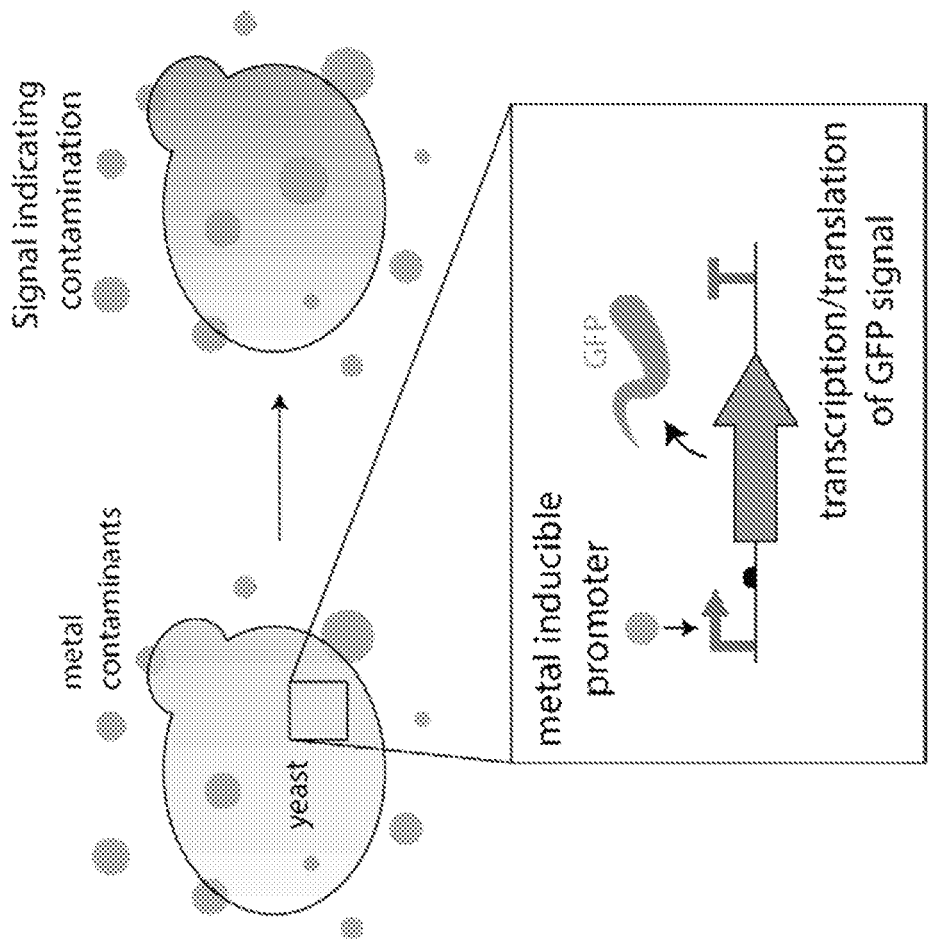
FIG. 26 shows a simple genetic switch turns on the production of the green fluorescent protein (GFP) to indicate the presence of metal contaminants still present in the filtered drinking water.

In the treatment pipeline, a metal sensing packet can be introduced. A packet containing yeast can colorimetrically or fluorescently respond to metal contaminants. For example, the packet can contain yeast that has a green fluorescent protein (GFP) downstream of a metal-inducible promoter (FIG. 26). These packets can be separated from the remediation packet, but can still follow the culturing and usage pipeline outlined in FIG. 25. Promoters include those that control metallothionein and glutathione transcription (CUP1, MTF-1, etc.), which can be used to control GFP expression. See Saydam, N., Adams, T. K., Steiner, F., Schaffner, W. & Freedman, J. H. Regulation of Metallothionein Transcription by the Metal-responsive Transcription Factor MTF-1 IDENTIFICATION OF SIGNAL TRANSDUCTION CASCADES THAT CONTROL METAL-INDUCIBLE TRANSCRIPTION. *J. Biol. Chem.* 277, 20438-20445 (2002), and Ecker, D. J. et al. Yeast metallothionein function in metal ion detoxification. *J. Biol. Chem.* 261, 16895-16900 (1986), each of which is incorporated by reference in its entirety.

Wastewater Remediation Versus Drinking Water

Wastewater remediation is of great interest, particularly mining and agricultural runoff. However, the most pressing issue in developing areas and economically disadvantaged communities is the inaccessibility of safe drinking water. The disclosed method can provide a renewable platform to continuously grow and use water remediation agents (yeast) that can empower communities to clean their own waters.

Accessible and usable in DIY packets with yeast can be grown and maintained in a user-friendly manner in many geographical regions.

Yeast Versus Sulfate-Generating Bacteria (to Precipitate Metalloid Sulfides)

Yeasts are easier to grow, have shorter doubling times, and have an extensive toolkit for molecular biology engineering. In addition, yeast strains that are able to produce sulfur require the same nutrients as wild-type strains, as the deletion of the sulfate-assimilation pathway does not perturb any other metabolic pathway.

In comparison to sulfur-generating bacteria, commonly found in the families of Desulfobacterales, Desulfovibrionales and Syntrophobacterales (see Muyzer, G. & Stams, A. J. M. The ecology and biotechnology of sulphate-reducing bacteria. *Nat. Rev. Microbiol.* 6, 441-454 (2008), which is incorporated by reference in its entirety), these strains are very difficult to grow and engineer compared to yeast. These cultures require anaerobic conditions, meaning oxygen is lethal to their growth and require controlled anaerobic chambers devoid of oxygen with precise control of humidity and temperature. In addition, production of sulfur requires additional nutrients that are otherwise not needed for commonly used bacteria and yeast strains, such as propionate, high sulfate concentrations, or fermentable lactate and ethanol. See Muyzer, G. & Stams, A. J. M. The ecology and biotechnology of sulphate-reducing bacteria. *Nat. Rev. Microbiol.* 6, 441-454 (2008), and H Kadota & Ishida, and Y. Production of Volatile Sulfur Compounds by Microorganisms. *Annu. Rev. Microbiol.* 26, 127-138 (1972), each of which is incorporated by reference in its entirety. Even under the best growth conditions, the pathway and control of sulfur production in sulfur-generating bacteria are relatively unclear and still require further investigation. See Schippers, A. & Sand, W. Bacterial Leaching of Metal Sulfides Proceeds by Two Indirect Mechanisms via Thiosulfate or via Polysulfides and Sulfur. *Appl. Environ. Microbiol.* 65, 319-321 (1999), and Friedrich, C. G., Rother, D., Bardischewsky, F., Quentmeier, A. & Fischer, J. Oxidation of Reduced Inorganic Sulfur Compounds by Bacteria: Emergence of a Common Mechanism? *Appl. Environ. Microbiol.* 67, 2873-2882 (2001), each of which is incorporated by reference in its entirety. Understanding this pathway is further hindered by the difficulty of genetically engineering sulfur-generating strains, as they offer few avenues for genetic manipulation compared to more evolved bacteria and yeast strains. Strain engineering in bacteria usually requires horizontal gene transfer of a shuttle vector from a well-defined and engineerable host such as bacteria; this added layer of complexity overall slows the engineering pipeline for improved strain performance. See Dodsworth, J. A. et al. Interdomain Conjugal Transfer of DNA from Bacteria to Archaea. *Appl. Environ. Microbiol.* 76, 5644-5647 (2010), which is incorporated by reference in its entirety.

To summarize, the engineered yeast strains require minimal culture effort, grow at ambient temperature with limited impact on ambient air conditions, and produce appreciable quantities of sulfur. In a head-to-head comparison with respect to sulfur production, the engineered strains can produce 55±8 ppm of sulfur per culture (12 hours of growth in an Erlenmeyer flask), whereas depending on the bacteria strain, nutrient source, and culturing method (flask, fermentation chamber, bioreactor, etc.) production of sulfur can range from 7.5 to 67 ppm (see Jong, T. & Parry, D. L. Removal of sulfate and heavy metals by sulfate reducing bacteria in short-term bench scale upflow anaerobic packed bed reactor runs. *Water Res.* 37, 3379-3389 (2003), which is incorporated by reference in its entirety) in 12 hours. Yeast is favored because of its ease of use, known sulfur pathway, and controllability of sulfur production.

Scalability and Preliminary Cost Analysis of DIY Yeast Packets

Beer industry can be used as a reference on the economics of yeast production and cite academic literature on bioseparation processes and distribution for evaluating the scalability and cost of the DIY yeast packets. The United States alone produced 55 billion gallons of beer in 2012. See The Economics of Craft Beer|SmartAsset.com. SmartAsset (2017), available at: smartasset.com/credit-cards/the-economics-of-craft-beer (accessed: 2 Apr. 2017), which is incorporated by reference in its entirety. Typically, 2-10 billion yeast cells are needed to ferment a single gallon of beer (see Baker, D. A. & Kirsop, B. H. Rapid Beer Production and Conditioning Using a Plug Fennentor. *J. Inst. Brew.* 79, 487-494 (1973), which is incorporated by reference in its entirety), making yeast production estimated at approximately 24 thousand tons of biomass per year (see Bryan, A. K., Goranov, A., Amon, A. & Manalis, S. R. Measurement of mass, density, and volume during the cell cycle of yeast, *Proc. Natl. Acad. Sci.* 107, 999-1004 (2010), which is incorporated by reference in its entirety). These yeasts are either recycled for use in another production batch or discarded. These numbers do not consider the production of yeast for consumer and pharmaceutical goods like bread, dried-yeast packets, and therapeutic compounds which is on the same order of magnitude as the beer industry. What this means is that yeast is already a cheap, scalable, and consumer friendly type of microorganism that can be similarly scaled and distributed for water remediation purposes.

In typical bioprocessing settings (averaged for pharmaceutical applications) the cost of raw yeast is approximately $4 dollars per kilogram. See Harrison, R. G., Todd, P., Todd, P. W., Rudge, S. R. & Petrides, D. P. *Bioseparations Science and Engineering*. (Oxford University Press, 2015), which is incorporated by reference in its entirety. Ingredients to maintain cultures such as glucose, yeast extract, amino acids, and trace elements go for $3 dollars per kilogram of total material. Id. In the lab, typically 1 million cells are seeded per mL of yeast in 1 liter cultures. Therefore, the cost to start a culture is 16 cents per L culture. In the laboratory setting, and especially in batch and fermentation processes, yeast can undergo several doublings per inoculum. A final 1-liter culture may have as much as $1^{10}$-$1^{11}$ cells in 16 hours (experimentally determined). Therefore, the final cost of yeast per cost of raw material is most likely an order of magnitude lower than what is calculated.

With respects to the cost of yeast needed per packet, assuming contamination levels of up to 100 µM or more (equivalent to ten to a thousand times higher than EPA standards for certain metals; see EPA. *Wastewater Technology Fact Sheet Chemical Precipitation* (2000), available at://nepis.epa.gov/Exe/ZyPDF.cgi/P1001QTR.PDF?Dockey=P1001QTR.PDF (accessed: 5 Jan. 2017), which is incorporated by reference in its entirety), $1^{10}$ yeast cells or less would be required to completely purify a 1 liter solution (based on experimental results). Therefore, a packet containing $1^{10}$ cells would require a fraction of a liter, meaning the cost to purify water can start as low as a few pennies per liter of drinking water.

Therefore, the most expensive aspect of setting up a culture is the cost of equipment, transportation, and packaging. Breaking down the cost further, a pound (454 g) of freeze- or active-dried yeast for DIY brewing or bread making costs 5-30 dollars depending on the quality of yeast (i.e. number of surviving cells, QC testing, brand identification, etc.). Home brewing kits (typically sized as 5 gallons) can go for $30 to $300 dollars, again depending on the quality of the brand. See Association, H. A. Is Homebrewing Cheaper than Store-Bought Beer? *American Homebrewers Association* (2015), available at: www.homebrewersassociation.org/news/is-homebrewing-cheaper-than-store-bought-beer/(accessed: 2 Apr. 2017), which is incorporated by reference in its entirety. Therefore, to culture 1 L of yeast costs roughly $5-10 dollars on the low end. However, the startup cost can be lowered by using standard culturing flasks, simple ingredients, and the ability to freeze-dry one's own cultures to self-propagate cultures for future use.

Large-Scale Comparison of DIY Yeast Packets Versus Physicochemical Methods

Whether synthesizing resins, adsorption filters, or electrochemical substrates, the basic processing pipeline is as follows (see Harrison, R. G., Todd, P., Todd, P. W., Rudge, S. R. & Petrides, D. P. *Bioseparations Science and Engineering*. (Oxford University Press, 2015), and Jr, W. D. C. & Rethwisch, D. G. *Fundamentals of Materials Science and Engineering: An Integrated Approach*. (John Wiley & Sons, 2012), each of which is incorporated by reference in its entirety): (1) reactors and synthesis, Primary recovery—solid and phase separation, (2) intermediate recovery—ultrafiltration, evaporation, reverse osmosis, etc., (3) final purification—crystallization, solvent/pH exchange, chromatography, etc., (4) quality control (QC)—size, structure, chemical composition/characterization, etc., and (5) packaging and storage—typically requires technical handling and storage. Whereas bioprocessing of yeast requires: (1) continuous bioreactor, (2) cell separation—filtration or centrifugation of cellular debris, (3) QC—routine genotyping, and (4) packaging and storage—freeze-dried, air-dried, etc.

Yeast has advantages as it avoids complex synthesis steps, requires a simple isolation process, and QC reduces to simple strain genotyping to guarantee selection of engineered yeast. Moreover, iteration becomes more feasible as molecular biology engineering requires simple cloning technologies, such as DNA oligo design, polymerase chain reaction (PCR), and transformations, which can cost as little as a few dollars per experiment. See Guthrie, C. & Fink, G. R. *Guide to yeast genetics and molecular and cell Biology: Part C*. 351, (Gulf Professional Publishing, 2002), which is incorporated by reference in its entirety. For physicochemical processes, however, an entire synthesis pipeline may need to be adjusted to accommodate changing reaction conditions, and possibly entire facilities may need to be retro-fitted in case of incompatible reaction steps.

When compared with the current resin technology (chromatography), resins require chemical functionalization of polystyrene beads whose chemistries can be quite complex, making optimization of highly specified and selective resin groups difficult and slow. See Kentaro Tashiro, Modular synthesis of metal-organic complex arrays containing precisely designed metal sequences, available at: globalscience.berkeley.edu/sites/default/files/15-modularmoca.pdf (accessed: 2 Apr. 2017), which is incorporated by reference in its entirety. Likewise, resin-based technology may not be amenable for public use as storage conditions may differ per resin type and functional group, and resins are not easily recycled if users do not have technical knowledge of the precise chemistries and best practices for handling. Therefore, resins may actually contribute to secondary waste if not properly managed.

On the other hand, yeast provides a better alternative for resin water treatment, especially in the form of yeast display.

Surface protein expression is easily and greatly tunable on the genetic level while maintaining identical culturing conditions for un-engineered, or other engineered yeast strains. Likewise, yeast can be re-used or stored for later use as described in the sections above. But if yeast were to be discarded, they are biodegradable and would not contribute to secondary waste.

Compared to the current adsorption filters, similar arguments with resin technology, the manufacturing and chemistries of adsorption filters and membranes inhibit this technology from being widely distributed for public use. The first is the decline, or scarcity of resource materials such as nanostructured materials or carbon nanotubes. See Jong, T. & Parry, D. L. Removal of sulfate and heavy metals by sulfate reducing bacteria in short-term bench scale upflow anaerobic packed bed reactor runs. *Water Res.* 37, 3379-3389 (2003), and Stafiej, A. & Pyrzynska, K. Adsorption of heavy metal ions with carbon nanotubes. *Sep. Purif. Technol.* 58, 49-52 (2007), each of which is incorporated by reference in its entirety. Likewise handling and recycling of adsorption filters and membranes may be difficult to manage for untrained users.

One of the most highly used physicochemical methods for industrial waste treatment, chemical precipitation uses sacrificial iron compounds or reactive hydroxyl or sulfur groups to precipitate and remove metal complexes. See Charerntanyarak, L. Heavy metals removal by chemical coagulation and precipitation. *Water Sci. Technol.* 39, 135-138 (1999), which is incorporated by reference in its entirety. For scaled industrial use chemical precipitation costs are relatively cheap: approximately $0.05-$0.2 per liter of water in the US. See Ozturk, I., Altinbas, M., Koyuncu, I., Arikan, O. & Gomec-Yangin, C. Advanced physico-chemical treatment experiences on young municipal landfill leachates. *Waste Manag.* 23, 441-446 (2003), which is incorporated by reference in its entirety. However, this comes with hazardous pH ranges of 10-12 and handling of several grams of chemicals per liter. Additionally, sulfur is becoming a more prominent player in chemical precipitation for its speed and reactivity; however, chemical storage of sulfide in the form of sodium sulfide, iron sulfide, or sulfuric acid precursor is incredibly dangerous to handle and should be avoided in public hands. See Charerntanyarak, L. Heavy metals removal by chemical coagulation and precipitation. *Water Sci. Technol.* 39, 135-138 (1999), which is incorporated by reference in its entirety.

The production of hydrogen sulfide from a biological source is more benign than direct chemical precipitation. There is no need for storage of precursor chemicals for sulfide production, as the culture already contains the nutrients needed for yeast to metabolize. So if sulfur production were to be controlled, yeast can be easily moved from the media and idled in another buffer source or stored for future use. Finally, the sulfur content remains in solution and those that do become volatile and evaporate into the atmosphere where the concentration dramatically reduces to safe levels below EPA standards and is not a prominent safety concern. See EPA. Public Health Statement—Hydrogen Sulfide, available at: www.atsdr.cdc.gov/toxprofiles/tp114-c1-b.pdf (accessed: 2 Apr. 2017), and By Scott Simonton, P. D. & Oct. 3, 2007. Human Health Effects from Exposure to Low-Level Concentrations of Hydrogen Sulfide—. Occupational Health & Safety, available at: ohsonline.com/articles/2007/10/human-health-effects-from-exposure-to-lowlevel-concentrations-of-hydrogen-sulfide.aspx (accessed: 2 Apr. 2017), each of which is incorporated by reference in its entirety.

Regionally Specific, Personally Customized Deployable DIY Yeast Packets for Heavy Metal Remediation from Contaminated Water The engineered yeast can be packaged into user-friendly and economical units that can be deployed in areas in need of heavy metal remediation to provide strains of yeast that are regionally tailored so that users can simply grow and maintain their own batches of yeast for personal water remediation efforts. Instructions along with an ease to use culture containers can provide users a means to regularly grow their own yeast stocks for routine and self-sufficient water purification.

Figure 27A:
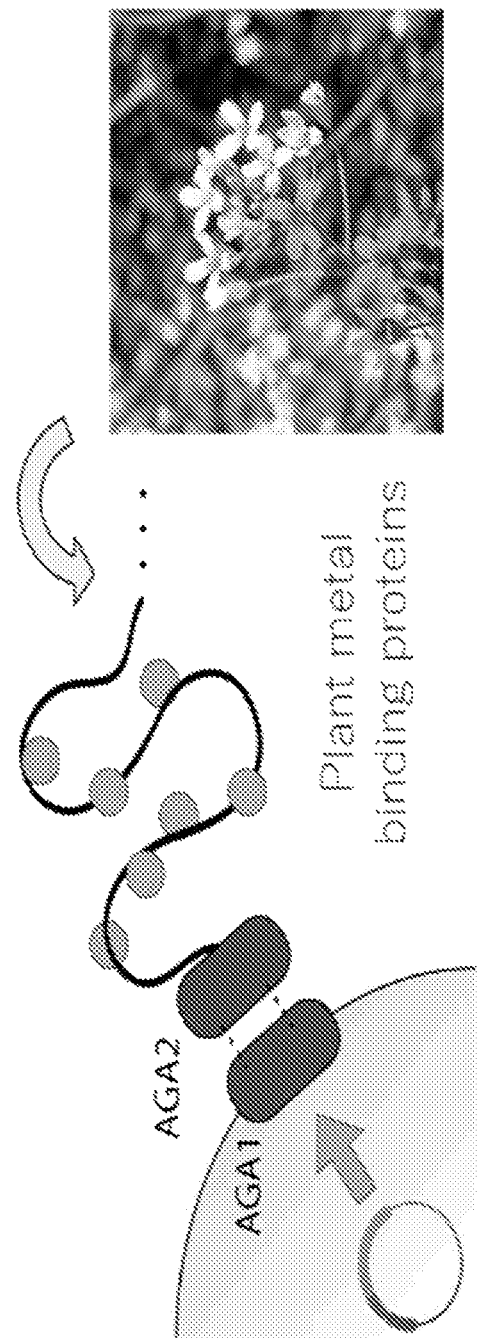
FIGS. 27A-27C show yeast display of plant metallothioneins (MTs) to demonstrate copper uptake and enhanced survivability in copper solutions.
Figure 27C:
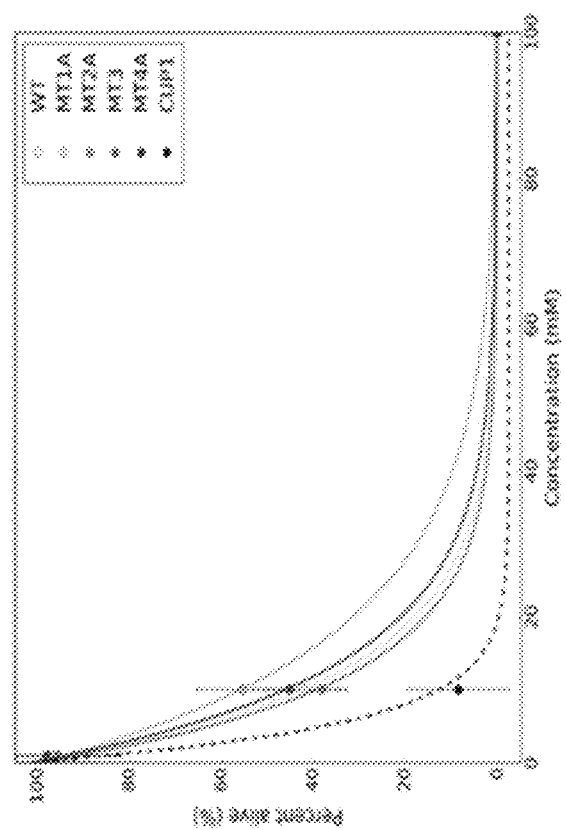
Figure 27B:
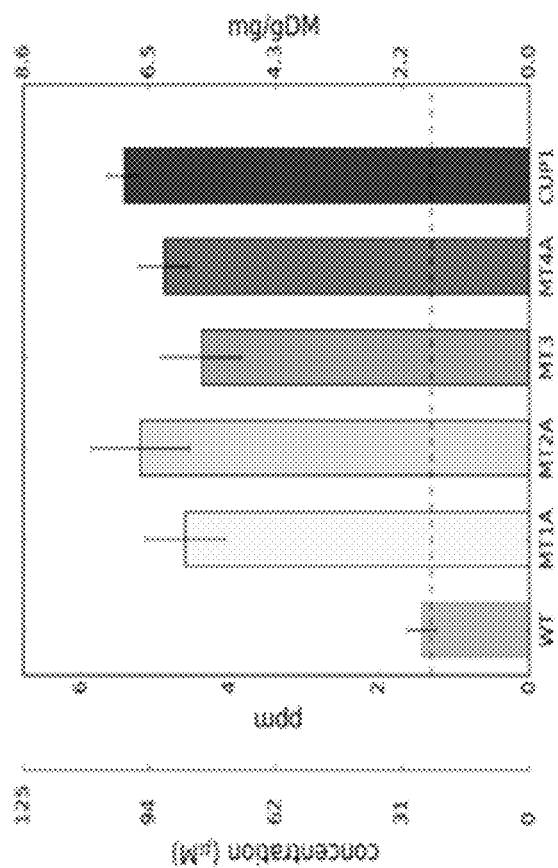

Yeast cell surface display of plant-based metal-binding proteins, known as metallothioneins (MTs), is analogous to the physicochemical ion-exchange technique. Four families of plant MTs (MT1A-MT4A in FIG. 27B) as well as the yeast endogenous metallothionein (CUP1) were expressed on the yeast surface and assayed for $Cu^{2+}$ uptake (the native ligand preferred by the metallothionein families) (FIG. 27A). The AGA1 and AGA2 (purple) domains were used to express peptides or proteins with metal binding domains to remove contaminants from waters (orange circles). Expression of MTs increased uptake capacity of $Cu^{2+}$ by 3-4 fold compared to wild-type yeast (FIG. 27B). In addition, expression of MTs increased tolerance of copper concentration in solution by 3-4 fold (FIG. 27C).

Given modest estimates of yeast density and expression levels, the upper limit of yeast display capture is in the submillimole range per gram of dry weight. On the other hand, synthetic ion-exchange resin capacities are in the 10 μmol-10 mmol of metal per gram of material (see Barakat, M. A., New Trends in Removing Heavy Metals from Industrial Wastewater. *Arabian Journal of Chemistry* 2011, 4 (4), 361-377, and Stathi, P.; Papadas, I. T.; Tselepidou, A.; Deligiannakis, Y., Heavy-Metal Uptake by a High Cation-Exchange-Capacity Montmorillonite: The Role of Permanent Charge Sites. *Global NEST Journal* 2010, 12 (3), 248-255, each of which is incorporated by reference in its entirety), up to 1-3 orders of magnitude greater than that demonstrated with the metallothionein yeast display experiments (FIG. 27B). Despite an overall lower binding capacity, an advantage of using yeast display as a method for metal capture is the ability to engineer highly specific metal-binding domains for extremely toxic metals, such as mercury, while avoiding nonspecific saturation from common ions such as Na, Ca, Mg, etc.

Figure 4:
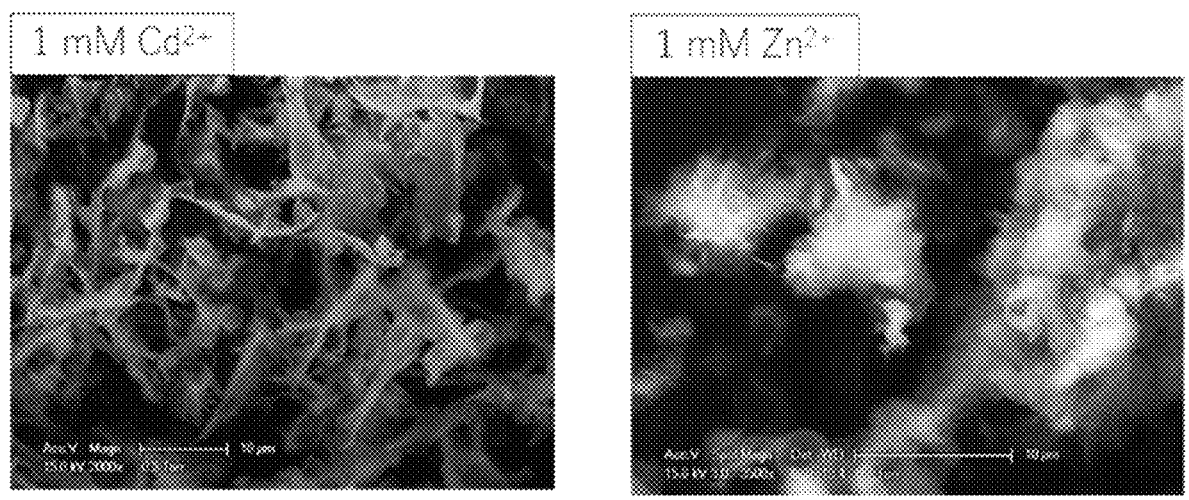
FIG. 4 shows SEM image of yeast with aggregated GS.

The shortcomings of traditional yeast cell surface display can be overcome, while retaining the ability to engineer heavy metal specificity, by the use of externally secreted multiplier proteins, which greatly increase the number of metal-binding domains available per gram of dry weight. MTs were then fused to a multiplier protein, glutamine synthetase (GS). GS is a dodecahedron protein with 12 subunits. Each subunit can be fused with a MT appendage on the N'-terminus. Glutamine synthetase was engineered to aggregate in response to a range of metals from zinc to cadmium (FIG. 2). This system uses one strain to express a single copy of the GS subunit on the yeast surface as the anchorage protein, with another strain secreting the GS-MT complex. In the presence of metals secreted GS-MT complexes being to aggregate and form on the yeast surface producing a mesh network (FIG. 4). Binding capacities are estimated to be enhanced by 2-3 orders of magnitude given the increased amount of metal uptake than compared to singly displayed MTs.

The plausibility of using yeast as a platform for metal remediation becomes even more readily apparent when incorporating multiplier proteins and proteins engineered for metal-specific binding into the remediation strategy. Doing so increases capture capacities to 1-10 mM, on par with synthetic ion-exchange resin capacities, and allows for specific metal uptake (FIG. 5, lower). In addition, due to their greater density, yeast bound to metals can settle out of solution allowing for easy physical separation from remediated waters (FIG. 5, upper).

In addition to possessing metal-binding proteins (MTs), certain plants can uptake large quantities of metals, known as hyperaccumulation. See Clemens, S.; Palmgren, M. G.; Kramer, U., A Long Way Ahead: Understanding and Engineering Plant Metal Accumulation. *Trends in Plant Science* 2002, 7 (7), 309-315, which is incorporated by reference in its entirety. Such hyperaccumulators often use metal transporter proteins for subsequent compartmentalization into organelles called vacuoles or bind metals using sequestration agents, primarily in the form of phytochelatins or metallothionein proteins. See Song, W. Y.; Park, J.; Mendoza-Cozatl, D. G.; Suter-Grotemeyer, M.; Shim, D.; Hortensteiner, S.; Geisler, M.; Weder, B.; Rea, P. A.; Rentsch, D.; Schroeder, J. I.; Lee, Y.; Martinoia, E., Arsenic Tolerance in *Arabidopsis* Is Mediated by Two Abcc-Type Phytochelatin Transporters. *Proceedings of the National Academy of Sciences of the United States of America* 2010, 107 (49), 21187-21192, and Cobbett, C.; Goldsbrough, P., Phytochelatins and Metallothioneins: Roles in Heavy Metal Detoxification and Homeostasis. *Annual Review of Plant Biology* 2002, 53, 159-182, each of which is incorporated by reference in its entirety. However, because plants are stationary, difficult to biologically engineer, and have a long growth cycle, plants are not the best candidates to develop a modular platform for a range of metal remediation tactics. Instead, this strategy is to use plants as inspiration to engineer yeast for heavy metal uptake and compartmentalization. There already exist numerous yeast metal transporters similar to those of plants that respond to various conditions such as pH, cofactors, and/or energy resources. The same is also true for vacuole transporters that secure toxins away from the yeast body.

Difficulty in predicting metal-binding regions and metal specificity regions in these transporter proteins has previously prevented rational design to attain better performance. See Arguello, J. M., Identification of Ion-Selectivity Determinants in Heavy-Metal Transport P-1b-Type ATPases. *Journal of Membrane Biology* 2003, 195 (2), 93-108, which is incorporated by reference in its entirety. Here, a screening method can use density changes in the yeast cell as a direct measurement to qualitatively discern metal uptake efficiency. Using established values for yeast cell density and mass (see Bryan, A. K.; Goranov, A.; Amon, A.; Manalis, S. R., Measurement of Mass, Density, and Volume During the Cell Cycle of Yeast. *Proceedings of the National Academy of Sciences of the United States of America* 2010, 107 (3), 999-1004, which is incorporated by reference in its entirety), even metal uptake in the hundreds of μM can induce density changes up to 25% depending on the molar mass of the metal. Density changes can be discerned using density gradient separation techniques, such as Percoll density centrifugation, which has a density resolution on the order of 2-3%. See Ravnik, S. E.; Gage, S.; Pollack, S. B., Self-Generating Density Gradients of Percoll Provide a Simple and Rapid Method That Consistently Enriches Natural-Killer Cells. *Journal of Immunological Methods* 1988, 110 (2), 161-168, and Childs, W. C.; Gibbons, R. J., Use of Percoll Density Gradients for Studying the Attachment of Bacteria to Oral Epithelial-Cells. *Journal of Dental*

Figure 28A:
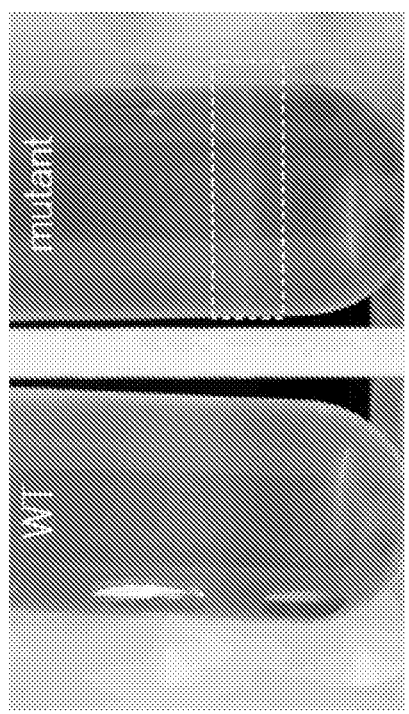
FIGS. 28A-28B show using Percoll density gradients to fractionate clones with improved metal uptake efficiency (see also FIG. 9).
Figure 28B:
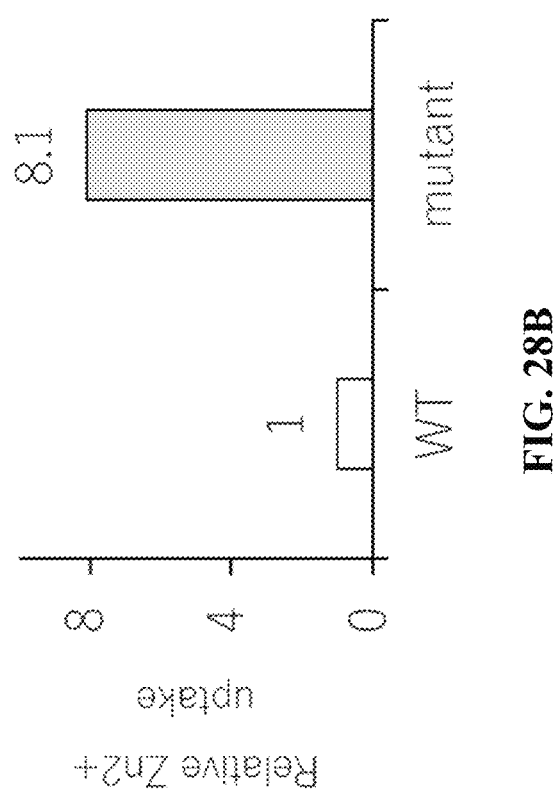

*Research* 1988, 67 (5), 826-830, each of which is incorporated by reference in its entirety. Using this density-based method, libraries of transporters can be assayed and screened for metal uptake efficiency given the direct physical change on yeast density, and better performing strains can be selected visually and filtered with increasingly more stringent density gradients (FIG. 28A).

Figure 29A:
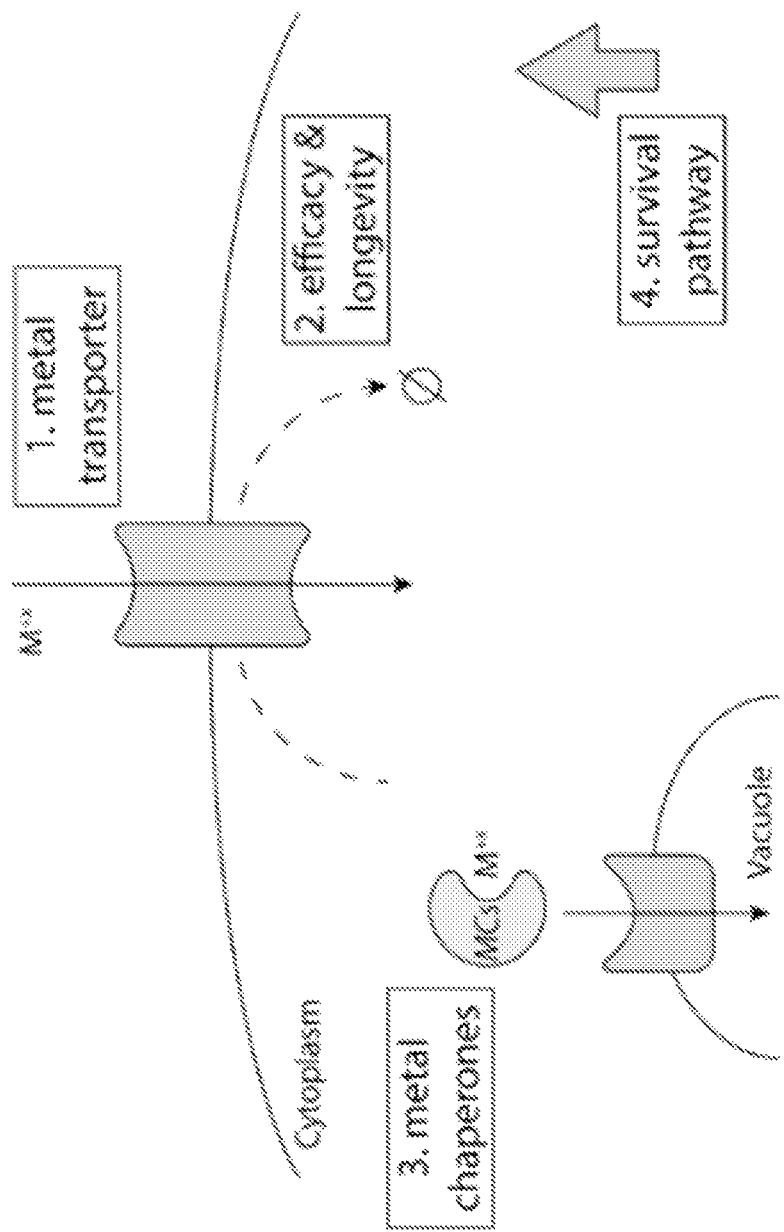
FIGS. 29A-29D show engineering metal transporters to enhance heavy metal uptake.
Figure 29B:
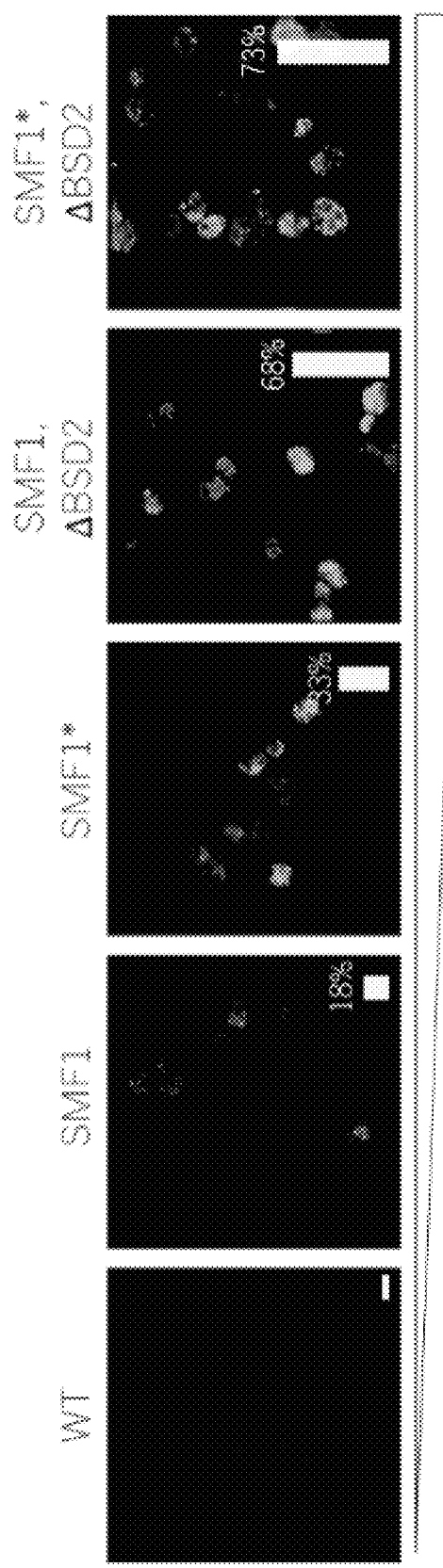
Figure 29C:
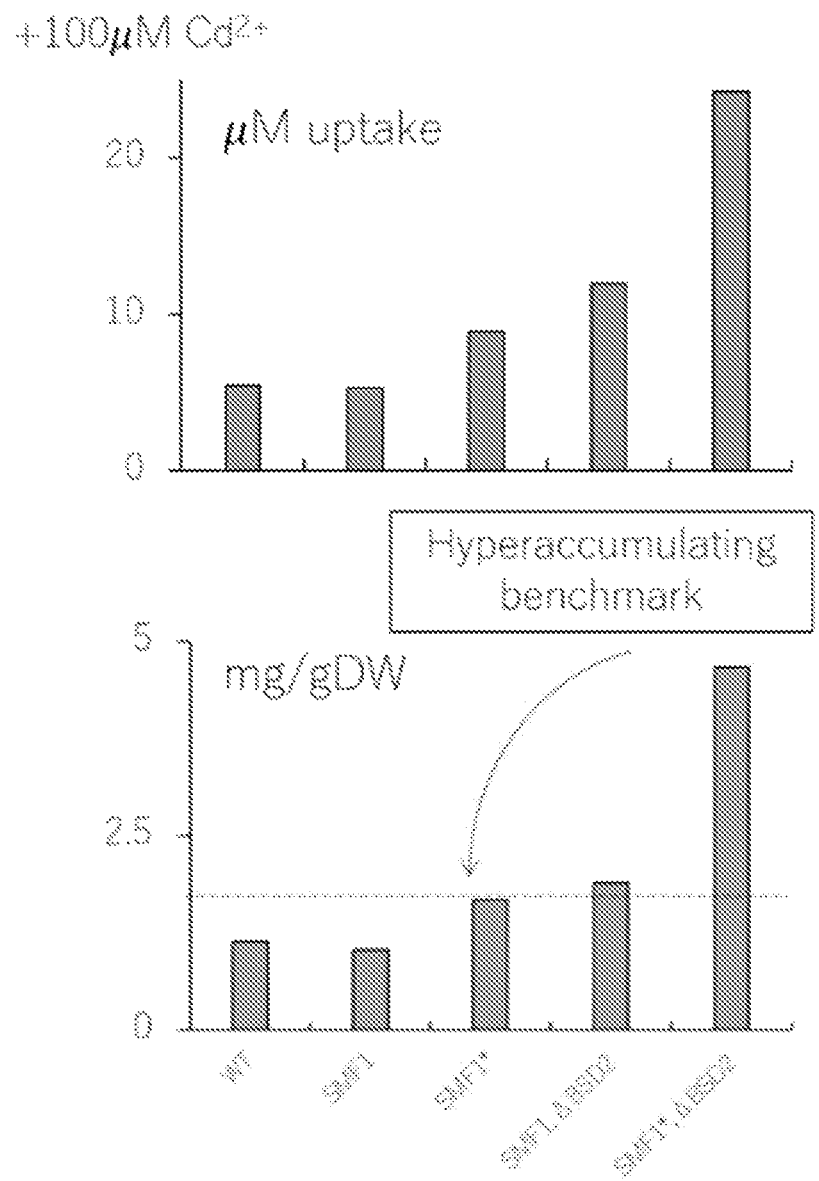
Figure 29D:
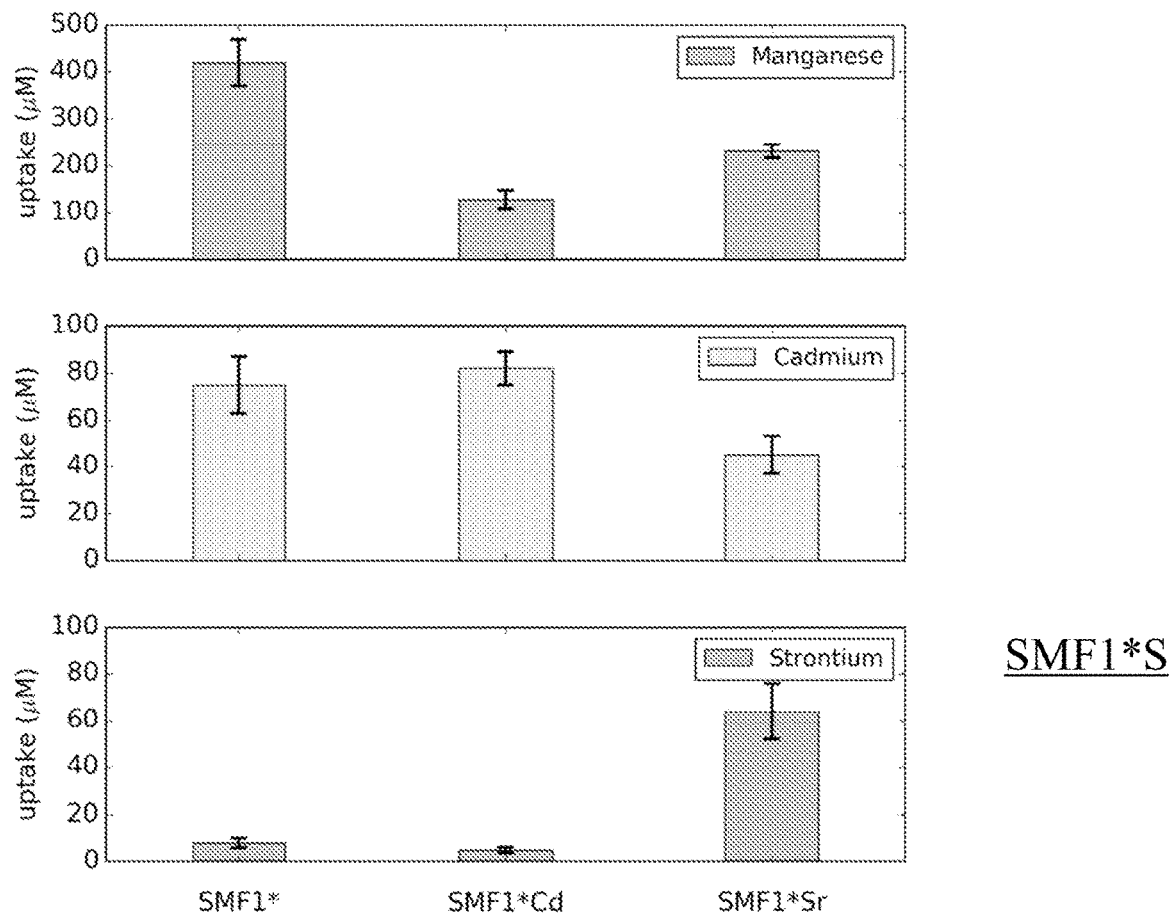
Figure 29D:
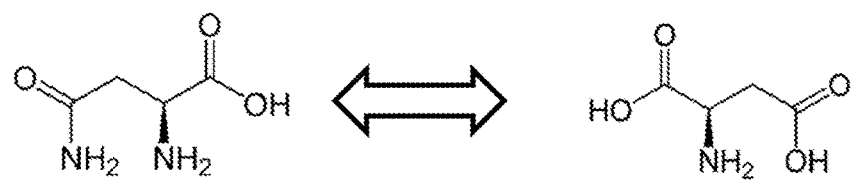

Expression of the metal transporter protein of interest can be increased, its degradation in regular cellular pathways can be reduced, the transported metals can be shuttled into vacuoles for containment, and finally yeast tolerance can be improved to increased levels of metal accumulation (FIG. 29A). One such transporter of interest is SMF1, a promiscuous divalent metal transporter which has been observed to uptake a range of metals such as manganese and cadmium. See Chen, X. Z.; Peng, J. B.; Cohen, A.; Nelson, II.; Nelson, N.; Hediger, M. A., Yeast Smf1 Mediates H+-Coupled Iron Uptake with Concomitant Uncoupled Cation Currents. *Journal of Biological Chemistry* 1999, 274 (49), 35089-35094, which is incorporated by reference in its entirety. SMF1, unlike most other metal transporter proteins, benefits from 30-40 years of sequence-function research. As such, SMF1 mutants were rationally designed and compared for their metal uptake capacities. FIG. 28A shows increased expression percentage as a function of SMF1 modifications, specifically conversion of lysine residues 33, 34 to arginine (denoted with *) and a deletion of SMF1's degradation protein BSD2 (denoted ΔBSD2). With these rationally designed modifications, cadmium accumulation was improved up to 4-fold greater than that of wild-type yeast. Notably, the best performing mutant so far is capable of exceeding 5 mg of cadmium per gram of yeast dry weight, which is beyond the threshold for classifying plants as cadmium hyperaccumulators (FIG. 29C). Modification of the SMF1 metal transporter confers metal hyperaccumulator status. See Rascio, N.; Navari-Izzo, F., Heavy Metal Hyperaccumulating Plants: How and Why Do They Do It? And What Makes Them So Interesting? *Plant Science* 2011, 180 (2), 169-181, which is incorporated by reference in its entirety. Given the modularity of this approach, the selection can be tailored for other metals of interest such as radium and strontium, elements that are becoming increasingly recognized as radioactive contaminants since the Fukushima incident in 2014. See Iwahana, Y.; Ohbuchi, A.; Koike, Y.; Kitano, M.; Nakamura, T., Radioactive Nuclides in the Incinerator Ashes of Municipal Solid Wastes before and after the Accident at the Fukushima Nuclear Power Plant. *Analytical Sciences* 2013, 29 (1), 61-66, which is incorporated by reference in its entirety. A suite of yeast that can uptake a range of toxic elements with high specificity can be developed in this way.

Another alternative strategy for metal remediation, in addition to yeast cell surface display and yeast capture and uptake, is to chemically reduce and precipitate metals from wastewaters. Chemical precipitation is the most widely used method for heavy metal remediation in industry, with hydrogen sulfide being one of the most commonly used chemical precipitants. See Fu, F. L.; Wang, Q., Removal of Heavy Metal Ions from Wastewaters: A Review. *Journal of Environmental Management* 2011, 92 (3), 407-418, and Metcalf, E.; Eddy, H. P.; Tchobanoglous, G., Wastewater Engineering: Treatment, Disposal and Reuse. *McGraw-Hill, New York* 1991, each of which is incorporated by reference in its entirety. On a tangential note, the wine industry discovered that yeasts are able to produce an appreciable amount of hydrogen sulfide during fermentation, causing wine to smell and taste pungent. See Swiegers, J. H.; Pretorius, I. S., Modulation of Volatile Sulfur Compounds by Wine Yeast. *Applied Microbiology and Biotechnology* 2007, 74 (5), 954-960, which is incorporated by reference in its entirety. To inhibit sulfur production for better tasting wine, Linderholm et al. and Huang et al. discovered that knockouts of metabolic proteins, MET2, MET17 and CYS4, overproduce hydrogen sulfide and are integral for complete sulfate metabolism for production of amino acids such as cysteine. See Linderholm, A. L.; Findleton, C. L.; Kumar, G.; Hong, Y.; Bisson, L. F., Identification of Genes Affecting Hydrogen Sulfide Formation in *Saccharomyces Cerevisiae*. *Applied and Environmental Microbiology* 2008, 74 (5), 1418-1427, and Huang, C.; Roncoroni, M.; Gardner, R. C., MET2 Affects Production of Hydrogen Sulfide During Wine Fermentation. *Applied Microbiology and Biotechnology* 2014, 98 (16), 7125-7135, each of which is incorporated by reference in its entirety.

Figure 30:
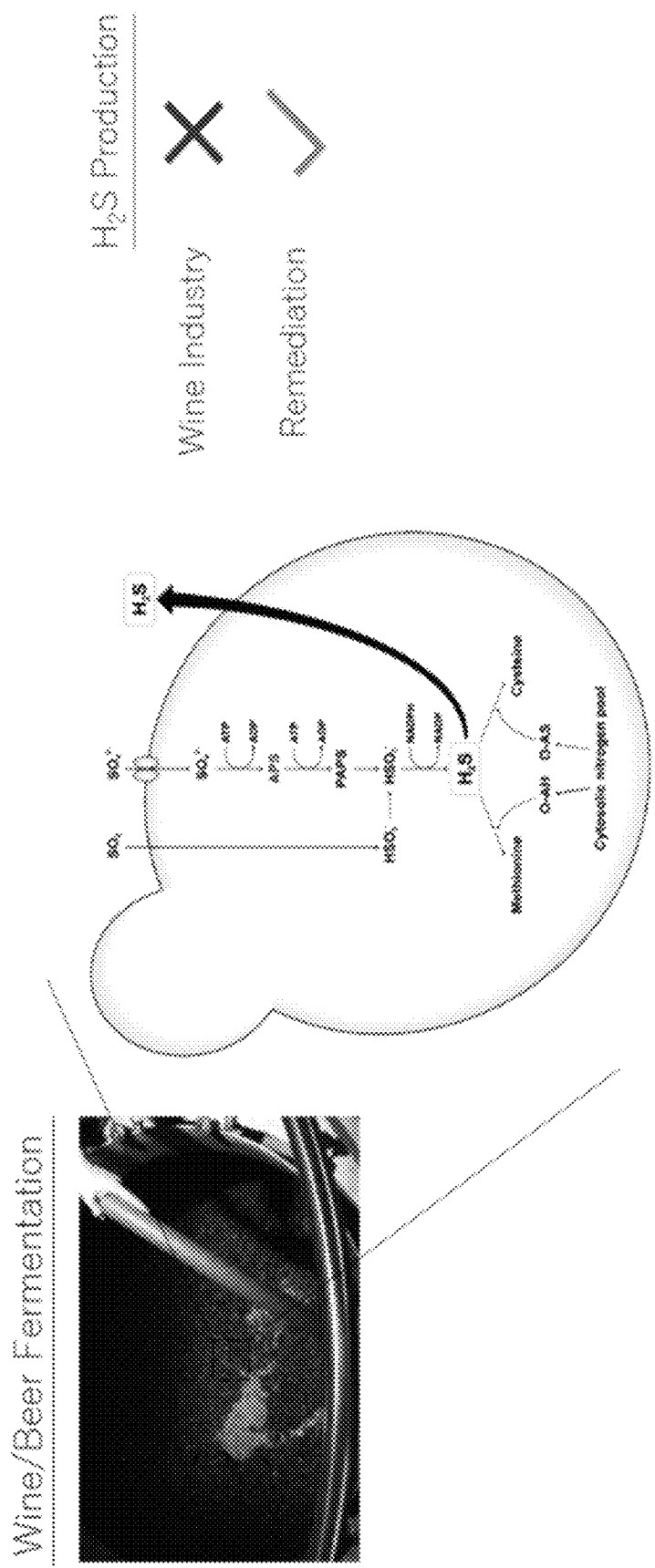
FIG. 30 shows wine yeast engineered to limit hydrogen sulfide production.
Figure 31B:
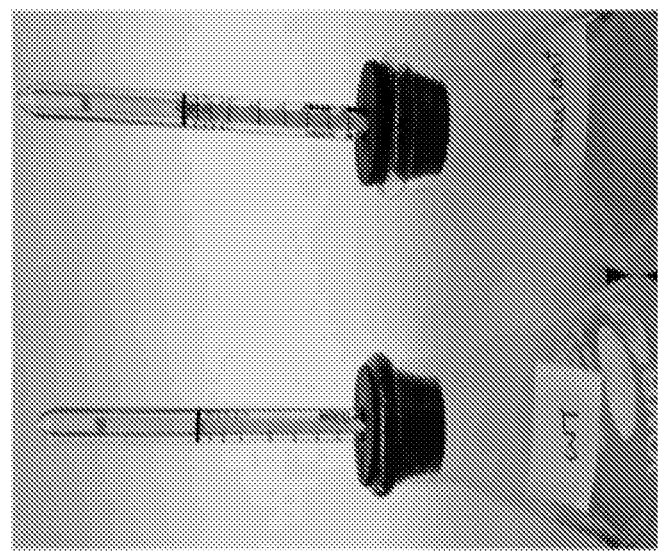
FIGS. 31A-31D show engineering yeast strains and detecting hydrogen sulfide production.
Figure 31A:
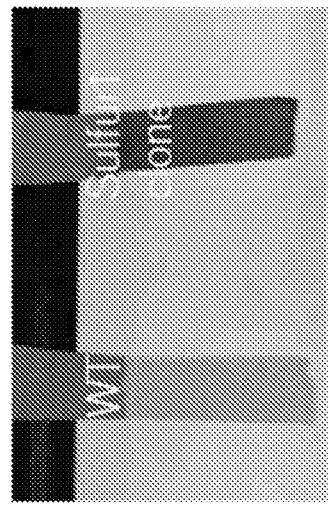
Figure 31C:
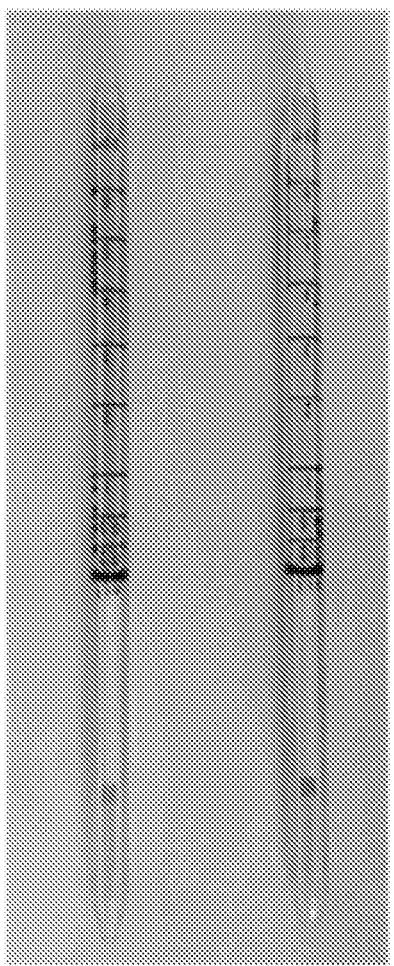
Figure 31D:
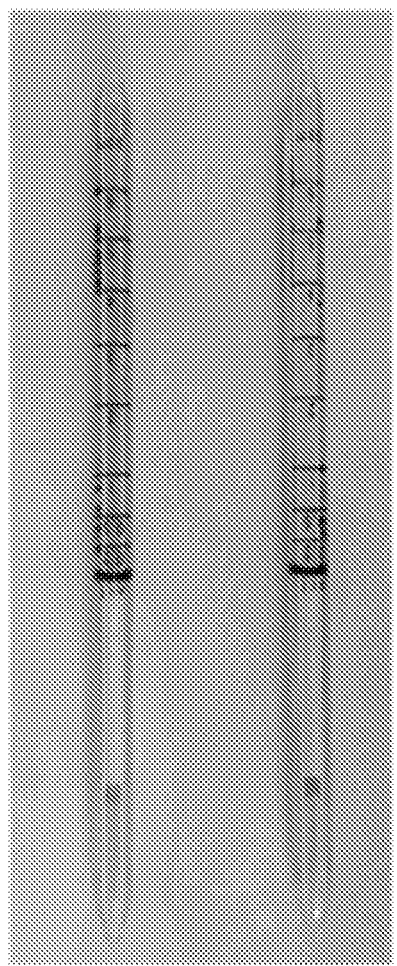

Because sulfur is a strong and reactive reducing and precipitating agent for most transition metals (see Charemtanyarak, L., Heavy Metals Removal by Chemical Coagulation and Precipitation. *Water Science and Technology* 1999, 39 (10-11), 135-138, which is incorporated by reference in its entirety), sulfur was aim to be overproduced, whereas the wine industry has attempted to inhibit sulfur production (FIG. 30). Overproducing hydrogen sulfide serves as a powerful method for metal remediation in the form of chemical precipitation. From here, either the first or second bioremediation strategy can be employed to bind or uptake, respectively, these sulfide-metal complexes.

To utilize this strategy for bioremediation, the sulfur assimilatory cycle need to be interrupted at the point of sulfate to sulfide conversion ($HSO_3^- \rightarrow S^{2-}$ [STOP]) and build up reactive sulfur in solution. Detection of hydrogen sulfide can be indirectly monitored from released hydrogen sulfide gas. Qualitative identification can be observed using lead acetate strips while quantitative measurements can be performed using sulfide detection columns, both of which undergo colorimetric changes in the presence of sulfur (FIGS. 31A-31D). Monitoring color changes shows a production rate of 2 ppm/hr with a maximum production of 55 pm during a complete culture cycle (<24 hr).

The successful mutant, ΔMET17, is able to produce roughly 2 ppm/hr of hydrogen sulfide with a total of 55 ppm during a complete inoculation experiment (>24 hr) in CSM. Cultures seeded with cadmium or copper precipitate to CdS and CuS, respectively, showed a conversion of 90±5% of the initial metal concentration (FIGS. 34A-34B). Bioprecipitated metal sulfides, such as CdS, are regularly used as quantum dots. Reacted CdS from yeast behaves with characteristic excitation and emission wavelengths of that of typical quantum dots. The size of the CdS particles is approximately 50 nm in diameter, consistent with the expected size that contributes to the quantum confinement of electrons given the distinct excitation and emission peaks (FIG. 32C).

Figure 33B:
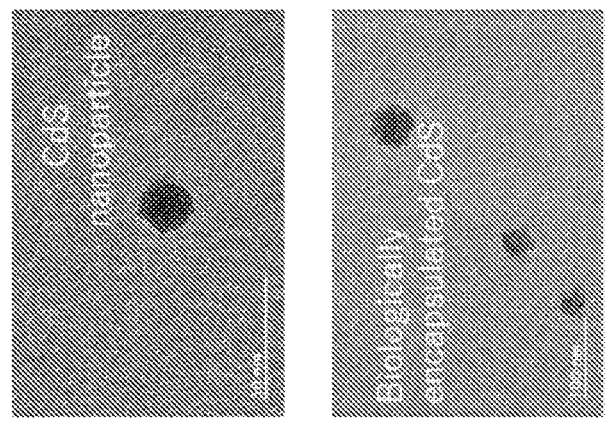
FIGS. 33A-33B show cross section TEM images of yeast cells with CdS embedded in the cell wall.
Figure 33A:
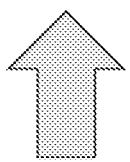
Figure 33A:
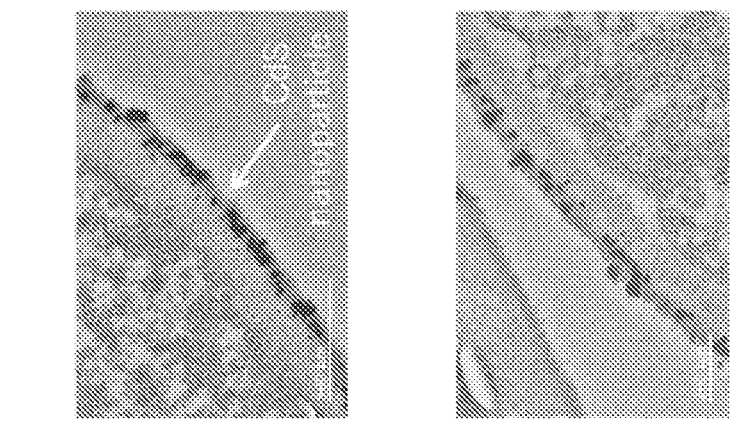
Figure 33A:
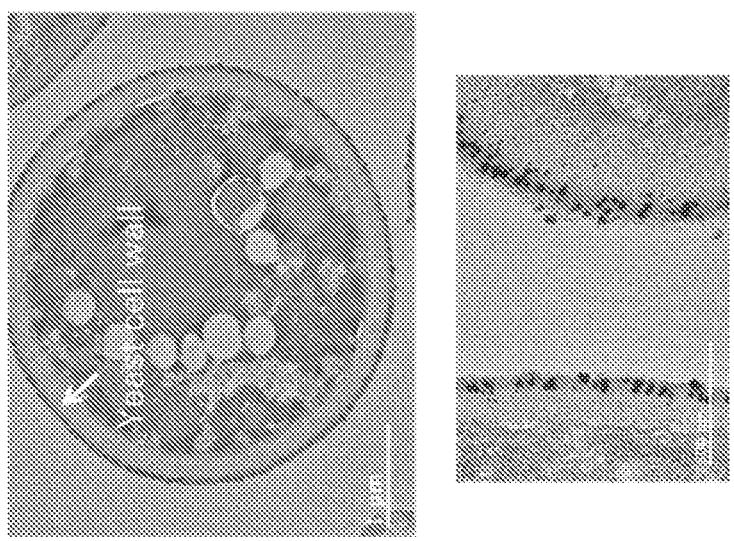

These CdS particles are embedded in the cell wall using cross-sectioning TEM (FIG. 33A). The cell wall can then be digested using zymolase to release the particles, and a uniform distribution of CdS particle sizes, as well as some CdS particles encapsulated in biologically derived material (e.g., protein or cell wall debris) were observed (FIG. 33B).

Packaging and Deployment

Another option is to store yeast in freeze-dried or active dry packages, much as baker's yeast are stored for consumer use, and distribute them for on-demand applications. Large quantities of packaged yeast can be stored for later use during the events of disaster spills or contamination leaks much like the BP oil spill, Fukushima nuclear disaster, and the Flint water crisis in 2010, 2012, and 2014, respectively. Deployable units of the engineered yeast can be created for on-site waste treatment. Options to create such a device may include constructing a filtering device that supports a resin-like bed of yeast.

Reducing the cost and scaling up the yeast technology can take advantage of the already established infrastructure for mass-producing yeast for consumer purposes. The beer, wine, and pharmaceutical industries have optimized large-scale production of yeast, so there is already developed infrastructure to produce yeast in mass. The production and consumption of bread, beer, and medicine can be concurrently used to clean contaminated waters (FIGS. 34A-34B).

Other embodiments are within the scope of the following claims.

What is claimed is:

1. A composition for remediating a metal to treat water comprising:
    an engineered yeast cell having a functionalized surface expressing a genetically engineered mutant membrane metal transporter, wherein the mutant membrane metal transporter has specificity for a metal and increases uptake;
    a vacuole transporter; and
    a metal sequestration protein.

2. The composition of claim 1, wherein an ubiquitination ligase is deleted in the yeast.

3. The composition of claim 2, wherein the ubiquitination ligase is BSD2.

4. The composition of claim 1, wherein the membrane metal transporter is S1V1F1.

5. The composition of claim 1, wherein the vacuole transporter is CCC1.

6. The composition of claim 1, wherein the metal sequestration protein is a phytochelatin synthase.

7. The composition of claim 1, wherein the membrane transporter is SMF1, CTR1, ZRT1 or FRE1, and the membrane transporter and is mutated to be sensitive to the metal and increase uptake.

8. The composition for remediating a metal to treat water comprising:
    an engineered yeast cell having a functionalized surface expressing a genetically engineered mutant membrane metal transporter, wherein the mutant membrane metal transporter has specificity for a metal and increases uptake;
    a vacuole transporter; and
    a metal sequestration protein, wherein the metal is strontium, lead or mercury.

9. The composition of claim 4, wherein SMF1 is mutated to destroy primary ubiquitination sites.

10. The composition of claim 1, wherein the membrane metal transporter is Sul1 or Sul2.

11. The composition of claim 10, wherein the metal is chromate.

12. The composition of claim 1, wherein the metal is copper.

13. The composition of claim 1, wherein the metal is zinc.

14. The composition of claim 1, wherein the metal is iron.

15. A method of remediating a metal to treat water comprising:
    contacting water with the composition of claim 1.

16. The method of claim 15, wherein the metal is lithium.

17. The method of claim 15, wherein the metal is a noble metal.

18. The method of claim 15, wherein the noble metal is gold, silver or platinum.

19. The method of claim 15, wherein the metal is a rare-earth metal.

20. The method of claim 15, wherein the rare-earth metal is cerium (Ce), dysprosium (Dy), erbium (Er), europium (Eu), gadolinium (Gd), holmium (Ho), lanthanum (La), lutetium (Lu), neodymium (Nd), praseodymium (Pr), promethium (Pm), samarium (Sm), scandium (Sc), terbium (Tb), thulium (Tm), ytterbium (Yb) or yttrium (Y).

21. A method of mining a metal comprising:
    contacting water with the composition of claim 1; and
    lysing the cell to obtain the metal.

* * * * *

SEQUENCE LISTING

```
<160> NUMBER OF SEQ ID NOS: 9

<210> SEQ ID NO 1
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (3)..(5)
<223> OTHER INFORMATION: a, c, t, g, unknown or other
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: modified_base
<222> LOCATION: (9)..(11)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other
<220> FEATURE:
<221> NAME/KEY: modified_base
<222> LOCATION: (15)..(17)
<223> OTHER INFORMATION: a, c, t, g, unknown or other
<220> FEATURE:
<221> NAME/KEY: modified_base
<222> LOCATION: (19)..(19)
<223> OTHER INFORMATION: a, c, t, g, unknown or other
<220> FEATURE:
<221> NAME/KEY: modified_base
<222> LOCATION: (21)..(23)
<223> OTHER INFORMATION: a, c, t, g, unknown or other
<220> FEATURE:
<221> NAME/KEY: modified_base
<222> LOCATION: (25)..(25)
<223> OTHER INFORMATION: a, c, t, g, unknown or other
<220> FEATURE:
<221> NAME/KEY: modified_base
<222> LOCATION: (27)..(29)
<223> OTHER INFORMATION: a, c, t, g, unknown or other
<220> FEATURE:
<221> NAME/KEY: modified_base
<222> LOCATION: (31)..(31)
<223> OTHER INFORMATION: a, c, t, g, unknown or other
<220> FEATURE:
<221> NAME/KEY: modified_base
<222> LOCATION: (33)..(35)
<223> OTHER INFORMATION: a, c, t, g, unknown or other
<220> FEATURE:
<221> NAME/KEY: modified_base
<222> LOCATION: (37)..(37)
<223> OTHER INFORMATION: a, c, t, g, unknown or other
<220> FEATURE:
<221> NAME/KEY: modified_base
<222> LOCATION: (39)..(41)
<223> OTHER INFORMATION: a, c, t, g, unknown or other
<220> FEATURE:
<221> NAME/KEY: modified_base
```

<222> LOCATION: (43)..(43)
<223> OTHER INFORMATION: a, c, t, g, unknown or other
<220> FEATURE:
<221> NAME/KEY: modified_base
<222> LOCATION: (45)..(47)
<223> OTHER INFORMATION: a, c, t, g, unknown or other

<400> SEQUENCE: 1
ndnnnkndnn nkndnnnknd nnnkndnnnk ndnnnkndnn nkndnnnk        48

<210> SEQ ID NO 2
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (3)..(5)
<223> OTHER INFORMATION: a, c, t, g, unknown or other
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: modified_base
<222> LOCATION: (9)..(11)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other
<220> FEATURE:
<221> NAME/KEY: modified_base
<222> LOCATION: (15)..(17)
<223> OTHER INFORMATION: a, c, t, g, unknown or other
<220> FEATURE:
<221> NAME/KEY: modified_base
<222> LOCATION: (19)..(19)
<223> OTHER INFORMATION: a, c, t, g, unknown or other
<220> FEATURE:
<221> NAME/KEY: modified_base
<222> LOCATION: (21)..(23)
<223> OTHER INFORMATION: a, c, t, g, unknown or other
<220> FEATURE:
<221> NAME/KEY: modified_base
<222> LOCATION: (25)..(25)
<223> OTHER INFORMATION: a, c, t, g, unknown or other
<220> FEATURE:
<221> NAME/KEY: modified_base
<222> LOCATION: (27)..(29)
<223> OTHER INFORMATION: a, c, t, g, unknown or other
<220> FEATURE:
<221> NAME/KEY: modified_base
<222> LOCATION: (31)..(31)
<223> OTHER INFORMATION: a, c, t, g, unknown or other
<220> FEATURE:
<221> NAME/KEY: modified_base
<222> LOCATION: (33)..(35)
<223> OTHER INFORMATION: a, c, t, g, unknown or other
<220> FEATURE:
<221> NAME/KEY: modified_base
<222> LOCATION: (37)..(37)
<223> OTHER INFORMATION: a, c, t, g, unknown or other
<220> FEATURE:
<221> NAME/KEY: modified_base
<222> LOCATION: (39)..(41)
<223> OTHER INFORMATION: a, c, t, g, unknown or other
<220> FEATURE:
<221> NAME/KEY: modified_base
<222> LOCATION: (43)..(43)
<223> OTHER INFORMATION: a, c, t, g, unknown or other

```
<220> FEATURE:
<221> NAME/KEY: modified_base
<222> LOCATION: (45)..(47)
<223> OTHER INFORMATION: a, c, t, g, unknown or other
<220> FEATURE:
<221> NAME/KEY: modified_base
<222> LOCATION: (49)..(49)
<223> OTHER INFORMATION: a, c, t, g, unknown or other
<220> FEATURE:
<221> NAME/KEY: modified_base
<222> LOCATION: (51)..(53)
<223> OTHER INFORMATION: a, c, t, g, unknown or other
<220> FEATURE:
<221> NAME/KEY: modified_base
<222> LOCATION: (55)..(55)
<223> OTHER INFORMATION: a, c, t, g, unknown or other
<220> FEATURE:
<221> NAME/KEY: modified_base
<222> LOCATION: (57)..(59)
<223> OTHER INFORMATION: a, c, t, g, unknown or other
<220> FEATURE:
<221> NAME/KEY: modified_base
<222> LOCATION: (61)..(61)
<223> OTHER INFORMATION: a, c, t, g, unknown or other
<220> FEATURE:
<221> NAME/KEY: modified_base
<222> LOCATION: (63)..(65)
<223> OTHER INFORMATION: a, c, t, g, unknown or other
<220> FEATURE:
<221> NAME/KEY: modified_base
<222> LOCATION: (67)..(67)
<223> OTHER INFORMATION: a, c, t, g, unknown or other
<220> FEATURE:
<221> NAME/KEY: modified_base
<222> LOCATION: (69)..(71)
<223> OTHER INFORMATION: a, c, t, g, unknown or other

<400> SEQUENCE: 2
ndnnnkndnn nkndnnnknd nnnkndnnnk ndnnnkndnn nkndnnnknd nnnkndnnnk      60
ndnnnkndnn nk                                                          72

<210> SEQ ID NO 3
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (3)..(5)
<223> OTHER INFORMATION: a, c, t, g, unknown or other
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: modified_base
<222> LOCATION: (9)..(11)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other
<220> FEATURE:
<221> NAME/KEY: modified_base
<222> LOCATION: (15)..(17)
<223> OTHER INFORMATION: a, c, t, g, unknown or other
<220> FEATURE:
<221> NAME/KEY: modified_base
<222> LOCATION: (19)..(19)
<223> OTHER INFORMATION: a, c, t, g, unknown or other
```

```
<220> FEATURE:
<221> NAME/KEY: modified_base
<222> LOCATION: (21)..(23)
<223> OTHER INFORMATION: a, c, t, g, unknown or other
<220> FEATURE:
<221> NAME/KEY: modified_base
<222> LOCATION: (25)..(25)
<223> OTHER INFORMATION: a, c, t, g, unknown or other
<220> FEATURE:
<221> NAME/KEY: modified_base
<222> LOCATION: (27)..(29)
<223> OTHER INFORMATION: a, c, t, g, unknown or other
<220> FEATURE:
<221> NAME/KEY: modified_base
<222> LOCATION: (31)..(31)
<223> OTHER INFORMATION: a, c, t, g, unknown or other
<220> FEATURE:
<221> NAME/KEY: modified_base
<222> LOCATION: (33)..(35)
<223> OTHER INFORMATION: a, c, t, g, unknown or other
<220> FEATURE:
<221> NAME/KEY: modified_base
<222> LOCATION: (37)..(37)
<223> OTHER INFORMATION: a, c, t, g, unknown or other
<220> FEATURE:
<221> NAME/KEY: modified_base
<222> LOCATION: (39)..(41)
<223> OTHER INFORMATION: a, c, t, g, unknown or other
<220> FEATURE:
<221> NAME/KEY: modified_base
<222> LOCATION: (43)..(43)
<223> OTHER INFORMATION: a, c, t, g, unknown or other
<220> FEATURE:
<221> NAME/KEY: modified_base
<222> LOCATION: (45)..(47)
<223> OTHER INFORMATION: a, c, t, g, unknown or other
<220> FEATURE:
<221> NAME/KEY: modified_base
<222> LOCATION: (49)..(49)
<223> OTHER INFORMATION: a, c, t, g, unknown or other
<220> FEATURE:
<221> NAME/KEY: modified_base
<222> LOCATION: (51)..(53)
<223> OTHER INFORMATION: a, c, t, g, unknown or other
<220> FEATURE:
<221> NAME/KEY: modified_base
<222> LOCATION: (55)..(55)
<223> OTHER INFORMATION: a, c, t, g, unknown or other
<220> FEATURE:
<221> NAME/KEY: modified_base
<222> LOCATION: (57)..(59)
<223> OTHER INFORMATION: a, c, t, g, unknown or other
<220> FEATURE:
<221> NAME/KEY: modified_base
<222> LOCATION: (61)..(61)
<223> OTHER INFORMATION: a, c, t, g, unknown or other
<220> FEATURE:
<221> NAME/KEY: modified_base
<222> LOCATION: (63)..(65)
<223> OTHER INFORMATION: a, c, t, g, unknown or other
<220> FEATURE:
<221> NAME/KEY: modified_base
<222> LOCATION: (67)..(67)
<223> OTHER INFORMATION: a, c, t, g, unknown or other
<220> FEATURE:
<221> NAME/KEY: modified_base
<222> LOCATION: (69)..(71)
<223> OTHER INFORMATION: a, c, t, g, unknown or other
<220> FEATURE:
<221> NAME/KEY: modified_base
<222> LOCATION: (73)..(73)
<223> OTHER INFORMATION: a, c, t, g, unknown or other
<220> FEATURE:
<221> NAME/KEY: modified_base
<222> LOCATION: (75)..(77)
<223> OTHER INFORMATION: a, c, t, g, unknown or other
<220> FEATURE:
<221> NAME/KEY: modified_base
<222> LOCATION: (79)..(79)
```

```
<223> OTHER INFORMATION: a, c, t, g, unknown or other
<220> FEATURE:
<221> NAME/KEY: modified_base
<222> LOCATION: (81)..(83)
<223> OTHER INFORMATION: a, c, t, g, unknown or other
<220> FEATURE:
<221> NAME/KEY: modified_base
<222> LOCATION: (85)..(85)
<223> OTHER INFORMATION: a, c, t, g, unknown or other
<220> FEATURE:
<221> NAME/KEY: modified_base
<222> LOCATION: (87)..(89)
<223> OTHER INFORMATION: a, c, t, g, unknown or other
<220> FEATURE:
<221> NAME/KEY: modified_base
<222> LOCATION: (91)..(91)
<223> OTHER INFORMATION: a, c, t, g, unknown or other
<220> FEATURE:
<221> NAME/KEY: modified_base
<222> LOCATION: (93)..(95)
<223> OTHER INFORMATION: a, c, t, g, unknown or other

<400> SEQUENCE: 3
ndnnnkndnn nkndnnnknd nnnkndnnnk ndnnnkndnn nkndnnnknd nnnkndnnnk      60
ndnnnkndnn nkndnnnknd nnnkndnnnk ndnnnk                                96

<210> SEQ ID NO 4
<211> LENGTH: 45
<212> TYPE: PRT
<213> ORGANISM: Arabidopsis thaliana

<400> SEQUENCE: 4

Met Ala Asp Ser Asn Cys Gly Cys Gly Ser Ser Cys Lys Cys Gly Asp
1               5                   10                  15

Ser Cys Ser Cys Glu Lys Asn Tyr Asn Lys Glu Cys Asp Asn Cys Ser
            20                  25                  30

Cys Gly Ser Asn Cys Ser Cys Gly Ser Asn Cys Asn Cys
        35                  40                  45

<210> SEQ ID NO 5
<211> LENGTH: 81
<212> TYPE: PRT
<213> ORGANISM: Arabidopsis thaliana

<400> SEQUENCE: 5

Met Ser Cys Cys Gly Gly Asn Cys Gly Cys Gly Ser Gly Cys Lys Cys
1               5                   10                  15

Gly Asn Gly Cys Gly Gly Cys Lys Met Tyr Pro Asp Leu Gly Phe Ser
            20                  25                  30

Gly Glu Thr Thr Thr Thr Glu Thr Phe Val Leu Gly Val Ala Pro Ala
        35                  40                  45

Met Lys Asn Gln Tyr Glu Ala Ser Gly Glu Ser Asn Asn Ala Glu Asn
    50                  55                  60

Asp Ala Cys Lys Cys Gly Ser Asp Cys Lys Cys Asp Pro Cys Thr Cys
65                  70                  75                  80

Lys

<210> SEQ ID NO 6
<211> LENGTH: 69
<212> TYPE: PRT
<213> ORGANISM: Arabidopsis thaliana

<400> SEQUENCE: 6

Met Ser Ser Asn Cys Gly Ser Cys Asp Cys Ala Asp Lys Thr Gln Cys
```

```
1               5                   10                  15
Val Lys Lys Gly Thr Ser Tyr Thr Phe Asp Ile Val Glu Thr Gln Glu
              20                  25                  30

Ser Tyr Lys Glu Ala Met Ile Met Asp Val Gly Ala Glu Glu Asn Asn
              35                  40                  45

Ala Asn Cys Lys Cys Lys Cys Gly Ser Ser Cys Ser Cys Val Asn Cys
              50                  55                  60

Thr Cys Cys Pro Asn
65

<210> SEQ ID NO 7
<211> LENGTH: 84
<212> TYPE: PRT
<213> ORGANISM: Arabidopsis thaliana

<400> SEQUENCE: 7

Met Ala Asp Thr Gly Lys Gly Ser Ser Val Ala Gly Cys Asn Asp Ser
1               5                   10                  15

Cys Gly Cys Pro Ser Pro Cys Pro Gly Gly Asn Ser Cys Arg Cys Arg
              20                  25                  30

Met Arg Glu Ala Ser Ala Gly Asp Gln Gly His Met Val Cys Pro Cys
              35                  40                  45

Gly Glu His Cys Gly Cys Asn Pro Cys Asn Cys Pro Lys Thr Gln Thr
              50                  55                  60

Gln Thr Ser Ala Lys Gly Cys Thr Cys Gly Glu Gly Cys Thr Cys Ala
65                  70                  75                  80

Ser Cys Ala Thr

<210> SEQ ID NO 8
<211> LENGTH: 62
<212> TYPE: PRT
<213> ORGANISM: Arabidopsis thaliana

<400> SEQUENCE: 8

Asn Ile Phe Ser Glu Leu Ile Asn Phe Gln Asn Glu Gly His Glu Cys
1               5                   10                  15

Gln Cys Gln Cys Gly Ser Cys Lys Asn Asn Glu Gln Cys Gln Lys Ser
              20                  25                  30

Cys Ser Cys Pro Thr Gly Cys Asn Ser Asp Asp Lys Cys Pro Cys Gly
              35                  40                  45

Asn Lys Ser Glu Glu Thr Lys Lys Ser Cys Cys Ser Gly Lys
              50                  55                  60

<210> SEQ ID NO 9
<211> LENGTH: 9
<212> TYPE: PRT
<213> ORGANISM: Human influenza virus

<400> SEQUENCE: 9

Tyr Pro Tyr Asp Val Pro Asp Tyr Ala
1               5
```